US009687247B2

(12) United States Patent
Aranyi et al.

(10) Patent No.: US 9,687,247 B2
(45) **Date of Patent: *Jun. 27, 2017**

(54) APPARATUS FOR APPLYING SURGICAL CLIPS

(71) Applicant: Covidien LP, Mansfield, MA (US)

(72) Inventors: Ernest Aranyi, Easton, CT (US); Kenneth H. Whitfield, North Haven, CT (US); Greg Sorrentino, Wallingford, CT (US)

(73) Assignee: Covidien LP, Mansfield, MA (US)

(*) Notice: Subject to any disclaimer, the term of this patent is extended or adjusted under 35 U.S.C. 154(b) by 269 days.

This patent is subject to a terminal disclaimer.

(21) Appl. No.: 14/551,546

(22) Filed: Nov. 24, 2014

(65) Prior Publication Data

US 2015/0080916 A1 Mar. 19, 2015

Related U.S. Application Data

(63) Continuation of application No. 11/245,866, filed on Oct. 7, 2005, now Pat. No. 8,920,438.

(60) Provisional application No. 60/617,017, filed on Oct. 8, 2004.

(51) Int. Cl.

| | |
|---|---|
| ***A61B 17/10*** | (2006.01) |
| ***A61B 17/128*** | (2006.01) |
| ***A61B 17/12*** | (2006.01) |

(52) U.S. Cl.

CPC .......... *A61B 17/1285* (2013.01); *A61B 17/12* (2013.01); *A61B 17/128* (2013.01); *A61B 2017/12004* (2013.01)

(58) Field of Classification Search

CPC ... A61B 17/12; A61B 17/1285; A61B 17/128; A61B 2017/12004

See application file for complete search history.

(56) References Cited

U.S. PATENT DOCUMENTS

| | | | |
|---|---|---|---|
| 3,120,230 | A | 2/1964 | Skold |
| 3,363,628 | A | 1/1968 | Wood |
| 3,638,847 | A | 2/1972 | Noiles et al. |

(Continued)

FOREIGN PATENT DOCUMENTS

| | | | |
|---|---|---|---|
| AU | 2010200641 | A1 | 10/2010 |
| CA | 2740831 | A1 | 4/2010 |

(Continued)

OTHER PUBLICATIONS

The extended European Search Report corresponding to European Application No. EP 07 25 3905.9, completed Jan. 29, 2008; mailed Feb. 7, 2008; (7 Pages).

(Continued)

*Primary Examiner* — Todd J Scherbel
*Assistant Examiner* — Son Dang

(57) ABSTRACT

A clip applying apparatus is described for applying clips seriatim to tissue. The apparatus includes a lockout member for limiting distal movement of the camming member after the proximal-most clip has been applied to tissue. In one embodiment, the apparatus includes a jaw locking member for preventing approximation of the jaw members of the apparatus. In one embodiment, a latch assembly is provided to releasably engage a clip pusher of the apparatus to the camming member of the apparatus.

21 Claims, 32 Drawing Sheets

(56) References Cited

U.S. PATENT DOCUMENTS

| | | | |
|---|---|---|---|
| 3,675,688 A | | 7/1972 | Bryan et al. |
| 3,735,762 A | | 5/1973 | Bryan et al. |
| 3,867,944 A | | 2/1975 | Samuels |
| 4,242,902 A | | 1/1981 | Green |
| 4,296,751 A | | 10/1981 | Blake, III et al. |
| 4,372,316 A | | 2/1983 | Blake, III et al. |
| 4,408,603 A | | 10/1983 | Blake, III et al. |
| 4,412,539 A | | 11/1983 | Jarvik |
| 4,430,997 A | | 2/1984 | DiGiovanni et al. |
| 4,449,531 A | | 5/1984 | Cerwin et al. |
| 4,478,220 A | | 10/1984 | Di Giovanni et al. |
| 4,480,640 A | | 11/1984 | Becht |
| 4,480,641 A | | 11/1984 | Failla et al. |
| 4,487,204 A | | 12/1984 | Hrouda |
| 4,487,205 A | | 12/1984 | Di Giovanni et al. |
| 4,491,133 A | | 1/1985 | Menges et al. |
| 4,492,232 A | | 1/1985 | Green |
| 4,498,476 A | | 2/1985 | Cerwin et al. |
| 4,500,024 A | | 2/1985 | DiGiovanni et al. |
| 4,509,518 A | | 4/1985 | McGarry et al. |
| 4,512,345 A | | 4/1985 | Green |
| 4,522,207 A | | 6/1985 | Klieman et al. |
| 4,532,925 A | | 8/1985 | Blake, III |
| 4,534,351 A | | 8/1985 | Rothfuss et al. |
| 4,545,377 A | | 10/1985 | Cerwin et al. |
| 4,549,544 A | | 10/1985 | Favaron |
| 4,556,058 A | | 12/1985 | Green |
| 4,557,263 A | | 12/1985 | Green |
| 4,562,839 A | | 1/1986 | Blake, III et al. |
| 4,572,183 A | | 2/1986 | Juska |
| 4,576,165 A | | 3/1986 | Green et al. |
| 4,576,166 A | | 3/1986 | Montgomery et al. |
| 4,590,937 A | | 5/1986 | Deniega |
| 4,592,498 A | | 6/1986 | Braun et al. |
| 4,598,711 A | | 7/1986 | Deniega |
| 4,602,631 A | | 7/1986 | Funatsu |
| 4,611,595 A | | 9/1986 | Klieman et al. |
| 4,612,932 A | | 9/1986 | Caspar et al. |
| 4,616,650 A | | 10/1986 | Green et al. |
| 4,616,651 A | | 10/1986 | Golden |
| 4,624,254 A | | 11/1986 | McGarry et al. |
| 4,637,395 A | | 1/1987 | Caspar et al. |
| 4,646,740 A | | 3/1987 | Peters et al. |
| 4,647,504 A | | 3/1987 | Kimimura et al. |
| 4,658,822 A | | 4/1987 | Kees, Jr. |
| 4,660,558 A | | 4/1987 | Kees, Jr. |
| 4,662,373 A | | 5/1987 | Montgomery et al. |
| 4,662,374 A | | 5/1987 | Blake, III |
| 4,671,278 A | | 6/1987 | Chin |
| 4,671,282 A | | 6/1987 | Tretbar |
| 4,674,504 A | | 6/1987 | Klieman et al. |
| 4,681,107 A | | 7/1987 | Kees, Jr. |
| 4,696,396 A | | 9/1987 | Samuels |
| 4,702,247 A | | 10/1987 | Blake, III et al. |
| 4,706,668 A | | 11/1987 | Backer |
| 4,712,549 A | | 12/1987 | Peters et al. |
| 4,733,666 A | | 3/1988 | Mercer, Jr. |
| 4,759,364 A | | 7/1988 | Boebel |
| 4,765,335 A | | 8/1988 | Schmidt et al. |
| 4,777,949 A | | 10/1988 | Perlin |
| 4,796,625 A | | 1/1989 | Kees, Jr. |
| 4,799,481 A | | 1/1989 | Transue et al. |
| 4,815,466 A | | 3/1989 | Perlin |
| 4,821,721 A | | 4/1989 | Chin et al. |
| 4,822,348 A | | 4/1989 | Casey |
| 4,834,096 A | | 5/1989 | Oh et al. |
| 4,850,355 A | | 7/1989 | Brooks et al. |
| 4,854,317 A | | 8/1989 | Braun |
| 4,856,517 A | | 8/1989 | Collins et al. |
| 4,929,239 A | | 5/1990 | Braun |
| 4,931,058 A | | 6/1990 | Cooper |
| 4,934,364 A | | 6/1990 | Green |
| 4,951,860 A | | 8/1990 | Peters et al. |
| 4,957,500 A | | 9/1990 | Liang et al. |
| 4,966,603 A | | 10/1990 | Focelle et al. |
| 4,967,949 A | | 11/1990 | Sandhaus |
| 4,983,176 A | | 1/1991 | Cushman et al. |
| 4,988,355 A | | 1/1991 | Leveen et al. |
| 5,002,552 A | | 3/1991 | Casey |
| 5,026,379 A | | 6/1991 | Yoon |
| 5,030,224 A | | 7/1991 | Wright et al. |
| 5,030,226 A | | 7/1991 | Green et al. |
| 5,032,127 A | | 7/1991 | Frazee et al. |
| 5,035,692 A | | 7/1991 | Lyon et al. |
| 5,047,038 A | | 9/1991 | Peters et al. |
| 5,049,152 A | | 9/1991 | Simon et al. |
| 5,049,153 A | | 9/1991 | Nakao et al. |
| 5,053,045 A | | 10/1991 | Schmidt et al. |
| 5,059,202 A | | 10/1991 | Liang et al. |
| 5,062,563 A | | 11/1991 | Green et al. |
| 5,062,846 A | | 11/1991 | Oh et al. |
| 5,078,731 A | | 1/1992 | Hayhurst |
| 5,084,057 A | | 1/1992 | Green et al. |
| 5,100,416 A | | 3/1992 | Oh et al. |
| 5,100,420 A | | 3/1992 | Green et al. |
| 5,104,394 A | | 4/1992 | Knoepfler |
| 5,104,395 A | | 4/1992 | Thornton et al. |
| 5,112,343 A | | 5/1992 | Thornton |
| 5,122,150 A | | 6/1992 | Puig |
| 5,127,915 A | | 7/1992 | Mattson |
| 5,129,885 A | | 7/1992 | Green et al. |
| 5,156,608 A | | 10/1992 | Troidl et al. |
| 5,160,339 A | | 11/1992 | Chen et al. |
| 5,163,945 A | | 11/1992 | Ortiz et al. |
| 5,171,247 A | | 12/1992 | Hughett et al. |
| 5,171,249 A | | 12/1992 | Stefanchik et al. |
| 5,171,250 A | | 12/1992 | Yoon |
| 5,171,251 A | | 12/1992 | Bregen et al. |
| 5,171,252 A | | 12/1992 | Friedland |
| 5,171,253 A | | 12/1992 | Klieman |
| 5,192,288 A | | 3/1993 | Thompson et al. |
| 5,197,970 A | * | 3/1993 | Green .................. A61B 17/128 606/139 |
| 5,199,566 A | | 4/1993 | Ortiz et al. |
| 5,201,746 A | | 4/1993 | Shichman |
| 5,201,900 A | | 4/1993 | Nardella |
| 5,207,691 A | | 5/1993 | Nardella |
| 5,207,692 A | | 5/1993 | Kraus et al. |
| 5,217,473 A | | 6/1993 | Yoon |
| 5,219,353 A | | 6/1993 | Garvey, III et al. |
| 5,246,450 A | | 9/1993 | Thornton et al. |
| 5,269,792 A | | 12/1993 | Kovac et al. |
| 5,281,228 A | | 1/1994 | Wolfson |
| 5,282,807 A | | 2/1994 | Knoepfler |
| 5,282,808 A | | 2/1994 | Kovac et al. |
| 5,282,832 A | | 2/1994 | Toso et al. |
| 5,289,963 A | | 3/1994 | McGarry et al. |
| 5,290,299 A | | 3/1994 | Fain et al. |
| 5,300,081 A | | 4/1994 | Young et al. |
| 5,304,183 A | | 4/1994 | Gourlay et al. |
| 5,306,280 A | | 4/1994 | Bregen et al. |
| 5,306,283 A | | 4/1994 | Conners |
| 5,312,426 A | | 5/1994 | Segawa et al. |
| 5,330,442 A | | 7/1994 | Green et al. |
| 5,330,487 A | | 7/1994 | Thornton et al. |
| 5,340,360 A | | 8/1994 | Stefanchik |
| 5,342,373 A | | 8/1994 | Stefanchik et al. |
| 5,354,304 A | | 10/1994 | Allen et al. |
| 5,354,306 A | | 10/1994 | Garvey, III et al. |
| 5,356,064 A | | 10/1994 | Green et al. |
| 5,366,458 A | | 11/1994 | Korthoff et al. |
| 5,366,459 A | | 11/1994 | Yoon |
| 5,368,600 A | | 11/1994 | Failla et al. |
| 5,381,943 A | | 1/1995 | Allen et al. |
| 5,382,253 A | | 1/1995 | Hogendijk |
| 5,382,254 A | | 1/1995 | McGarry et al. |
| 5,382,255 A | | 1/1995 | Castro et al. |
| 5,383,880 A | | 1/1995 | Hooven |
| 5,383,881 A | | 1/1995 | Green et al. |
| 5,395,375 A | | 3/1995 | Turkel et al. |
| 5,395,381 A | | 3/1995 | Green et al. |
| 5,403,327 A | | 4/1995 | Thornton et al. |
| 5,409,498 A | | 4/1995 | Braddock et al. |
| 5,413,584 A | | 5/1995 | Schulze |

(56) References Cited

U.S. PATENT DOCUMENTS

| | | | |
|---|---|---|---|
| 5,423,835 | A | 6/1995 | Green et al. |
| 5,425,740 | A | 6/1995 | Hutchinson, Jr. |
| 5,431,667 | A | 7/1995 | Thompson et al. |
| 5,431,668 | A | 7/1995 | Burbank, III et al. |
| 5,431,669 | A | 7/1995 | Thompson et al. |
| 5,439,468 | A | 8/1995 | Schulze et al. |
| 5,441,509 | A | 8/1995 | Vidal et al. |
| 5,447,513 | A | 9/1995 | Davison et al. |
| 5,449,365 | A | 9/1995 | Green et al. |
| 5,462,555 | A | 10/1995 | Bolanos et al. |
| 5,462,558 | A | 10/1995 | Kolesa et al. |
| 5,464,416 | A | 11/1995 | Steckel |
| 5,474,566 | A | 12/1995 | Alesi et al. |
| 5,474,567 | A | 12/1995 | Stefanchik et al. |
| 5,474,572 | A | 12/1995 | Hayhurst |
| 5,487,499 | A | 1/1996 | Sorrentino et al. |
| 5,487,746 | A | 1/1996 | Yu et al. |
| 5,501,693 | A | 3/1996 | Gravener |
| 5,509,920 | A | 4/1996 | Phillips et al. |
| 5,514,149 | A | 5/1996 | Green et al. |
| 5,520,701 | A | 5/1996 | Lerch |
| 5,527,318 | A | 6/1996 | McGarry |
| 5,527,319 | A | 6/1996 | Green et al. |
| 5,527,320 | A | 6/1996 | Carruthers et al. |
| 5,542,949 | A | 8/1996 | Yoon |
| 5,547,474 | A | 8/1996 | Kloeckl et al. |
| 5,569,274 | A | 10/1996 | Rapacki et al. |
| 5,571,121 | A | 11/1996 | Heifetz |
| 5,575,802 | A | 11/1996 | McQuilkin et al. |
| 5,582,615 | A | 12/1996 | Foshee et al. |
| 5,584,840 | A | 12/1996 | Ramsey et al. |
| 5,591,178 | A | 1/1997 | Green et al. |
| 5,593,414 | A | 1/1997 | Shipp et al. |
| 5,593,421 | A | 1/1997 | Bauer |
| 5,601,573 | A | 2/1997 | Fogelberg et al. |
| 5,601,574 | A | 2/1997 | Stefanchik et al. |
| 5,607,436 | A | 3/1997 | Pratt et al. |
| 5,618,291 | A | 4/1997 | Thompson et al. |
| 5,618,306 | A | 4/1997 | Roth et al. |
| 5,620,452 | A | 4/1997 | Yoon |
| 5,626,585 | A | 5/1997 | Mittelstadt et al. |
| 5,626,586 | A | 5/1997 | Pistl et al. |
| 5,626,587 | A | 5/1997 | Bishop et al. |
| 5,626,592 | A | 5/1997 | Phillips et al. |
| RE35,525 | E | 6/1997 | Stefanchik et al. |
| 5,634,930 | A | 6/1997 | Thornton et al. |
| 5,643,291 | A | 7/1997 | Pier et al. |
| 5,645,551 | A | 7/1997 | Green et al. |
| 5,645,553 | A | 7/1997 | Kolesa et al. |
| 5,649,937 | A | 7/1997 | Bito et al. |
| 5,653,720 | A | 8/1997 | Johnson et al. |
| 5,662,662 | A | 9/1997 | Bishop et al. |
| 5,662,676 | A | 9/1997 | Koninckx |
| 5,662,679 | A | 9/1997 | Voss et al. |
| 5,665,097 | A | 9/1997 | Baker et al. |
| 5,676,676 | A | 10/1997 | Porter |
| 5,681,330 | A | 10/1997 | Hughett et al. |
| 5,683,405 | A | 11/1997 | Yacoubian et al. |
| 5,695,502 | A | 12/1997 | Pier et al. |
| 5,695,505 | A | 12/1997 | Yoon |
| 5,697,938 | A | 12/1997 | Jensen et al. |
| 5,700,270 | A | 12/1997 | Peyser et al. |
| 5,700,271 | A | 12/1997 | Whitfield et al. |
| 5,702,048 | A | 12/1997 | Eberlin |
| 5,709,706 | A | 1/1998 | Kienzle et al. |
| 5,713,911 | A | 2/1998 | Racenet et al. |
| 5,713,912 | A | 2/1998 | Porter |
| 5,720,756 | A | 2/1998 | Green et al. |
| 5,722,982 | A | 3/1998 | Ferreira et al. |
| 5,725,537 | A | 3/1998 | Green et al. |
| 5,725,538 | A | 3/1998 | Green et al. |
| 5,725,542 | A | 3/1998 | Yoon |
| 5,733,295 | A | 3/1998 | Back et al. |
| 5,749,881 | A | 5/1998 | Sackier et al. |
| 5,755,726 | A | 5/1998 | Pratt et al. |
| 5,766,189 | A | 6/1998 | Matsuno |
| 5,769,857 | A | 6/1998 | Reztzov et al. |
| 5,772,673 | A | 6/1998 | Cuny et al. |
| 5,776,146 | A | 7/1998 | Sackier et al. |
| 5,776,147 | A | 7/1998 | Dolendo |
| 5,779,718 | A | 7/1998 | Green et al. |
| 5,779,720 | A | 7/1998 | Walder-Utz et al. |
| 5,782,844 | A | 7/1998 | Yoon et al. |
| 5,788,698 | A | 8/1998 | Savornin |
| 5,792,149 | A | 8/1998 | Sherts et al. |
| 5,792,150 | A | 8/1998 | Pratt et al. |
| 5,797,922 | A | 8/1998 | Hessel et al. |
| 5,810,853 | A | 9/1998 | Yoon |
| 5,817,116 | A | 10/1998 | Takahashi et al. |
| 5,827,279 | A | 10/1998 | Hughett et al. |
| 5,827,306 | A | 10/1998 | Yoon |
| 5,827,323 | A | 10/1998 | Klieman et al. |
| 5,833,695 | A | 11/1998 | Yoon |
| 5,833,696 | A | 11/1998 | Whitfield et al. |
| 5,833,700 | A | 11/1998 | Fogelberg et al. |
| 5,835,199 | A | 11/1998 | Phillips et al. |
| 5,843,097 | A | 12/1998 | Mayenberger et al. |
| 5,843,101 | A | 12/1998 | Fry |
| 5,846,255 | A | 12/1998 | Casey |
| 5,849,019 | A | 12/1998 | Yoon |
| 5,858,018 | A | 1/1999 | Shipp et al. |
| 5,861,005 | A | 1/1999 | Kontos |
| 5,868,759 | A | 2/1999 | Peyser et al. |
| 5,868,761 | A | 2/1999 | Nicholas et al. |
| 5,876,410 | A | 3/1999 | Petillo |
| 5,895,394 | A | 4/1999 | Kienzle et al. |
| 5,897,565 | A | 4/1999 | Foster |
| 5,904,693 | A | 5/1999 | Dicesare et al. |
| 5,906,625 | A | 5/1999 | Bito et al. |
| 5,913,862 | A | 6/1999 | Ramsey et al. |
| 5,918,791 | A | 7/1999 | Sorrentino et al. |
| 5,921,996 | A | 7/1999 | Sherman |
| 5,921,997 | A | 7/1999 | Fogelberg et al. |
| 5,928,251 | A | 7/1999 | Aranyi et al. |
| 5,938,667 | A | 8/1999 | Peyser et al. |
| 5,951,574 | A | 9/1999 | Stefanchik et al. |
| 5,972,003 | A | 10/1999 | Rousseau et al. |
| 5,976,159 | A | 11/1999 | Bolduc et al. |
| 5,993,465 | A | 11/1999 | Shipp et al. |
| 6,004,335 | A | 12/1999 | Vaitekunas et al. |
| 6,009,551 | A | 12/1999 | Sheynblat |
| 6,017,358 | A | 1/2000 | Yoon et al. |
| 6,053,908 | A | 4/2000 | Crainich et al. |
| RE36,720 | E | 5/2000 | Green et al. |
| 6,059,799 | A | 5/2000 | Aranyi et al. |
| 6,099,536 | A | 8/2000 | Petillo |
| 6,099,537 | A | 8/2000 | Sugai et al. |
| 6,139,555 | A | 10/2000 | Hart et al. |
| 6,210,418 | B1 | 4/2001 | Storz et al. |
| 6,217,590 | B1 | 4/2001 | Levinson |
| 6,228,097 | B1 | 5/2001 | Levinson et al. |
| 6,241,740 | B1 | 6/2001 | Davis et al. |
| 6,258,105 | B1 | 7/2001 | Hart et al. |
| 6,261,302 | B1 | 7/2001 | Voegele et al. |
| 6,273,898 | B1 | 8/2001 | Kienzle et al. |
| 6,277,131 | B1 | 8/2001 | Kalikow |
| 6,306,149 | B1 | 10/2001 | Meade |
| 6,318,619 | B1 | 11/2001 | Lee |
| 6,322,571 | B1 | 11/2001 | Adams |
| 6,350,269 | B1 | 2/2002 | Shipp et al. |
| 6,352,541 | B1 | 3/2002 | Kienzle et al. |
| 6,391,035 | B1 | 5/2002 | Appleby et al. |
| 6,423,079 | B1 | 7/2002 | Blake, III |
| 6,428,548 | B1 | 8/2002 | Durgin et al. |
| 6,440,144 | B1 | 8/2002 | Bacher |
| 6,461,363 | B1 | 10/2002 | Gadberry et al. |
| 6,464,710 | B1 | 10/2002 | Foster |
| 6,494,886 | B1 | 12/2002 | Wilk et al. |
| 6,517,536 | B2 | 2/2003 | Hooven et al. |
| 6,520,972 | B2 | 2/2003 | Peters |
| 6,527,786 | B1 | 3/2003 | Davis et al. |
| 6,537,289 | B1 | 3/2003 | Kayan et al. |
| 6,546,935 | B2 | 4/2003 | Hooven |
| 6,551,333 | B2 | 4/2003 | Kuhns et al. |

(56) References Cited

U.S. PATENT DOCUMENTS

| | | | |
|---|---|---|---|
| 6,562,051 | B1 | 5/2003 | Bolduc et al. |
| 6,569,171 | B2 | 5/2003 | DeGuillebon et al. |
| 6,579,304 | B1 | 6/2003 | Hart et al. |
| 6,599,298 | B1 | 7/2003 | Forster et al. |
| 6,602,252 | B2 | 8/2003 | Mollenauer |
| 6,607,540 | B1 | 8/2003 | Shipp |
| 6,613,060 | B2 | 9/2003 | Adams et al. |
| 6,626,916 | B1 | 9/2003 | Yeung et al. |
| 6,626,922 | B1 | 9/2003 | Hart et al. |
| 6,648,898 | B1 | 11/2003 | Baxter |
| 6,652,538 | B2 | 11/2003 | Kayan et al. |
| 6,652,539 | B2 | 11/2003 | Shipp et al. |
| 6,656,193 | B2 | 12/2003 | Grant et al. |
| 6,673,083 | B1 | 1/2004 | Kayan et al. |
| 6,676,659 | B2 | 1/2004 | Hutchins et al. |
| 6,679,894 | B2 | 1/2004 | Damarati |
| RE38,445 | E | 2/2004 | Pistl et al. |
| 6,695,854 | B1 | 2/2004 | Kayan et al. |
| 6,706,057 | B1 | 3/2004 | Bidoia et al. |
| 6,716,226 | B2 | 4/2004 | Sixto, Jr. et al. |
| 6,723,109 | B2 | 4/2004 | Solingen |
| 6,743,240 | B2 | 6/2004 | Smith et al. |
| 6,773,438 | B1 | 8/2004 | Knodel et al. |
| 6,773,440 | B2 | 8/2004 | Gannoe et al. |
| 6,776,783 | B1 | 8/2004 | Frantzen et al. |
| 6,776,784 | B2 | 8/2004 | Ginn |
| 6,780,195 | B2 | 8/2004 | Porat |
| 6,793,663 | B2 | 9/2004 | Kneifel et al. |
| 6,793,664 | B2 | 9/2004 | Mazzocchi et al. |
| 6,802,848 | B2 | 10/2004 | Anderson et al. |
| 6,814,742 | B2 | 11/2004 | Kimura et al. |
| 6,818,009 | B2 | 11/2004 | Hart et al. |
| 6,821,273 | B2 | 11/2004 | Mollenauer |
| 6,821,284 | B2 | 11/2004 | Sturtz et al. |
| 6,824,547 | B2 | 11/2004 | Wilson, Jr. et al. |
| 6,824,548 | B2 | 11/2004 | Smith et al. |
| 6,835,199 | B2 | 12/2004 | McGuckin, Jr. et al. |
| 6,835,200 | B2 | 12/2004 | Laufer et al. |
| 6,837,893 | B2 | 1/2005 | Miller |
| 6,837,894 | B2 | 1/2005 | Pugsley, Jr. et al. |
| 6,837,895 | B2 | 1/2005 | Mayenberger |
| 6,840,945 | B2 | 1/2005 | Manetakis et al. |
| 6,843,794 | B2 | 1/2005 | Sixto, Jr. et al. |
| 6,849,078 | B2 | 2/2005 | Durgin et al. |
| 6,849,079 | B1 | 2/2005 | Blake, III et al. |
| 6,853,879 | B2 | 2/2005 | Sunaoshi |
| 6,869,435 | B2 | 3/2005 | Blake, III |
| 6,869,436 | B2 | 3/2005 | Wendlandt |
| 6,889,116 | B2 | 5/2005 | Jinno |
| 6,896,682 | B1 | 5/2005 | McClellan et al. |
| 6,905,503 | B2 | 6/2005 | Gifford, III et al. |
| 6,911,032 | B2 | 6/2005 | Jugenheimer et al. |
| 6,911,033 | B2 | 6/2005 | de Guillebon et al. |
| 6,913,607 | B2 | 7/2005 | Ainsworth et al. |
| 6,916,327 | B2 | 7/2005 | Northrup, III et al. |
| 6,923,818 | B2 | 8/2005 | Muramatsu et al. |
| 6,939,356 | B2 | 9/2005 | Debbas |
| 6,942,674 | B2 | 9/2005 | Belef et al. |
| 6,942,676 | B2 | 9/2005 | Buelna |
| 6,945,978 | B1 | 9/2005 | Hyde |
| 6,945,979 | B2 | 9/2005 | Kortenbach et al. |
| 6,949,107 | B2 | 9/2005 | McGuckin, Jr. et al. |
| 6,953,465 | B2 | 10/2005 | Dieck et al. |
| 6,955,643 | B2 | 10/2005 | Gellman et al. |
| 6,959,852 | B2 | 11/2005 | Shelton, IV et al. |
| 6,960,218 | B2 | 11/2005 | Rennich |
| 6,960,221 | B2 | 11/2005 | Ho et al. |
| 6,962,594 | B1 | 11/2005 | Thevenet |
| 6,963,792 | B1 | 11/2005 | Green |
| 6,964,363 | B2 | 11/2005 | Wales et al. |
| 6,964,668 | B2 | 11/2005 | Modesitt et al. |
| 6,966,875 | B1 | 11/2005 | Longobardi |
| 6,966,917 | B1 | 11/2005 | Suyker et al. |
| 6,966,919 | B2 | 11/2005 | Sixto, Jr. et al. |
| 6,969,391 | B1 | 11/2005 | Gazzani |
| 6,972,023 | B2 | 12/2005 | Whayne et al. |
| 6,972,027 | B2 | 12/2005 | Fallin et al. |
| 6,973,770 | B2 | 12/2005 | Schnipke et al. |
| 6,974,462 | B2 | 12/2005 | Sater |
| 6,974,466 | B2 | 12/2005 | Ahmed et al. |
| 6,974,475 | B1 | 12/2005 | Wall |
| 6,981,505 | B2 | 1/2006 | Krause et al. |
| 6,981,628 | B2 | 1/2006 | Wales |
| 6,991,635 | B2 | 1/2006 | Takamoto et al. |
| 7,052,504 | B2 | 5/2006 | Hughett |
| 7,056,330 | B2 | 6/2006 | Gayton |
| 7,108,703 | B2 | 9/2006 | Danitz et al. |
| 7,144,402 | B2 | 12/2006 | Kuester, III |
| 7,175,648 | B2 | 2/2007 | Nakao |
| 7,179,265 | B2 | 2/2007 | Manetakis et al. |
| 7,207,997 | B2 | 4/2007 | Shipp et al. |
| 7,211,091 | B2 | 5/2007 | Fowler et al. |
| 7,211,092 | B2 | 5/2007 | Hughett |
| 7,214,230 | B2 | 5/2007 | Brock et al. |
| 7,214,232 | B2 | 5/2007 | Bowman et al. |
| 7,223,271 | B2 | 5/2007 | Muramatsu et al. |
| 7,232,445 | B2 | 6/2007 | Kortenbach et al. |
| 7,261,724 | B2 | 8/2007 | Molitor et al. |
| 7,261,725 | B2 | 8/2007 | Binmoeller |
| 7,264,625 | B1 | 9/2007 | Buncke |
| 7,288,098 | B2 | 10/2007 | Huitema et al. |
| 7,297,149 | B2 | 11/2007 | Vitali et al. |
| 7,316,693 | B2 | 1/2008 | Viola |
| 7,316,696 | B2 | 1/2008 | Wilson, Jr. et al. |
| 7,326,223 | B2 | 2/2008 | Wilson, Jr. |
| 7,329,266 | B2 | 2/2008 | Royse et al. |
| 7,331,968 | B2 | 2/2008 | Arp et al. |
| 7,338,503 | B2 | 3/2008 | Rosenberg et al. |
| 7,357,805 | B2 | 4/2008 | Masuda et al. |
| 7,510,562 | B2 | 3/2009 | Lindsay |
| 7,552,853 | B2 | 6/2009 | Mas et al. |
| 7,637,917 | B2 | 12/2009 | Whitfield et al. |
| 7,644,848 | B2 | 1/2010 | Swayze et al. |
| 7,686,820 | B2 | 3/2010 | Huitema et al. |
| 7,695,482 | B2 | 4/2010 | Viola |
| 7,717,926 | B2 | 5/2010 | Whitfield et al. |
| 7,727,248 | B2 | 6/2010 | Smith et al. |
| 7,731,724 | B2 | 6/2010 | Huitema et al. |
| 7,740,641 | B2 | 6/2010 | Huitema |
| 7,752,853 | B2 | 7/2010 | Singh et al. |
| 7,753,250 | B2 | 7/2010 | Clauson et al. |
| 7,766,207 | B2 | 8/2010 | Mather et al. |
| 7,819,886 | B2 | 10/2010 | Whitfield et al. |
| 7,887,553 | B2 | 2/2011 | Lehman et al. |
| 7,905,890 | B2 | 3/2011 | Whitfield et al. |
| 7,942,885 | B2 | 5/2011 | Sixto, Jr. et al. |
| 7,952,060 | B2 | 5/2011 | Watanabe et al. |
| 7,963,433 | B2 | 6/2011 | Whitman et al. |
| 7,988,027 | B2 | 8/2011 | Olson et al. |
| 8,011,550 | B2 | 9/2011 | Aranyi et al. |
| 8,011,555 | B2 | 9/2011 | Tarinelli et al. |
| 8,016,178 | B2 | 9/2011 | Olson et al. |
| 8,021,375 | B2 | 9/2011 | Aldrich et al. |
| 8,021,378 | B2 | 9/2011 | Sixto, Jr. et al. |
| 8,038,686 | B2 | 10/2011 | Huitema et al. |
| 8,056,565 | B2 | 11/2011 | Zergiebel |
| 8,062,310 | B2 | 11/2011 | Shibata et al. |
| 8,066,720 | B2 | 11/2011 | Knodel et al. |
| 8,066,721 | B2 | 11/2011 | Kortenbach et al. |
| 8,066,722 | B2 | 11/2011 | Miyagi et al. |
| 8,070,760 | B2 | 12/2011 | Fujita |
| 8,075,571 | B2 | 12/2011 | Vitali et al. |
| 8,080,021 | B2 | 12/2011 | Griego |
| 8,083,668 | B2 | 12/2011 | Durgin et al. |
| 8,088,061 | B2 | 1/2012 | Wells et al. |
| 8,091,755 | B2 | 1/2012 | Kayan et al. |
| 8,100,926 | B1 | 1/2012 | Filshie et al. |
| 8,128,643 | B2 | 3/2012 | Aranyi et al. |
| 8,133,240 | B2 | 3/2012 | Damarati |
| 8,142,451 | B2 | 3/2012 | Boulnois et al. |
| 8,157,145 | B2 | 4/2012 | Shelton, IV et al. |
| 8,157,149 | B2 | 4/2012 | Olson et al. |
| 8,157,151 | B2 | 4/2012 | Ingmanson et al. |
| 8,172,859 | B2 | 5/2012 | Matsuno et al. |

(56) References Cited

U.S. PATENT DOCUMENTS

| | | | |
|---|---|---|---|
| 8,172,870 | B2 | 5/2012 | Shipp |
| 8,187,290 | B2 | 5/2012 | Buckman et al. |
| 8,211,120 | B2 | 7/2012 | Itoh |
| 8,211,124 | B2 | 7/2012 | Ainsworth et al. |
| 8,216,255 | B2 | 7/2012 | Smith et al. |
| 8,216,257 | B2 | 7/2012 | Huitema et al. |
| 8,236,012 | B2 | 8/2012 | Molitor et al. |
| 8,246,634 | B2 | 8/2012 | Huitema et al. |
| 8,246,635 | B2 | 8/2012 | Huitema |
| 8,262,678 | B2 | 9/2012 | Matsuoka et al. |
| 8,262,679 | B2 | 9/2012 | Nguyen |
| 8,267,944 | B2 | 9/2012 | Sorrentino et al. |
| 8,267,945 | B2 | 9/2012 | Nguyen et al. |
| 8,267,946 | B2 | 9/2012 | Whitfield et al. |
| 8,272,554 | B2 | 9/2012 | Whitman et al. |
| 8,282,655 | B2 | 10/2012 | Whitfield et al. |
| 8,308,743 | B2 | 11/2012 | Matsuno et al. |
| 8,328,822 | B2 | 12/2012 | Huitema et al. |
| 8,336,556 | B2 | 12/2012 | Zergiebel |
| 8,348,130 | B2 | 1/2013 | Shah et al. |
| 8,357,171 | B2 | 1/2013 | Whitfield et al. |
| 8,366,709 | B2 | 2/2013 | Schechter et al. |
| 8,366,726 | B2 | 2/2013 | Dennis |
| 8,371,491 | B2 | 2/2013 | Huitema et al. |
| 8,372,095 | B2 | 2/2013 | Viola |
| 8,382,773 | B2 | 2/2013 | Whitfield et al. |
| 8,398,655 | B2 | 3/2013 | Cheng et al. |
| 8,403,945 | B2 | 3/2013 | Whitfield et al. |
| 8,403,946 | B2 | 3/2013 | Whitfield et al. |
| 8,408,442 | B2 | 4/2013 | Racenet et al. |
| 8,409,222 | B2 | 4/2013 | Whitfield et al. |
| 8,409,223 | B2 | 4/2013 | Sorrentino et al. |
| 8,419,752 | B2 | 4/2013 | Sorrentino et al. |
| 8,430,892 | B2 | 4/2013 | Bindra et al. |
| 8,444,660 | B2 | 5/2013 | Adams et al. |
| 8,465,460 | B2 | 6/2013 | Yodfat et al. |
| 8,465,502 | B2 | 6/2013 | Zergiebel |
| 8,475,473 | B2 | 7/2013 | Vandenbroek et al. |
| 8,480,688 | B2 | 7/2013 | Boulnois et al. |
| 8,486,091 | B2 | 7/2013 | Sorrentino et al. |
| 8,491,608 | B2 | 7/2013 | Sorrentino et al. |
| 8,496,673 | B2 | 7/2013 | Nguyen et al. |
| 8,506,580 | B2 | 8/2013 | Zergiebel et al. |
| 8,512,357 | B2 | 8/2013 | Viola |
| 8,518,055 | B1 | 8/2013 | Cardinale et al. |
| 8,523,882 | B2 | 9/2013 | Huitema et al. |
| 8,529,585 | B2 | 9/2013 | Jacobs et al. |
| 8,529,586 | B2 | 9/2013 | Rosenberg et al. |
| 8,529,588 | B2 | 9/2013 | Ahlberg et al. |
| 8,545,486 | B2 | 10/2013 | Malkowski |
| 8,556,920 | B2 | 10/2013 | Huitema et al. |
| 8,568,430 | B2 | 10/2013 | Shipp |
| 8,579,918 | B2 | 11/2013 | Whitfield et al. |
| 8,585,717 | B2 | 11/2013 | Sorrentino et al. |
| 8,603,109 | B2 | 12/2013 | Aranyi et al. |
| 8,652,151 | B2 | 2/2014 | Lehman et al. |
| 8,652,152 | B2 | 2/2014 | Aranyi et al. |
| 8,663,247 | B2 | 3/2014 | Menn et al. |
| 8,685,048 | B2 | 4/2014 | Adams et al. |
| 8,690,899 | B2 | 4/2014 | Kogiso et al. |
| 8,708,213 | B2 | 4/2014 | Shelton, IV et al. |
| 8,709,027 | B2 | 4/2014 | Adams et al. |
| 8,715,299 | B2 | 5/2014 | Menn et al. |
| 8,720,766 | B2 | 5/2014 | Hess et al. |
| 8,734,469 | B2 | 5/2014 | Pribanic et al. |
| 8,747,423 | B2 | 6/2014 | Whitfield et al. |
| 8,753,356 | B2 | 6/2014 | Vitali et al. |
| 8,814,884 | B2 | 8/2014 | Whitfield et al. |
| 8,821,516 | B2 | 9/2014 | Huitema |
| 8,839,954 | B2 | 9/2014 | Disch |
| 8,845,659 | B2 | 9/2014 | Whitfield et al. |
| 8,894,665 | B2 | 11/2014 | Sorrentino et al. |
| 8,894,666 | B2 | 11/2014 | Schulz et al. |
| 8,900,253 | B2 | 12/2014 | Aranyi et al. |
| 8,915,930 | B2 | 12/2014 | Huitema et al. |
| 8,920,438 | B2 | 12/2014 | Aranyi et al. |
| 8,950,646 | B2 | 2/2015 | Viola |
| 8,961,542 | B2 | 2/2015 | Whitfield et al. |
| 8,968,337 | B2 | 3/2015 | Whitfield et al. |
| 8,968,342 | B2 | 3/2015 | Wingardner, III et al. |
| 8,973,804 | B2 | 3/2015 | Hess et al. |
| 9,011,464 | B2 | 4/2015 | Zammataro |
| 9,011,465 | B2 | 4/2015 | Whitfield et al. |
| 9,089,334 | B2 | 7/2015 | Sorrentino et al. |
| 9,113,892 | B2 | 8/2015 | Malkowski et al. |
| 9,113,893 | B2 | 8/2015 | Sorrentino et al. |
| 9,119,629 | B2 | 9/2015 | Cardinale et al. |
| 9,186,136 | B2 | 11/2015 | Malkowski et al. |
| 9,186,153 | B2 | 11/2015 | Zammataro |
| 9,208,429 | B2 | 12/2015 | Thornton et al. |
| 9,282,961 | B2 | 3/2016 | Whitman et al. |
| 9,326,776 | B2 | 5/2016 | Gadberry et al. |
| 9,358,011 | B2 | 6/2016 | Sorrentino et al. |
| 9,358,015 | B2 | 6/2016 | Sorrentino et al. |
| 9,364,216 | B2 | 6/2016 | Rockrohr et al. |
| 9,364,239 | B2 | 6/2016 | Malkowski |
| 9,364,240 | B2 | 6/2016 | Whitfield et al. |
| 9,370,400 | B2 | 6/2016 | Parihar |
| 9,393,024 | B2 | 7/2016 | Whitfield et al. |
| 9,398,917 | B2 | 7/2016 | Whitfield et al. |
| 9,408,610 | B2 | 8/2016 | Hartoumbekis |
| 9,414,844 | B2 | 8/2016 | Zergiebel et al. |
| 9,433,411 | B2 | 9/2016 | Racenet et al. |
| 9,439,654 | B2 | 9/2016 | Sorrentino et al. |
| 9,480,477 | B2 | 11/2016 | Aranyi et al. |
| 9,526,501 | B2 | 12/2016 | Malkowski |
| 9,532,787 | B2 | 1/2017 | Zammataro |
| 9,545,254 | B2 | 1/2017 | Sorrentino et al. |
| 9,549,741 | B2 | 1/2017 | Zergiebel |
| 2001/0047178 | A1 | 11/2001 | Peters |
| 2002/0040226 | A1 | 4/2002 | Laufer et al. |
| 2002/0068947 | A1 | 6/2002 | Kuhns et al. |
| 2002/0082618 | A1 | 6/2002 | Shipp et al. |
| 2002/0087169 | A1 | 7/2002 | Brock et al. |
| 2002/0087170 | A1 | 7/2002 | Kuhns et al. |
| 2002/0099388 | A1 | 7/2002 | Mayenberger |
| 2002/0120279 | A1 | 8/2002 | Deguillebon et al. |
| 2002/0128668 | A1* | 9/2002 | Manetakis ......... A61B 17/1285 606/143 |
| 2002/0177859 | A1 | 11/2002 | Monassevitch et al. |
| 2002/0198537 | A1 | 12/2002 | Smith et al. |
| 2002/0198538 | A1 | 12/2002 | Kortenbach et al. |
| 2002/0198539 | A1 | 12/2002 | Sixto et al. |
| 2002/0198540 | A1 | 12/2002 | Smith et al. |
| 2002/0198541 | A1 | 12/2002 | Smith et al. |
| 2003/0014060 | A1 | 1/2003 | Wilson et al. |
| 2003/0018345 | A1 | 1/2003 | Green |
| 2003/0023249 | A1 | 1/2003 | Manetakis |
| 2003/0040759 | A1 | 2/2003 | de Guillebon et al. |
| 2003/0105476 | A1 | 6/2003 | Sancoff et al. |
| 2003/0114867 | A1 | 6/2003 | Bolduc et al. |
| 2003/0135224 | A1 | 7/2003 | Blake |
| 2003/0167063 | A1 | 9/2003 | Kerr |
| 2003/0208231 | A1 | 11/2003 | Williamson et al. |
| 2003/0220657 | A1 | 11/2003 | Adams |
| 2003/0225423 | A1 | 12/2003 | Huitema |
| 2003/0229360 | A1 | 12/2003 | Gayton |
| 2003/0233105 | A1 | 12/2003 | Gayton |
| 2004/0010272 | A1 | 1/2004 | Manetakis et al. |
| 2004/0044352 | A1 | 3/2004 | Fowler et al. |
| 2004/0097970 | A1 | 5/2004 | Hughett |
| 2004/0097971 | A1 | 5/2004 | Hughett |
| 2004/0097972 | A1 | 5/2004 | Shipp et al. |
| 2004/0106936 | A1 | 6/2004 | Shipp et al. |
| 2004/0133215 | A1 | 7/2004 | Baxter |
| 2004/0138681 | A1 | 7/2004 | Pier |
| 2004/0153100 | A1 | 8/2004 | Ahlberg et al. |
| 2004/0158266 | A1 | 8/2004 | Damarati |
| 2004/0162567 | A9 | 8/2004 | Adams |
| 2004/0167545 | A1 | 8/2004 | Sadler et al. |
| 2004/0176776 | A1 | 9/2004 | Zubok et al. |
| 2004/0176783 | A1 | 9/2004 | Edoga et al. |
| 2004/0176784 | A1 | 9/2004 | Okada |
| 2004/0193213 | A1 | 9/2004 | Aranyi et al. |

(56) References Cited

U.S. PATENT DOCUMENTS

| | | | |
|---|---|---|---|
| 2005/0080440 | A1 | 4/2005 | Durgin et al. |
| 2005/0090837 | A1 | 4/2005 | Sixto et al. |
| 2005/0090838 | A1 | 4/2005 | Sixto et al. |
| 2005/0096670 | A1 | 5/2005 | Wellman et al. |
| 2005/0096671 | A1 | 5/2005 | Wellman et al. |
| 2005/0096672 | A1 | 5/2005 | Manetakis et al. |
| 2005/0101975 | A1 | 5/2005 | Nguyen et al. |
| 2005/0107807 | A1 | 5/2005 | Nakao |
| 2005/0107809 | A1 | 5/2005 | Litscher et al. |
| 2005/0107810 | A1 | 5/2005 | Morales et al. |
| 2005/0107811 | A1 | 5/2005 | Starksen et al. |
| 2005/0107812 | A1 | 5/2005 | Starksen et al. |
| 2005/0107871 | A1 | 5/2005 | Realyvasquez et al. |
| 2005/0113847 | A1 | 5/2005 | Gadberry et al. |
| 2005/0119671 | A1 | 6/2005 | Reydel et al. |
| 2005/0119673 | A1 | 6/2005 | Gordon et al. |
| 2005/0119677 | A1 | 6/2005 | Shipp |
| 2005/0125010 | A1 | 6/2005 | Smith et al. |
| 2005/0143767 | A1 | 6/2005 | Kimura et al. |
| 2005/0149063 | A1 | 7/2005 | Young et al. |
| 2005/0149064 | A1 | 7/2005 | Peterson et al. |
| 2005/0149068 | A1 | 7/2005 | Williams et al. |
| 2005/0149069 | A1 | 7/2005 | Bertolero et al. |
| 2005/0165415 | A1 | 7/2005 | Wales |
| 2005/0165418 | A1 | 7/2005 | Chan |
| 2005/0171560 | A1 | 8/2005 | Hughett |
| 2005/0175703 | A1 | 8/2005 | Hunter et al. |
| 2005/0177176 | A1 | 8/2005 | Gerbi et al. |
| 2005/0203547 | A1 | 9/2005 | Weller et al. |
| 2005/0203548 | A1 | 9/2005 | Weller et al. |
| 2005/0216036 | A1 | 9/2005 | Nakao |
| 2005/0216056 | A1 | 9/2005 | Valdevit et al. |
| 2005/0222588 | A1 | 10/2005 | Vandenbroek et al. |
| 2005/0222590 | A1 | 10/2005 | Gadberry et al. |
| 2005/0222665 | A1 | 10/2005 | Aranyi |
| 2005/0228411 | A1 | 10/2005 | Manzo |
| 2005/0228416 | A1 | 10/2005 | Burbank et al. |
| 2005/0234478 | A1 | 10/2005 | Wixey et al. |
| 2005/0251183 | A1 | 11/2005 | Buckman et al. |
| 2005/0251184 | A1 | 11/2005 | Anderson |
| 2005/0256529 | A1 | 11/2005 | Yawata et al. |
| 2005/0267495 | A1 | 12/2005 | Ginn et al. |
| 2005/0273122 | A1 | 12/2005 | Theroux et al. |
| 2005/0277951 | A1 | 12/2005 | Smith et al. |
| 2005/0277952 | A1 | 12/2005 | Arp et al. |
| 2005/0277953 | A1 | 12/2005 | Francese et al. |
| 2005/0277954 | A1 | 12/2005 | Smith et al. |
| 2005/0277955 | A1 | 12/2005 | Palmer et al. |
| 2005/0277956 | A1 | 12/2005 | Francese et al. |
| 2005/0277958 | A1 | 12/2005 | Levinson |
| 2005/0288689 | A1 | 12/2005 | Kammerer et al. |
| 2005/0288690 | A1 | 12/2005 | Bourque et al. |
| 2006/0004388 | A1 | 1/2006 | Whayne et al. |
| 2006/0004390 | A1 | 1/2006 | Rosenberg et al. |
| 2006/0009789 | A1 | 1/2006 | Gambale et al. |
| 2006/0009790 | A1 | 1/2006 | Blake et al. |
| 2006/0009792 | A1 | 1/2006 | Baker et al. |
| 2006/0020270 | A1 | 1/2006 | Jabba et al. |
| 2006/0020271 | A1 | 1/2006 | Stewart et al. |
| 2006/0047305 | A1 | 3/2006 | Ortiz et al. |
| 2006/0047306 | A1 | 3/2006 | Ortiz et al. |
| 2006/0064117 | A1 | 3/2006 | Aranyi et al. |
| 2006/0079115 | A1 | 4/2006 | Aranyi et al. |
| 2006/0079913 | A1 | 4/2006 | Whitfield et al. |
| 2006/0100649 | A1 | 5/2006 | Hart |
| 2006/0111731 | A1 | 5/2006 | Manzo |
| 2006/0129170 | A1 | 6/2006 | Royce et al. |
| 2006/0135992 | A1 | 6/2006 | Bettuchi et al. |
| 2006/0163312 | A1 | 7/2006 | Viola et al. |
| 2006/0173470 | A1 | 8/2006 | Oray et al. |
| 2006/0178683 | A1 | 8/2006 | Shimoji et al. |
| 2006/0184182 | A1 | 8/2006 | Aranyi et al. |
| 2006/0190013 | A1 | 8/2006 | Menn |
| 2006/0195125 | A1 | 8/2006 | Sakakine et al. |
| 2006/0200179 | A1 | 9/2006 | Barker et al. |
| 2006/0212050 | A1 | 9/2006 | D'Agostino et al. |
| 2006/0217749 | A1 | 9/2006 | Wilson et al. |
| 2006/0224165 | A1 | 10/2006 | Surti et al. |
| 2006/0224170 | A1 | 10/2006 | Duff |
| 2006/0235437 | A1 | 10/2006 | Vitali et al. |
| 2006/0235438 | A1 | 10/2006 | Huitema et al. |
| 2006/0235439 | A1 | 10/2006 | Molitor et al. |
| 2006/0235440 | A1 | 10/2006 | Huitema et al. |
| 2006/0235441 | A1 | 10/2006 | Huitema et al. |
| 2006/0235442 | A1 | 10/2006 | Huitema |
| 2006/0235443 | A1 | 10/2006 | Huitema et al. |
| 2006/0235444 | A1 | 10/2006 | Huitema et al. |
| 2006/0259045 | A1 | 11/2006 | Damarati |
| 2006/0259049 | A1 | 11/2006 | Harada et al. |
| 2006/0264987 | A1 | 11/2006 | Sgro |
| 2006/0271072 | A1 | 11/2006 | Hummel et al. |
| 2007/0016228 | A1 | 1/2007 | Salas |
| 2007/0021761 | A1 | 1/2007 | Phillips |
| 2007/0023476 | A1 | 2/2007 | Whitman et al. |
| 2007/0023477 | A1 | 2/2007 | Whitman et al. |
| 2007/0027458 | A1 | 2/2007 | Sixto, Jr. et al. |
| 2007/0034669 | A1 | 2/2007 | de la Torre et al. |
| 2007/0038233 | A1 | 2/2007 | Martinez et al. |
| 2007/0049947 | A1 | 3/2007 | Menn et al. |
| 2007/0049948 | A1 | 3/2007 | Menn et al. |
| 2007/0049949 | A1 | 3/2007 | Manetakis |
| 2007/0049950 | A1 | 3/2007 | Theroux et al. |
| 2007/0049951 | A1 | 3/2007 | Menn |
| 2007/0049953 | A2 | 3/2007 | Shimoji et al. |
| 2007/0066981 | A1 | 3/2007 | Meagher |
| 2007/0073314 | A1 | 3/2007 | Gadberry et al. |
| 2007/0083218 | A1 | 4/2007 | Morris |
| 2007/0093856 | A1 | 4/2007 | Whitfield et al. |
| 2007/0106314 | A1 | 5/2007 | Dunn |
| 2007/0112365 | A1 | 5/2007 | Hilal et al. |
| 2007/0118155 | A1 | 5/2007 | Goldfarb et al. |
| 2007/0118161 | A1 | 5/2007 | Kennedy et al. |
| 2007/0118163 | A1 | 5/2007 | Boudreaux et al. |
| 2007/0118174 | A1 | 5/2007 | Chu |
| 2007/0123916 | A1 | 5/2007 | Maier et al. |
| 2007/0142848 | A1 | 6/2007 | Ainsworth et al. |
| 2007/0142851 | A1 | 6/2007 | Sixto et al. |
| 2007/0149988 | A1 | 6/2007 | Michler et al. |
| 2007/0149989 | A1 | 6/2007 | Santilli et al. |
| 2007/0162060 | A1 | 7/2007 | Wild |
| 2007/0173866 | A1 | 7/2007 | Sorrentino et al. |
| 2007/0175949 | A1 | 8/2007 | Shelton et al. |
| 2007/0185504 | A1 | 8/2007 | Manetakis et al. |
| 2007/0191868 | A1 | 8/2007 | Theroux et al. |
| 2007/0203509 | A1 | 8/2007 | Bettuchi |
| 2007/0203510 | A1 | 8/2007 | Bettuchi |
| 2007/0213747 | A1 | 9/2007 | Monassevitch et al. |
| 2007/0250080 | A1 | 10/2007 | Jones et al. |
| 2007/0265640 | A1 | 11/2007 | Kortenbach et al. |
| 2007/0276417 | A1 | 11/2007 | Mendes, Jr. et al. |
| 2007/0282355 | A1 | 12/2007 | Brown et al. |
| 2007/0288039 | A1 | 12/2007 | Aranyi et al. |
| 2007/0293875 | A1 | 12/2007 | Soetikno et al. |
| 2008/0004636 | A1 | 1/2008 | Walberg et al. |
| 2008/0004637 | A1 | 1/2008 | Klassen et al. |
| 2008/0004639 | A1 | 1/2008 | Huitema et al. |
| 2008/0015615 | A1 | 1/2008 | Molitor et al. |
| 2008/0027465 | A1 | 1/2008 | Vitali et al. |
| 2008/0027466 | A1 | 1/2008 | Vitali et al. |
| 2008/0045981 | A1 | 2/2008 | Margolin et al. |
| 2008/0051808 | A1 | 2/2008 | Rivera et al. |
| 2008/0065118 | A1 | 3/2008 | Damarati |
| 2008/0083813 | A1 | 4/2008 | Zemlok et al. |
| 2008/0103510 | A1 | 5/2008 | Taylor et al. |
| 2008/0147092 | A1 | 6/2008 | Rogge et al. |
| 2008/0147093 | A1 | 6/2008 | Roskopf et al. |
| 2008/0154287 | A1 | 6/2008 | Rosenberg et al. |
| 2008/0167665 | A1 | 7/2008 | Arp et al. |
| 2008/0167671 | A1 | 7/2008 | Giordano et al. |
| 2008/0228199 | A1 | 9/2008 | Cropper et al. |
| 2008/0243145 | A1 | 10/2008 | Whitfield et al. |
| 2008/0255413 | A1 | 10/2008 | Zemlok et al. |
| 2008/0255589 | A1 | 10/2008 | Blakeney et al. |
| 2008/0306492 | A1 | 12/2008 | Shibata et al. |

(56) References Cited

U.S. PATENT DOCUMENTS

| | | | |
|---|---|---|---|
| 2008/0306493 | A1 | 12/2008 | Shibata et al. |
| 2008/0312665 | A1 | 12/2008 | Shibata et al. |
| 2008/0312670 | A1 | 12/2008 | Lutze et al. |
| 2008/0319456 | A1 | 12/2008 | Hart |
| 2009/0076533 | A1 | 3/2009 | Kayan et al. |
| 2009/0088777 | A1 | 4/2009 | Miyagi et al. |
| 2009/0088783 | A1 | 4/2009 | Kennedy et al. |
| 2009/0171380 | A1 | 7/2009 | Whiting |
| 2009/0222003 | A1 | 9/2009 | Otley |
| 2009/0228023 | A1 | 9/2009 | Cui |
| 2009/0228024 | A1 | 9/2009 | Whitfield et al. |
| 2009/0264904 | A1 | 10/2009 | Aldrich et al. |
| 2009/0299382 | A1 | 12/2009 | Zergiebel |
| 2009/0326558 | A1 | 12/2009 | Cui et al. |
| 2010/0049216 | A1 | 2/2010 | Zergiebel |
| 2010/0057105 | A1 | 3/2010 | Sorrentino et al. |
| 2010/0057107 | A1 | 3/2010 | Sorrentino et al. |
| 2010/0069935 | A1 | 3/2010 | Crainich |
| 2010/0274262 | A1 | 10/2010 | Schulz et al. |
| 2010/0274264 | A1 | 10/2010 | Schulz et al. |
| 2011/0054498 | A1 | 3/2011 | Monassevitch et al. |
| 2011/0082474 | A1 | 4/2011 | Bindra et al. |
| 2011/0087241 | A1 | 4/2011 | Nguyen |
| 2011/0087243 | A1 | 4/2011 | Nguyen et al. |
| 2011/0112552 | A1 | 5/2011 | Lehman et al. |
| 2011/0137323 | A1 | 6/2011 | Malkowski et al. |
| 2011/0137324 | A1 | 6/2011 | Boudreaux et al. |
| 2011/0144662 | A1 | 6/2011 | McLawhorn et al. |
| 2011/0144665 | A1 | 6/2011 | Malkowski |
| 2011/0190791 | A1 | 8/2011 | Jacobs et al. |
| 2011/0208212 | A1 | 8/2011 | Zergiebel et al. |
| 2011/0218553 | A1 | 9/2011 | Huitema et al. |
| 2011/0218554 | A1 | 9/2011 | Cheng et al. |
| 2011/0218555 | A1 | 9/2011 | Huitema |
| 2011/0218556 | A1 | 9/2011 | Nguyen et al. |
| 2011/0224696 | A1 | 9/2011 | Huitema et al. |
| 2011/0224700 | A1 | 9/2011 | Schmidt et al. |
| 2011/0224701 | A1 | 9/2011 | Menn |
| 2011/0230900 | A1 | 9/2011 | Sarradon |
| 2011/0245847 | A1 | 10/2011 | Menn et al. |
| 2011/0245848 | A1 | 10/2011 | Rosenberg et al. |
| 2011/0251608 | A1 | 10/2011 | Timm et al. |
| 2011/0295290 | A1 | 12/2011 | Whitfield |
| 2011/0313437 | A1 | 12/2011 | Yeh |
| 2012/0029534 | A1 | 2/2012 | Whitfield et al. |
| 2012/0041455 | A1 | 2/2012 | Martinez |
| 2012/0046671 | A1 | 2/2012 | Matsuoka et al. |
| 2012/0053402 | A1 | 3/2012 | Conlon et al. |
| 2012/0059394 | A1 | 3/2012 | Brenner et al. |
| 2012/0065647 | A1 | 3/2012 | Litscher et al. |
| 2012/0109158 | A1 | 5/2012 | Zammataro |
| 2012/0116420 | A1 | 5/2012 | Sorrentino et al. |
| 2012/0197269 | A1 | 8/2012 | Zammataro |
| 2012/0265220 | A1 | 10/2012 | Menn |
| 2012/0277765 | A1 | 11/2012 | Zammataro et al. |
| 2012/0330326 | A1 | 12/2012 | Creston et al. |
| 2013/0110135 | A1 | 5/2013 | Whitfield et al. |
| 2013/0131697 | A1 | 5/2013 | Hartoumbekis |
| 2013/0165951 | A1 | 6/2013 | Blake, III |
| 2013/0165952 | A1 | 6/2013 | Whitfield et al. |
| 2013/0172910 | A1 | 7/2013 | Malkowski |
| 2013/0172911 | A1 | 7/2013 | Rockrohr et al. |
| 2013/0172912 | A1 | 7/2013 | Whitfield et al. |
| 2013/0253541 | A1 | 9/2013 | Zergiebel |
| 2013/0274767 | A1 | 10/2013 | Sorrentino et al. |
| 2013/0289583 | A1 | 10/2013 | Zergiebel et al. |
| 2013/0296891 | A1 | 11/2013 | Hartoumbekis |
| 2013/0296892 | A1 | 11/2013 | Sorrentino et al. |
| 2013/0310849 | A1 | 11/2013 | Malkowski |
| 2013/0325040 | A1 | 12/2013 | Zammataro |
| 2014/0005693 | A1 | 1/2014 | Shelton, IV et al. |
| 2014/0039526 | A1 | 2/2014 | Malkowski |
| 2014/0052157 | A1 | 2/2014 | Whitfield et al. |
| 2014/0058412 | A1 | 2/2014 | Aranyi et al. |
| 2014/0194903 | A1 | 7/2014 | Malkowski et al. |
| 2014/0207156 | A1 | 7/2014 | Malkowski |
| 2014/0296879 | A1 | 10/2014 | Menn et al. |
| 2014/0316441 | A1 | 10/2014 | Zergiebel et al. |
| 2014/0330291 | A1 | 11/2014 | Whitfield et al. |
| 2015/0005790 | A1 | 1/2015 | Whitfield et al. |
| 2015/0032131 | A1 | 1/2015 | Sorrentino et al. |
| 2015/0045816 | A1 | 2/2015 | Aranyi et al. |
| 2015/0066057 | A1 | 3/2015 | Rockrohr et al. |
| 2015/0080916 | A1 | 3/2015 | Aranyi et al. |
| 2015/0127022 | A1 | 5/2015 | Whitfield et al. |
| 2015/0164511 | A1 | 6/2015 | Whitfield et al. |
| 2015/0190138 | A1 | 7/2015 | Whitfield et al. |
| 2015/0190139 | A1 | 7/2015 | Zammataro |
| 2015/0282808 | A1 | 10/2015 | Sorrentino et al. |
| 2015/0351771 | A1 | 12/2015 | Malkowski et al. |
| 2015/0351772 | A1 | 12/2015 | Malkowski et al. |
| 2016/0030044 | A1 | 2/2016 | Zammataro |
| 2016/0030045 | A1 | 2/2016 | Malkowski et al. |
| 2016/0113655 | A1 | 4/2016 | Holsten |
| 2016/0151071 | A1 | 6/2016 | Tokarz et al. |
| 2016/0192940 | A1 | 7/2016 | Gokharu |
| 2016/0213377 | A1 | 7/2016 | Shankarsetty |
| 2016/0242789 | A1 | 8/2016 | Sorrentino et al. |
| 2016/0256157 | A1 | 9/2016 | Rockrohr et al. |
| 2016/0256158 | A1 | 9/2016 | Whitfield et al. |
| 2016/0262764 | A1 | 9/2016 | Gokharu |
| 2016/0296236 | A1 | 10/2016 | Whitfield et al. |
| 2016/0338695 | A1 | 11/2016 | Hartoumbekis |
| 2016/0338699 | A1 | 11/2016 | Sorrentino et al. |
| 2017/0027581 | A1 | 2/2017 | Zergiebel et al. |

FOREIGN PATENT DOCUMENTS

| | | | |
|---|---|---|---|
| CN | 1994236 | A | 7/2007 |
| CN | 101401737 | A | 4/2009 |
| CN | 101530340 | A | 9/2009 |
| CN | 100571640 | C | 12/2009 |
| CN | 101658437 | A | 3/2010 |
| CN | 101664329 | A | 3/2010 |
| CN | 101664331 | A | 3/2010 |
| CN | 201683954 | U | 12/2010 |
| CN | 103083059 | A | 5/2013 |
| CN | 103181809 | A | 7/2013 |
| CN | 103181810 | A | 7/2013 |
| CN | 104487006 | A | 4/2015 |
| DE | 20 2009 006113 | U1 | 7/2009 |
| EP | 0 073 655 | A1 | 3/1983 |
| EP | 0 085 931 | A2 | 8/1983 |
| EP | 0 086 721 | A2 | 8/1983 |
| EP | 0 089 737 | A1 | 9/1983 |
| EP | 0 092 300 | A1 | 10/1983 |
| EP | 0324166 | A2 | 7/1989 |
| EP | 0 392 750 | A1 | 10/1990 |
| EP | 0 406 724 | A1 | 1/1991 |
| EP | 0 409 569 | A1 | 1/1991 |
| EP | 0 510 826 | A1 | 10/1992 |
| EP | 0 569 223 | A1 | 11/1993 |
| EP | 0 594 003 | A1 | 4/1994 |
| EP | 0 598 529 | A2 | 5/1994 |
| EP | 0 622 049 | A1 | 11/1994 |
| EP | 0 685 204 | A1 | 12/1995 |
| EP | 0 732 078 | A2 | 9/1996 |
| EP | 0 760 230 | A1 | 3/1997 |
| EP | 0 769 274 | A1 | 4/1997 |
| EP | 0 769 275 | A1 | 4/1997 |
| EP | 0 793 944 | A1 | 9/1997 |
| EP | 0 834 286 | A1 | 4/1998 |
| EP | 0 755 655 | A2 | 1/1999 |
| EP | 1 317 906 | A1 | 6/2003 |
| EP | 1 468 653 | A2 | 10/2004 |
| EP | 1 609 427 | A1 | 12/2005 |
| EP | 1 712 187 | A2 | 10/2006 |
| EP | 1 712 191 | A2 | 10/2006 |
| EP | 1 757 236 | A2 | 2/2007 |
| EP | 1 813 207 | A1 | 8/2007 |
| EP | 1813199 | A1 | 8/2007 |
| EP | 1 894 531 | A2 | 3/2008 |
| EP | 1 908 423 | A2 | 4/2008 |
| EP | 1 913 881 | A1 | 4/2008 |

(56) References Cited

FOREIGN PATENT DOCUMENTS

| | | | |
|---|---|---|---|
| EP | 1 939 231 | A1 | 7/2008 |
| EP | 2 000 102 | A2 | 12/2008 |
| EP | 2 140 817 | A1 | 1/2010 |
| EP | 2 229 895 | A1 | 9/2010 |
| EP | 2 263 570 | A1 | 12/2010 |
| EP | 2332471 | A1 | 6/2011 |
| EP | 2 412 318 | A2 | 2/2012 |
| EP | 2 412 319 | A2 | 2/2012 |
| EP | 2 752 165 | A2 | 7/2014 |
| GB | 1134832 | A | 11/1968 |
| GB | 2073022 | A | 10/1981 |
| GB | 2 132 899 | A | 7/1984 |
| JP | 10-118083 | A | 5/1998 |
| JP | 2003-033361 | A | 2/2003 |
| JP | 2006-501954 | A | 1/2006 |
| JP | 2006-154230 | A | 6/2006 |
| JP | 2006-209948 | A | 8/2006 |
| JP | 2006-277221 | A | 10/2006 |
| JP | 2007-250843 | A | 9/2007 |
| JP | 2008-017876 | A | 1/2008 |
| JP | 2008-047498 | A | 2/2008 |
| JP | 2008-055165 | A | 3/2008 |
| JP | 2008-515550 | A | 5/2008 |
| JP | 2009-198991 | A | 9/2009 |
| JP | 54-99386 | B2 | 5/2014 |
| WO | 01/65997 | A2 | 9/2001 |
| WO | 01-66001 | A2 | 9/2001 |
| WO | 01-67965 | A1 | 9/2001 |
| WO | 03-086207 | A1 | 10/2003 |
| WO | 03-092473 | A2 | 11/2003 |
| WO | 2004-032762 | A1 | 4/2004 |
| WO | 2005-091457 | A1 | 9/2005 |
| WO | 2006-042076 | A2 | 4/2006 |
| WO | 2006-042084 | A2 | 4/2006 |
| WO | 2006-042110 | A2 | 4/2006 |
| WO | 2006-042141 | A2 | 4/2006 |
| WO | 2006-135479 | A2 | 12/2006 |
| WO | 2008-118928 | A2 | 10/2008 |
| WO | 2008-127968 | A2 | 10/2008 |

OTHER PUBLICATIONS

International Search Report corresponding to International Application No. PCT-US08-58185, completed Sep. 4, 2008; mailed Sep. 9, 2008; (2 Pages).

The International Search Report corresponding to International Application No. PCT-US08-59859, completed Sep. 14, 2008; mailed Sep. 18, 2008; (2 Pages).

The extended European Search Report corresponding to European Application No. EP 07 25 3807.7, completed Nov. 7, 2008; mailed Nov. 26, 2008; (11 Pages).

The extended European Search Report corresponding to European Application No. EP 09 25 2049.3, completed Dec. 11, 2009; mailed Jan. 12, 2010; (3 Pages).

The extended European Search Report corresponding to European Application No. EP 09 25 2050.1, completed Dec. 23, 2009; mailed Jan. 21, 2010; (3 Pages).

The extended European Search Report corresponding to European Application No. EP 09 25 2051.9, completed Dec. 21, 2009; mailed Jan. 28, 2010; (3 Pages).

The extended European Search Report corresponding to European Application No. EP 09 25 2052.7, completed Nov. 16, 2009; mailed Nov. 24, 2009; (3 Pages).

The extended European Search Report corresponding to European Application No. EP 09 25 2053.5, completed Nov. 24, 2009; mailed Dec. 1, 2009; (3 Pages).

The extended European Search Report corresponding to European Application No. EP 09 25 2054.3, completed Jan. 7, 2010; mailed Jan. 22, 2010; (3 Pages).

The extended European Search Report corresponding to European Application No. EP 09 25 2056.8, completed Jan. 8, 2010; mailed Feb. 5, 2010; (3 Pages).

The extended European Search Report corresponding to European Application No. EP 10 25 0497.4, completed May 4, 2010; mailed May 12, 2010; (6 Pages).

The extended European Search Report corresponding to European Application No. EP 10 25 2079.8, completed Mar. 8, 2011; mailed Mar. 17, 2011; (3 Pages).

The European Search Report corresponding to European Application No. EP 05 81 0218.7, completed Apr. 18, 2011; mailed May 20, 2011; (3 pages).

The European Search Report corresponding to European Application No. EP 05 80 7612.6, completed May 2, 2011; mailed May 20, 2011; (3 pages).

The extended European Search Report corresponding to European Application No. EP 10 25 1737.2, completed May 9, 2011; mailed May 20, 2011; (4 pages).

The extended European Search Report corresponding to European Application No. EP 11 25 0214.1, completed May 25, 2011; mailed Jun. 1, 2011; (3 Pages).

The extended European Search Report corresponding to European Application No. EP 11 00 2681.2, completed May 31, 2011; mailed Jun. 10, 2011; (3 Pages).

The European Search Report corresponding to European Application No. EP 05 80 2686.5, completed Jan. 9, 2012; mailed Jan. 18, 2012; (3 Pages).

The extended European Search Report corresponding to European Application No. EP 12 15 1313.9, completed Mar. 20, 2012 and mailed Apr. 12, 2012; (5 Pages).

The extended European Search Report corresponding to European Application No. EP 12 16 1291.5, completed Apr. 24, 2012 and mailed May 4, 2012; (5 Pages).

The extended European Search Report corresponding to European Application No. EP 12 16 5891.8, completed Jun. 12, 2012 and mailed Jun. 20, 2012; (6 Pages).

The extended European Search Report corresponding to European Application No. EP 12 16 2288.0, completed Jun. 4, 2012 and mailed Jul. 7, 2012; (6 Pages).

The extended European Search Report corresponding to European Application No. EP 12 16 4955.2, completed Aug. 23, 2012 and mailed Sep. 4, 2012; (5 Pages).

The extended European Search Report corresponding to European Application No. EP 11 25 0754.6, completed Oct. 22, 2012 and mailed Oct. 31, 2012; (6 Pages).

The extended European Search Report corresponding to European Application No. EP 12 18 6401.1, completed Nov. 22, 2012 and mailed Nov. 30, 2012; (7 Pages).

The extended European Search Report corresponding to European Application No. EP 12 18 6448.2, completed Nov. 28, 2012 and mailed Dec. 10, 2012; (6 Pages).

The extended European Search Report corresponding to European Application No. EP 12 19 1706.6, completed Dec. 19, 2012 and mailed Jan. 8, 2013; (6 Pages).

The Extended European Search Report corresponding to EP 12 19 8745.7, completed Mar. 19, 2013 and mailed Apr. 11, 2013; (8 Pages).

The Extended European Search Report corresponding to EP 12 15 2989.5, completed Apr. 9, 2013 and mailed Apr. 18, 2013; (9 Pages).

The Extended European Search Report corresponding to EP 08 73 2820.9, completed Jul. 2, 2013 and mailed Jul. 9, 2013; (10 Pages).

The Extended European Search Report corresponding to EP 13 17 2008.8, completed Aug. 14, 2013 and mailed Aug. 28, 2013; (8 Pages).

The Extended European Search Report corresponding to EP 13 16 6382.5, completed Nov. 19, 2013 and mailed Nov. 28, 2013; (8 Pages).

The Extended European Search Report corresponding to EP 11 25 0194.5, completed Nov. 25, 2013 and mailed Dec. 3, 2013; (8 Pages).

The Extended European Search Report corresponding to EP 10 25 1798.4, completed Dec. 12, 2013 and mailed Jan. 2, 2014; (9 Pages).

"Salute II Disposable Fixation Device", Technique Guide—Laparoscopic and Open Inguinal and Ventral Hernia Repair; Davol, A Bard Company, 2006; (7 Pages).

(56) References Cited

OTHER PUBLICATIONS

The Extended European Search Report corresponding to EP 10 25 2112.7, completed Jul. 29, 2014 and mailed Aug. 5, 2014; (8 pp).
The Extended European Search Report corresponding to EP 14 15 1673.2, completed Apr. 25, 2014 and mailed May 8, 2014; (8 pp).
Chinese Office Action corresponding to counterpart Int'l Appln No. CN 201210212642.9 dated Jun. 3, 2015.
European Office Action corresponding to counterpart Int'l Appln No. EP 04 719 757.9 dated Jun. 12, 2015.
European Office Action corresponding to counterpart Int'l Appln No. EP 13 166 382.5 dated Jun. 19, 2015.
Japanese Office Action corresponding to counterpart Int'l Application No. JP 2010-226908 dated Jun. 26, 2015.
Extended European Search Report corresponding to counterpart Int'l Application No. EP 15 15 5024.1 dated Jul. 17, 2015.
Japanese Office Action corresponding to counterpart Int'l Application No. JP 2011-160126 dated Aug. 10, 2015.
Extended European Search Report corresponding to counterpart Int'l Application No. EP 14 15 0321.9 dated Sep. 23, 2015.
Extended European Search Report corresponding to counterpart Int'l Application No. EP 11 25 0675.3 dated Oct. 7, 2015.
Extended European Search Report corresponding to counterpart Int'l Application No. EP 11 25 0674.6 dated Oct. 7, 2015.
Extended European Search Report corresponding to counterpart Int'l Application No. EP 12 19 3447.5 dated Oct. 19, 2015.
Canadian Office Action corresponding to counterpart Int'l Application No. CA 2,675,875 dated Oct. 26, 2015.
Japanese Office Action corresponding to counterpart Int'l Application No. JP 2015-005629 dated Oct. 28, 2015.
Japanese Office Action corresponding to counterpart Int'l Application No. JP 2014-245081 dated Oct. 28, 2015.
Canadian Office Action corresponding to counterpart Int'l Application No. CA 2,675,921 dated Oct. 30, 2015.
Chinese Office Action corresponding to counterpart Int'l Application No. CN 201210555570.8 dated Nov. 2, 2015.
Canadian Office Action corresponding to counterpart Int'l Application No. CA 2,676,309 dated Nov. 3, 2015.
Canadian Office Action corresponding to counterpart Int'l Application No. CA 2,676,211 dated Nov. 24, 2015.
Canadian Office Action corresponding to counterpart Int'l Application No. CA 2,676,547 dated Nov. 25, 2015.
Extended European Search Report corresponding to counterpart Int'l Application No. EP 15 17 3809.3 dated Nov. 25, 2015.
Chinese Office Action corresponding to counterpart Int'l Application No. CN 201210586814.9 dated Dec. 2, 2015.
Extended European Search Report corresponding to counterpart Int'l Application No. EP 12 17 2940.4 dated Dec. 14, 2015.
European Search Report for EP 14192026 dated Jul. 17, 2015.
Chinese First Office Action corresponding to counterpart Int'l Appln. No. CN 201210586826.1 dated Dec. 30, 2015.
Extended European Search Report corresponding to counterpart Int'l Appln. No. EP 15 19 1313.4 dated Feb. 1, 2016.
Extended European Search Report corresponding to counterpart Int'l Appln. No. EP 15 18 5362.9 dated Feb. 12, 2016.
Extended European Search Report corresponding to counterpart Int'l Appln. No. EP 12 19 7813.4 dated Mar. 7, 2016.
Canadian Office Action corresponding to counterpart Int'l Appln. No. CA 2,676,465 dated Mar. 8, 2016.
Japanese Office Action corresponding to counterpart Int'l Appln. No. JP 2014-245081 dated Mar. 18, 2016.
Japanese Office Action corresponding to counterpart Int'l Appln. No. JP 2015-005629 dated Mar. 18, 2016.
Extended European Search Report corresponding to counterpart Int'l Appln. No. EP 15 19 3549.1 dated Mar. 22, 2016.
International Search Report and Written Opinion corresponding to counterpart Int'l Appln. No. PCT/CN2015/082199 dated Mar. 31, 2016.
Extended European Search Report corresponding to counterpart Int'l Appln. No. EP 15 19 7251.0 dated Apr. 8, 2016.
Extended European Search Report corresponding to counterpart Int'l Appln. No. EP 16 15 0739.7 dated May 17, 2016.
Canadian Office Action corresponding to counterpart Int'l Appln. No. CA 2,716,672 dated May 31, 2016.
Canadian Office Action corresponding to counterpart Int'l Appln. No. CA 2,717,448 dated May 31, 2016.
Canadian Office Action corresponding to counterpart Int'l Appln. No. CA 2,721,951 dated Jun. 1, 2016.
Partial European Search Report corresponding to counterpart Int'l Appln. No. EP 16 15 0287.7 dated Jun. 16, 2016.
Chinese Second Office Action corresponding to counterpart Int'l Appln. No. CN 201210555570.8 dated Jun. 20, 2016.
International Search Report & Written Opinion corresponding to Int'l Appln. No. PCT/CN2015/091603 dated Jul. 8, 2016.
Japanese Office Action corresponding to JP 2011-160130 mailed Dec. 1, 2014.
Chinese Office Action corresponding to CN 201210015011.8 issued Jan. 4, 2015.
Japanese Office Action corresponding to JP 2011-160126 mailed Jan. 9, 2015.
Japanese Office Action corresponding to JP 2011-184521 mailed Jan. 15, 2015.
Extended European Search Report corresponding to 14 18 2236.1 dated Jan. 20, 2015.
Chinese Office Action corresponding to CN 201110201736.1 issued Feb. 9, 2015.
Extended European Search Report corresponding to EP 14 16 1540.1 dated Feb. 27, 2015.
Australian Office Action corresponding to AU 2010226985 issued Mar. 31, 2015.
Australian Office Action corresponding to AU 2013211526 issued Apr. 6, 2015.
Australian Office Action corresponding to AU 2011211463 issued Apr. 13, 2015.
Australian Office Action corresponding to AU 2013254887 issued Apr. 14, 2015.
Japanese Office Action corresponding to JP 2013-225272 mailed May 1, 2015.
European Office Action corresponding to EP 12 152 989.5 dated May 4, 2015.
Australian Office Action corresponding to AU 2009212759 issued May 7, 2015.
Japanese Office Action corresponding to JP 2013-229070 mailed May 8, 2015.
Japanese Office Action corresponding to JP 2013-229996 mailed May 8, 2015.
Japanese Office Action corresponding to JP 2014-190735 dated May 27, 2015; no English translation attached—unavailable.
Chinese Second Office Action corresponding to Int'l Appln. No. CN 201210586814.9 dated Jul. 18, 2016.
Chinese First Office Action corresponding to Int'l Appln. No. CN 201510093591.6 dated Jul. 25, 2016.
International Search Report & Written Opinion corresponding to Int'l Appln. No. PCT/CN2015/094172 mailed Aug. 4, 2016.
Canadian Office Action corresponding to Int'l Appln. No. CA 2,728,538 dated Sep. 6, 2016.
Chinese Second Office Action corresponding to Int'l Appln. No. CN 201210586826.1 dated Sep. 14, 2016.
Extended European Search Report corresponding to Int'l Appln. No. EP 16 15 0287.7 dated Oct. 4, 2016.
Chinese First Office Action corresponding to Int'l Appln. No. CN 201510205737.1 dated Nov. 1, 2016.
European Office Action corresponding to Int'l Appln. No. EP 08 73 2820.9 dated Nov. 3, 2016.
Extended European Search Report corresponding to Int'l Appln. No. EP 16 18 5465.8 dated Dec. 21, 2016.
Extended European Search Report corresponding to Int'l Appln. No. EP 16 18 4652.2 dated Jan. 4, 2017.
Chinese First Office Action corresponding to Int'l Appln. No. CN 201510419902.3 dated Jan. 4, 2017.

* cited by examiner

APPARATUS FOR APPLYING SURGICAL CLIPS

CROSS-REFERENCE TO RELATED APPLICATIONS

This application is a continuation of U.S. patent application Ser. No. 11/245,866, filed Oct. 7, 2005, now U.S. Pat. No. 8,920,438, which claims benefit of U.S. Provisional Application No. 60/617,017 filed Oct. 8, 2004, and the disclosures of each of the above-identified applications are hereby incorporated by reference in their entirety.

BACKGROUND

1. Technical Field

This present disclosure relates generally to an apparatus for applying surgical clips to tissue. More specifically, the present disclosure relates to an apparatus for applying a series of clips to tissue seriatim.

2. Background of Related Art

Surgical procedures frequently require ligation of blood vessels, severed tissues and/or other organs to control or stop bleeding. Clip applying apparatus for quickly applying a surgical clip about tissue are well known. Such clip applying apparatus include single clip applicators and multiple clip applicators. In single clip applicators, a new clip is loaded into the apparatus after application of each clip. Multiple clip applicators include a series of clips which can be sequentially applied to tissue during the course of a surgical procedure. Because surgical procedures usually require the use of a multiplicity of surgical clips, multiple clip applicators are generally preferred.

Typically, clip applying apparatus include a handle mechanism, an elongated body portion, and a clip crimping assembly, e.g., a jaw or pair of jaws. Such clip applying apparatus are configured for endoscopic or open surgical procedures. Although known clip applying apparatus for sequentially advancing individual clips have provided good results, a continuing need exists for a clip applying apparatus which is less complex and provides effective hemostasis.

SUMMARY

In accordance with the present disclosure, an apparatus for applying surgical clips is provided which includes a handle portion including a housing and at least one movable handle and a body portion housing a clip stack. A pair of jaws is supported at the distal end of the body portion. The body portion includes a clip pusher, a camming member and a clip follower. The clip pusher is movably positioned within the body portion and is operable to advance a distal-most clip from the clip stack to a position between the pair of jaws. The camming member is movably positioned within the body portion and is operable to approximate or move the pair of jaws toward each other to deform the distal-most clip of the clip stack. The clip follower is positioned proximally of the clip stack and is operable to urge the clip stack distally towards the pair of jaws. In one embodiment, the body portion includes a lockout member and a stop member. The lockout member is movable from a first position in slidable relation to the camming member to a second position interlocked with the camming member. In its second position, the lockout member is positioned to abut the stop member to limit distal movement of the camming member.

In one embodiment, the lockout member includes at least one flexible leg having a projection and the camming member includes at least one slot dimensioned to receive the projection to interlock or secure the lockout member to the camming member. The at least one flexible leg can include a pair of flexible legs and the at least one slot can include a pair of slots. The lockout member can include a resilient finger which is positioned to releasably retain the lockout member in its first position. In one embodiment, the body portion further includes a separator plate which includes an opening dimensioned to receive a portion of the resilient finger of the lockout member to retain the lockout member in its first position. The clip follower may include a tab and the lockout member may include an engagement member such that the tab is movable into the engagement member to move the lockout member from its first position to its second position. In one embodiment, the tab is positioned to engage the engagement member after the proximal most clip has been advanced to the pair of jaws. Alternately, the tab can be positioned to engage the engagement member when one or more clips are remaining in the apparatus.

In one embodiment, an apparatus for applying surgical clips is provided which includes a handle portion having at least one movable handle and a body portion including a clip pusher and a camming member. The clip pusher is movably supported within the body portion to advance a distal-most clip of a clip stack to a position between a pair of jaws supported at a distal end of the body portion. The camming member is movably supported within the body portion from a retracted position to an advanced position to approximate the pair of jaws. A latch assembly is supported on the clip pusher and includes a pivotal latch member which is movable from a first position engaged with an abutment supported on the camming member to a second position disengaged from the abutment of the camming member. The camming member is operably connected to the at least one movable handle such that movement of the at least one movable handle through an actuation stroke effects movement of the camming member from its advanced position to its retracted position. In one embodiment, the pivotal latch member is urged towards its first position by a biasing member such that movement of the camming member from its retracted position to its advanced position initially effects advancement of the clip pusher. A latch cam is fixedly supported on the body portion and is positioned to engage the pivotal latch member after the clip pusher has advanced the distal-most clip of the clip stack to its position between the jaws to disengage the latch member from the abutment. In one embodiment, a biasing member is positioned to urge the clip pusher to a retracted position after the latch member is disengaged from the abutment. In one embodiment, the body portion includes a housing body and a housing cover and the latch cam is supported on the housing cover. The handle portion can include a yoke which is connected to a proximal end of the camming member. In one embodiment, the at least one handle is operably connected to the yoke by at least one front link such that movement of the at least one handle through an actuation stroke effects advancement of the yoke and the camming member. The handle portion can include a pair of handles with each handle operably connected to the yoke by one front link. In one embodiment, a pair of rear links are provided. Each of the rear links has a first end pivotally connected to a respective front link by a first pivot member and a second end pivotally connected to the handle portion by a second pivot member. Each of the pair of handles defines a cam channel for slidably receiving a respective one of the first pivot members.

In one embodiment, an apparatus for applying surgical clips includes a handle portion, a body portion extending distally from the handle portion, and a jaw body supported at a distal end of the body portion. The jaw body includes first and second jaws movable from a spaced position to a more approximated position. In one embodiment, the body portion includes a camming member which is movable from a retracted position to an advanced position to effect movement of the first and second jaws from their spaced position to their more approximated position. The body portion further includes a resilient jaw locking member removably positioned between the first and second jaws to prevent the jaws from moving from their spaced position to their more approximated position. In one embodiment, the jaw locking member is in the form of a resilient plate and the jaw body includes a pair of inwardly deformable legs. Each of the legs supports one of the first and second jaws and the locking member being positioned between the legs of the jaw body. A distal end of the camming is slidably positioned about the legs of the jaw body and is movable from its retracted position to its advanced position to move the locking member from between the legs of the jaw body and subsequently to effect movement of the first and second jaws to their more approximated position.

BRIEF DESCRIPTION OF THE DRAWINGS

Various embodiments of the presently disclosed clip applying apparatus are described herein with reference to the drawings, wherein.

DETAILED DESCRIPTION OF EMBODIMENTS

Figures 1, 2:
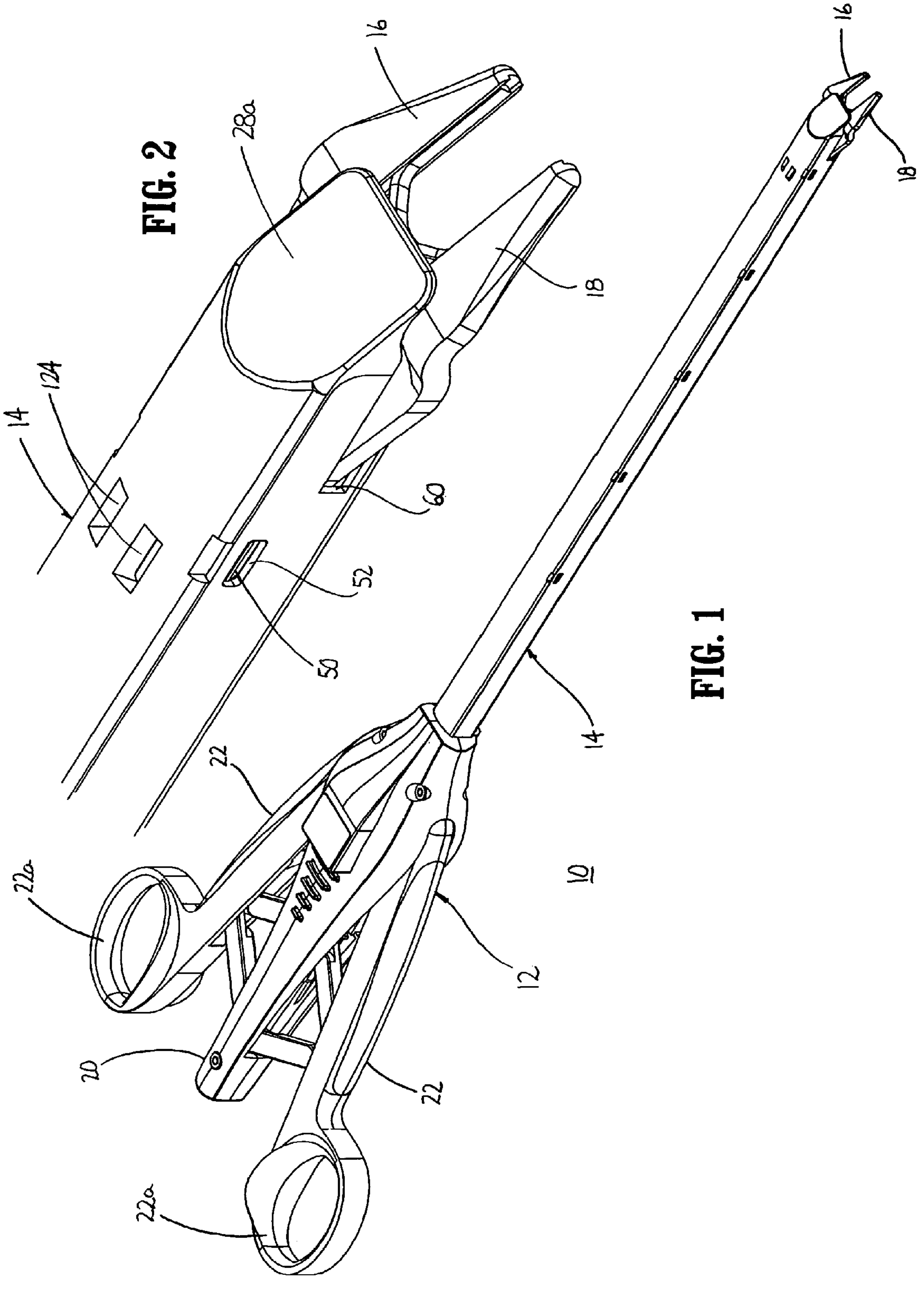
FIG. 1 is a perspective view of one embodiment of the presently disclosed clip applying apparatus.
FIG. 2 is an enlarged perspective view of the distal end of the clip applying apparatus shown in FIG. 1.
Figure 3:
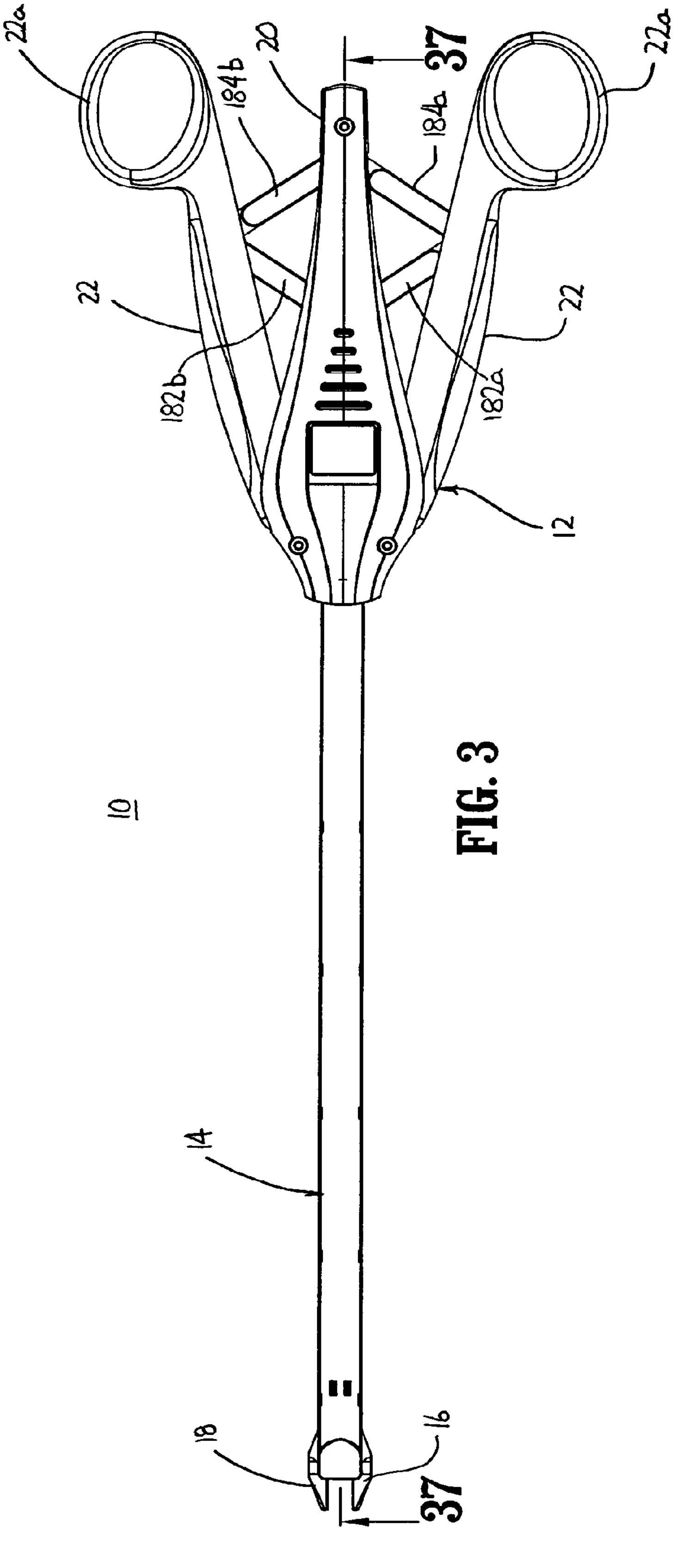
FIG. 3 is a top view of the clip applying apparatus shown in FIG. 1.
Figure 4:
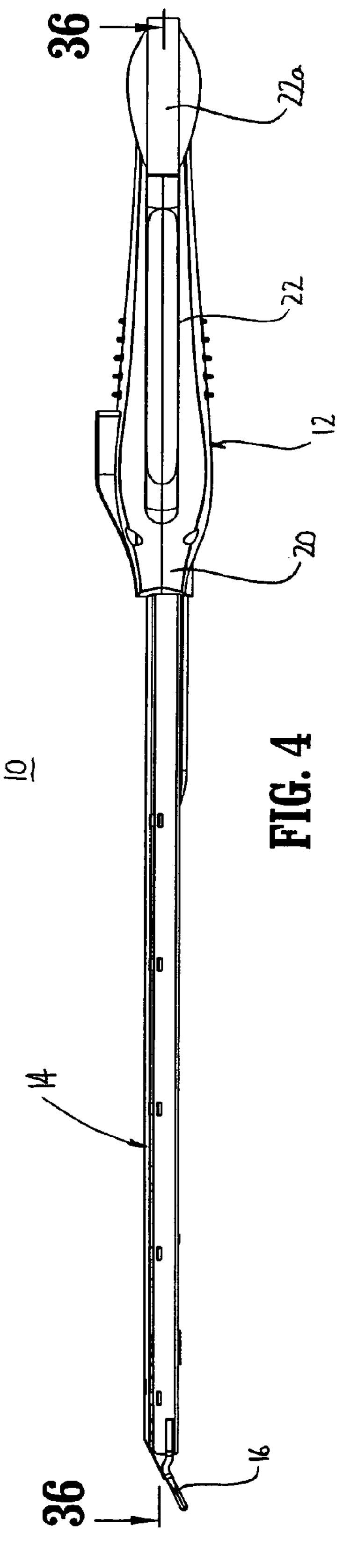
FIG. 4 is a side view of the clip applying apparatus shown in FIG. 1.

Embodiments of the presently disclosed surgical clip applier will now be described in detail with reference to the drawings wherein like reference numerals designate identical or corresponding elements in each of the several views. Throughout this description, the term "proximal" will refer to the portion of the instrument closest to the operator and the term "distal" will refer to the portion of the instrument furthest from the operator.

Referring to FIGS. 1-4, the presently disclosed surgical clip applier, shown generally as 10, includes a handle portion 12, an elongated body portion 14 extending distally from handle portion 12 and first and second jaws 16 and 18 which extend from the distal end of body portion 14. Briefly, handle portion 12 includes a handle housing 20 and a pair of movable handles or triggers 22. Each handle 22 includes a finger loop **22*a*** for receiving a finger of a surgeon's hand.

Referring also to FIGS. 5-9, handle housing 20 can be formed from molded housing half-sections **20*a* and 20*b* (FIG. 5) which are secured together using screws 30 and nuts 32. Alternately, other fastening techniques may be used to secure housing half-sections 20*a* and 20*b* together, e.g., welding, rivets, interlocking structure, adhesives, etc. In one embodiment, the distal end of each handle 22 is pivotally secured about a pivot member 34 such that handles 22, when actuated, move in a scissor-like manner. Each pivot member 34 is positioned between recesses 36*a* and 36*b* formed in half-sections 20*a* and 20*b*, respectively, and may be formed integrally with a respective handle 22 or, in the alternative, as a separate element from a respective handle 22. In one embodiment, each handle 22 has a slip resistant grip member 40 secured to an outside surface thereof and a cam channel 42 formed on an inside surface thereof. Slip resistant grip member 40 can be formed from a cushioning material and overmolded onto each handle 22. It is also contemplated that other slip resistant materials and methods of application may be used to form grip member 40 and apply grip member 40 to a handle 22. Each cam channel 42** is configured to receive a pivot member for connecting a pair of pivotal links as will be described in more detail below.

Figures 10, 12:
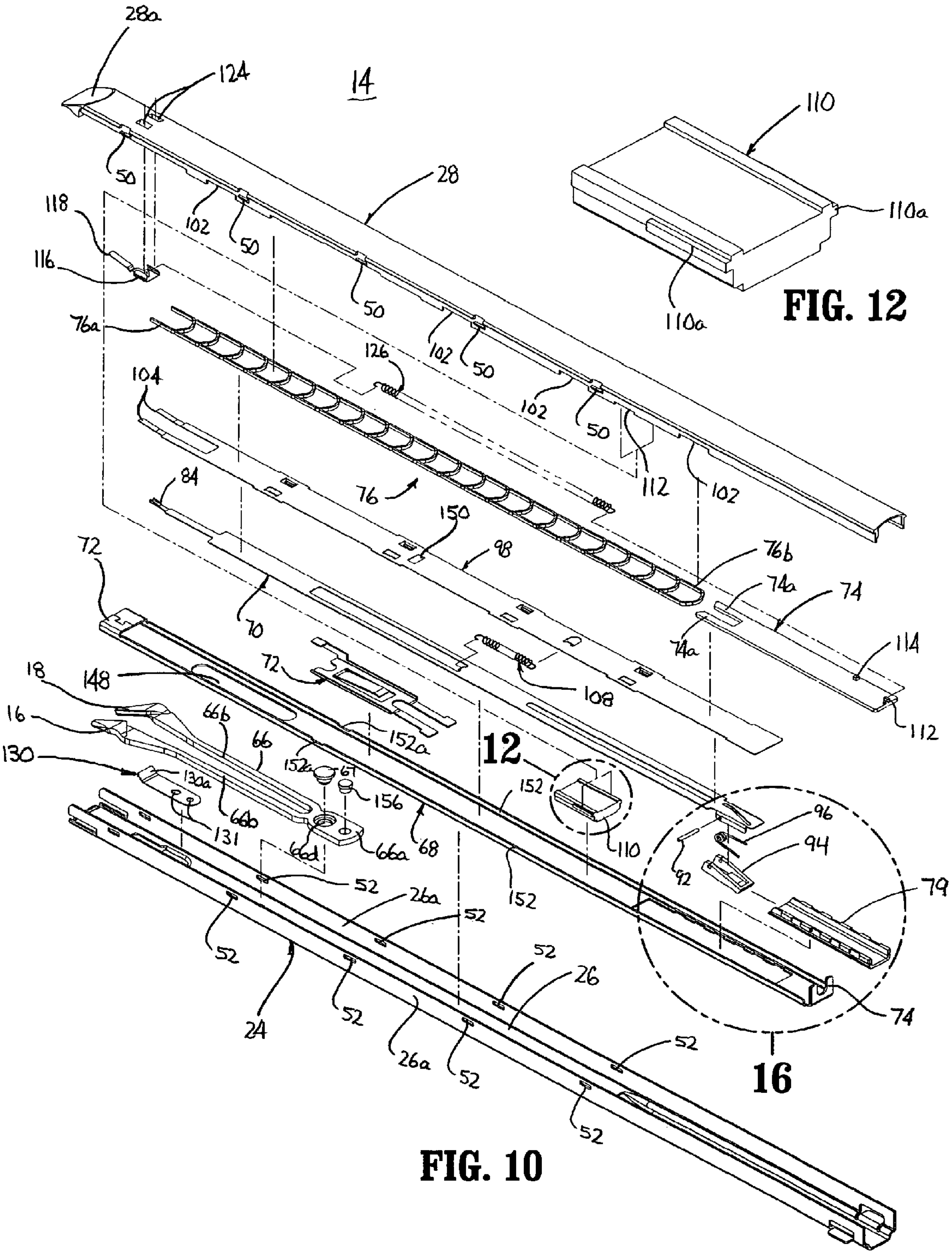
FIG. 10 is an exploded view of the body portion of the clip applying apparatus shown in FIG. 1.
FIG. 12 is an enlarged view of the indicated area of detail shown in FIG. 12.

Referring to FIG. 10, elongated body portion 14 includes a housing body 24 defining a channel 26 for receiving internal components of surgical clip applier 10. A housing cover 28 is secured to housing body 24 and covers channel 26. In one embodiment, housing cover 28 has a series of projections 50 which are dimensioned to be received within openings 52 formed along channel walls **26*a* of housing body 24 to secure housing cover 28 to housing body 24**. Alternately, other securement techniques are contemplated, e.g., adhesives, crimping, screws, etc.

Figures 13, 14, 15:
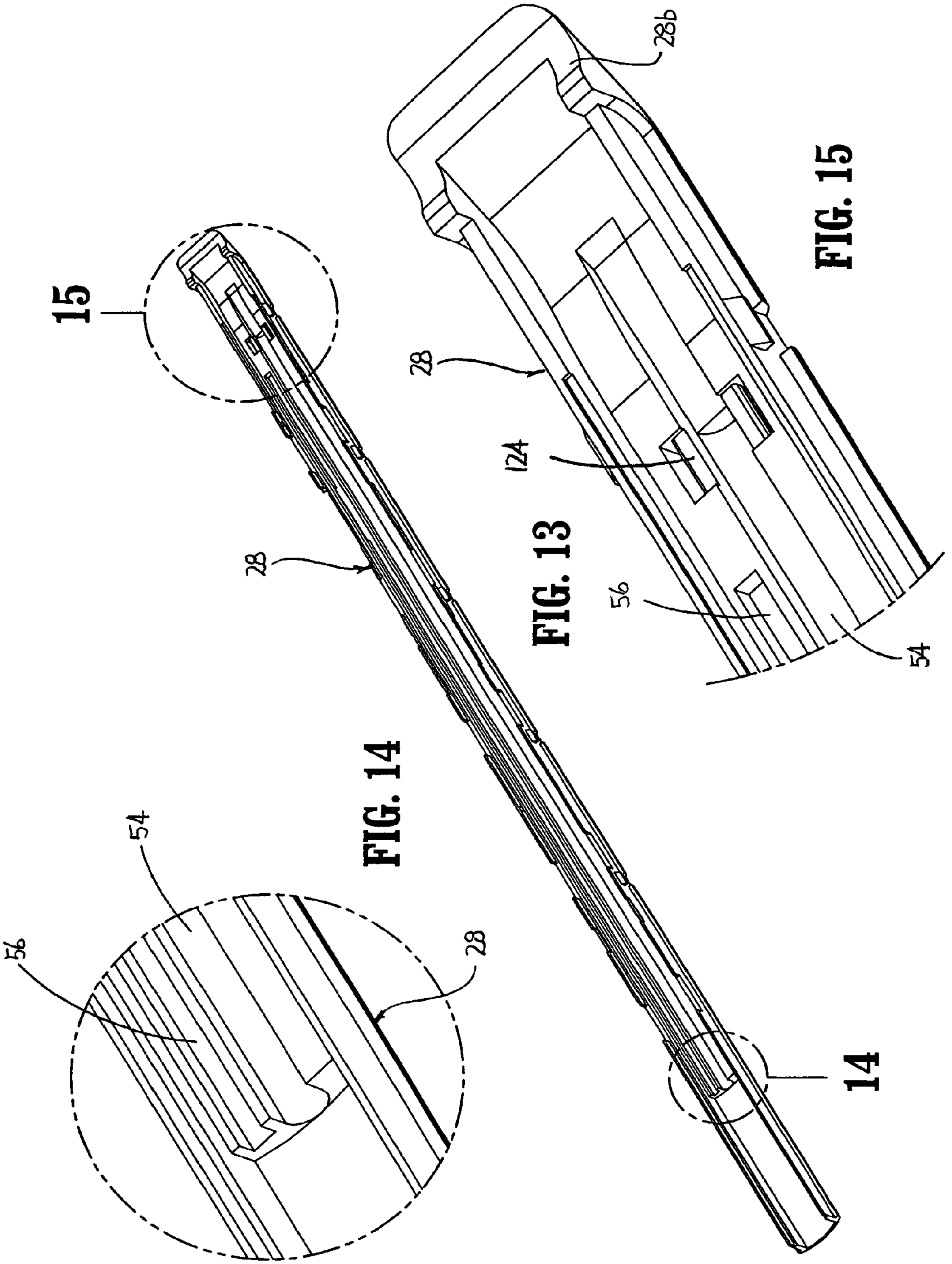
FIG. 13 is a bottom perspective view of the housing cover of the clip applying apparatus shown in FIG. 1.
FIG. 14 is an enlarged view of the indicated area of detail shown in FIG. 13.
FIG. 15 is an enlarged view of the indicated area of detail shown in FIG. 13.

Referring also to FIGS. 13-15, an internal surface of housing cover 28 includes a first longitudinal groove 54 and a second longitudinal groove 56. Grooves 54 and 56 accommodate other components of the elongated body portion as will be discussed in further detail below. The distal end of housing cover 28 includes an outer surface **28*a* which is tapered or angled downwardly towards housing body 24. Angled outer surface 28*a* provides easier access to tissue and reduces the likelihood of the clip applier snagging tissue during use. An inner surface 28*b* formed on the distal end of housing cover 28 has a curvature which corresponds to the curvature of a top surface of jaws 16 and 18. Inner surface 28*b* is positioned in abutting relation to jaws 16 and 18 to provide stability to and prevent misalignment of jaws 16 and 18 during operation of clip applier 10**.

Figures 18, 19, 20, 21:
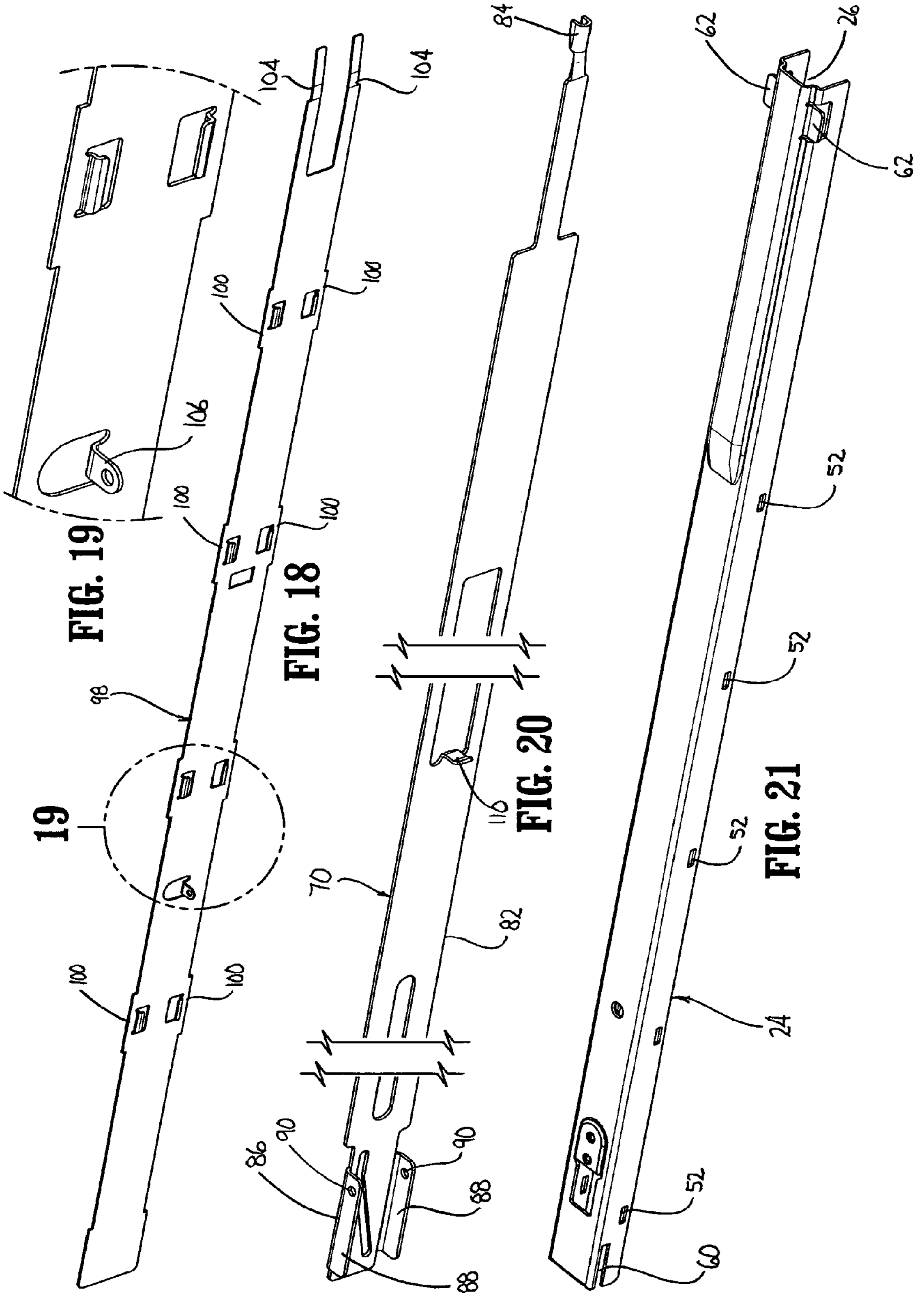
FIG. 18 is a bottom perspective view of the separator plate of the clip applying apparatus shown in FIG. 1.
FIG. 19 is an enlarged view of the indicated area of detail shown in FIG. 18.
FIG. 20 is a bottom perspective view of the clip pusher of the clip applying apparatus shown in FIG. 1.
FIG. 21 is a bottom perspective view of the housing body of the clip applying apparatus shown in FIG. 1.
Figures 29, 30, 31:
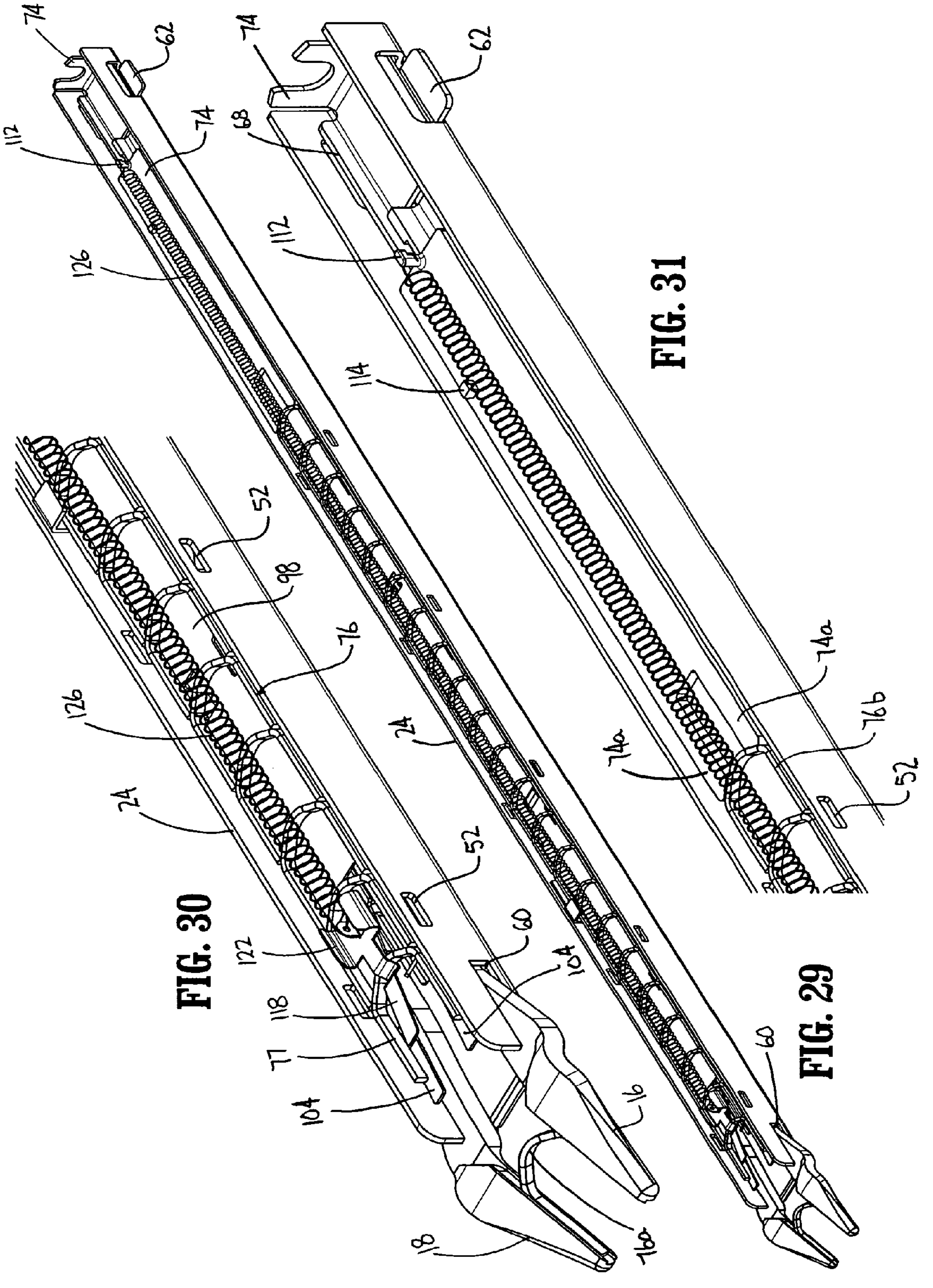
FIG. 29 is a perspective view of the body portion of the clip applying apparatus shown in FIG. 1 with the housing cover removed.
FIG. 30 is an enlarged perspective view of the distal end of the body portion shown in FIG. 29.
FIG. 31 is an enlarged perspective view of the proximal end of the body portion shown in FIG. 29.
Figures 32, 33:
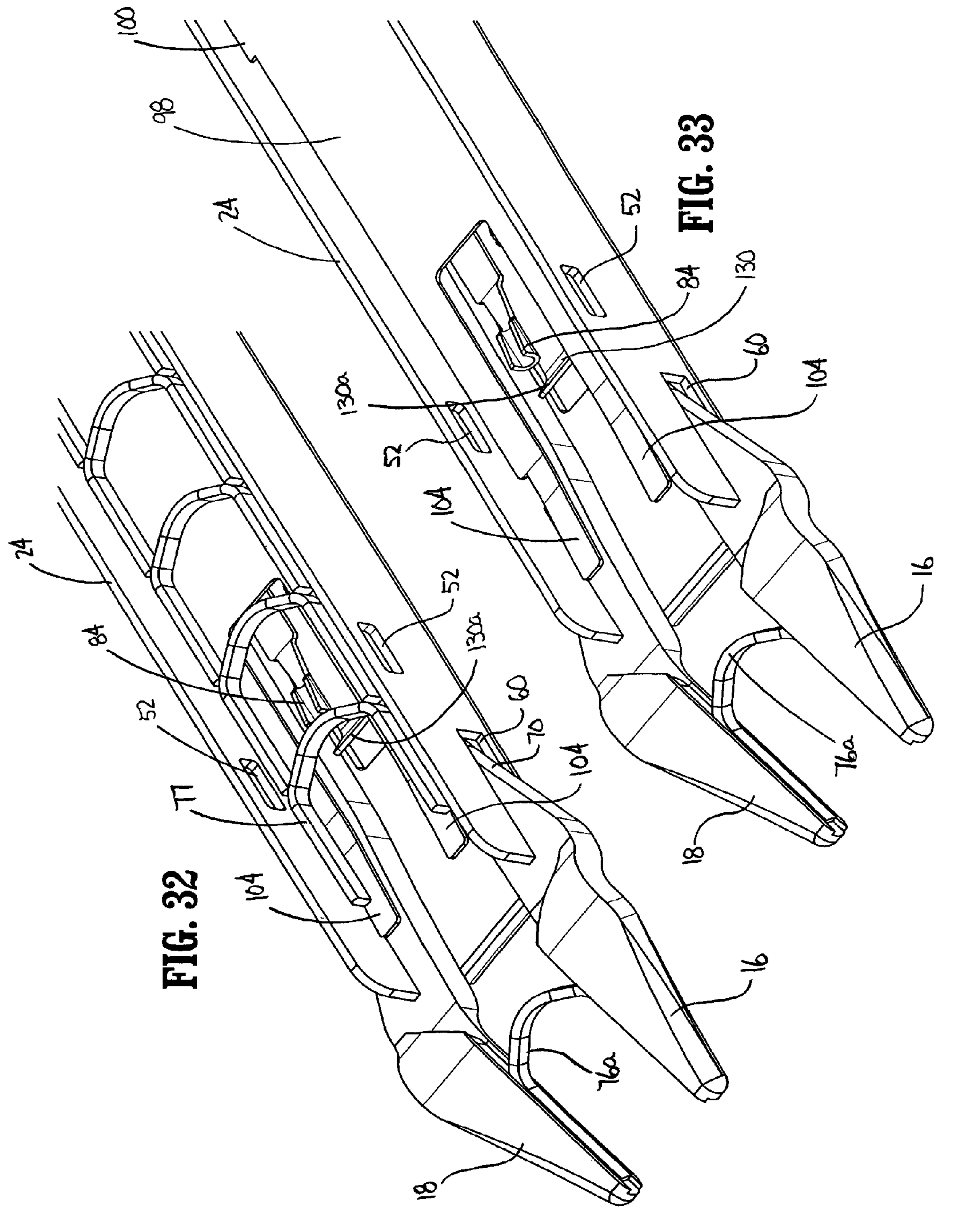
FIG. 32 is an enlarged perspective view of the distal end of the body portion shown in FIG. 29 with the clip follower biasing member and the clip stop member removed.
FIG. 33 is an enlarged perspective view of the distal end of the body portion shown in FIG. 32 with the clip stack removed.
Figures 34, 35:
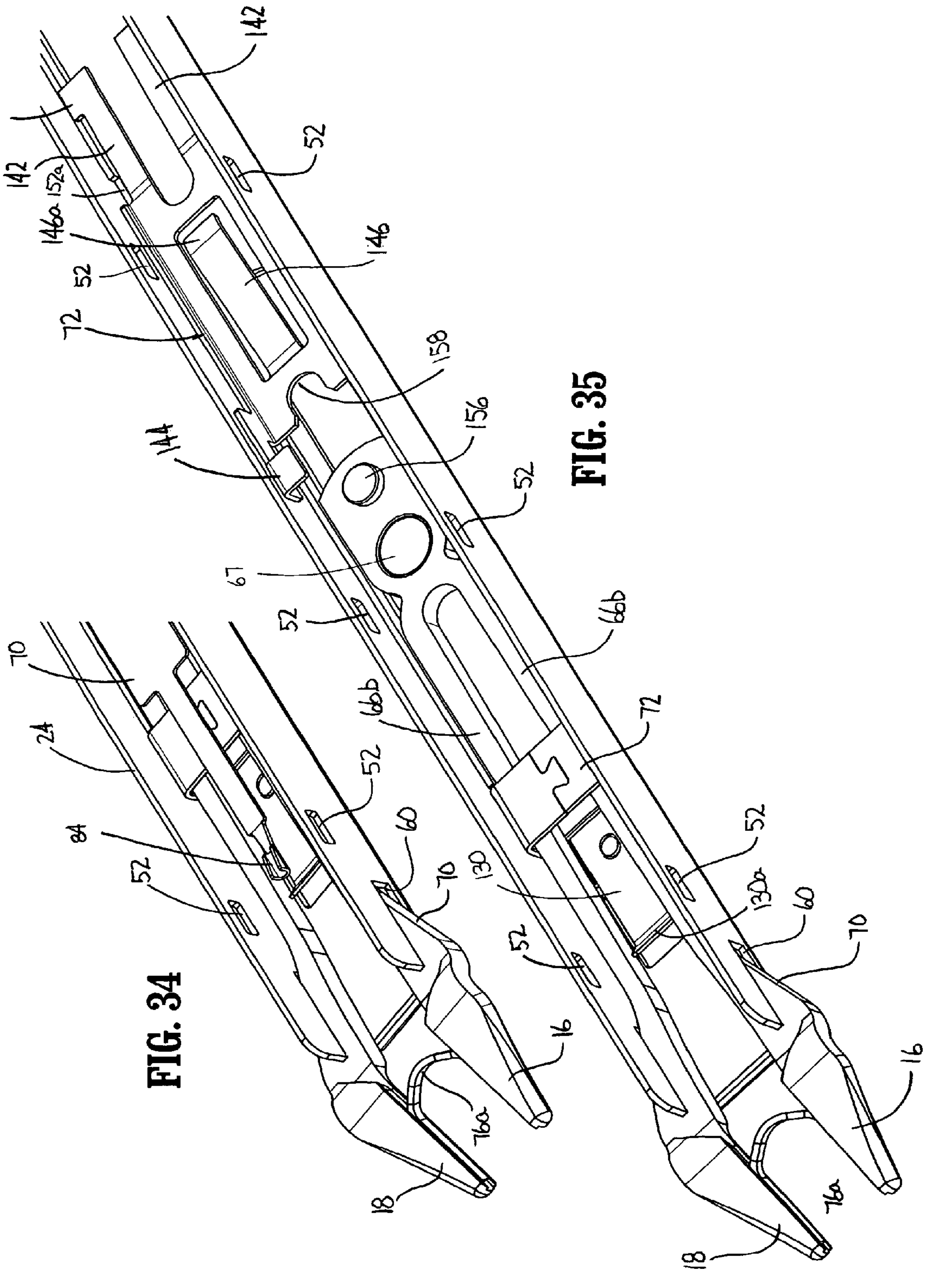
FIG. 34 is an enlarged perspective view of the distal end of the body portion shown in FIG. 33 with the separator plate shown removed.
FIG. 35 is an enlarged perspective view of the distal end of the body portion shown in FIG. 34 with the clip pusher removed.

Referring to FIGS. 10 and 21, housing body 24 includes a pair of distally located cutouts 60 configured to slidably receive jaws 16 and 18. Cutouts 60 are dimensioned to confine jaws 16 and 18 to prevent misalignment of the jaws during actuation of clip applier 10 (FIG. 30). The proximal end of housing body 24 includes a pair of transversely extending wings 62 which are dimensioned to be received within recesses 64 formed in housing half-sections 20*a* and 20*b* (FIG. 9) to secure elongated body portion 14 to handle portion 12.

Figure 23:
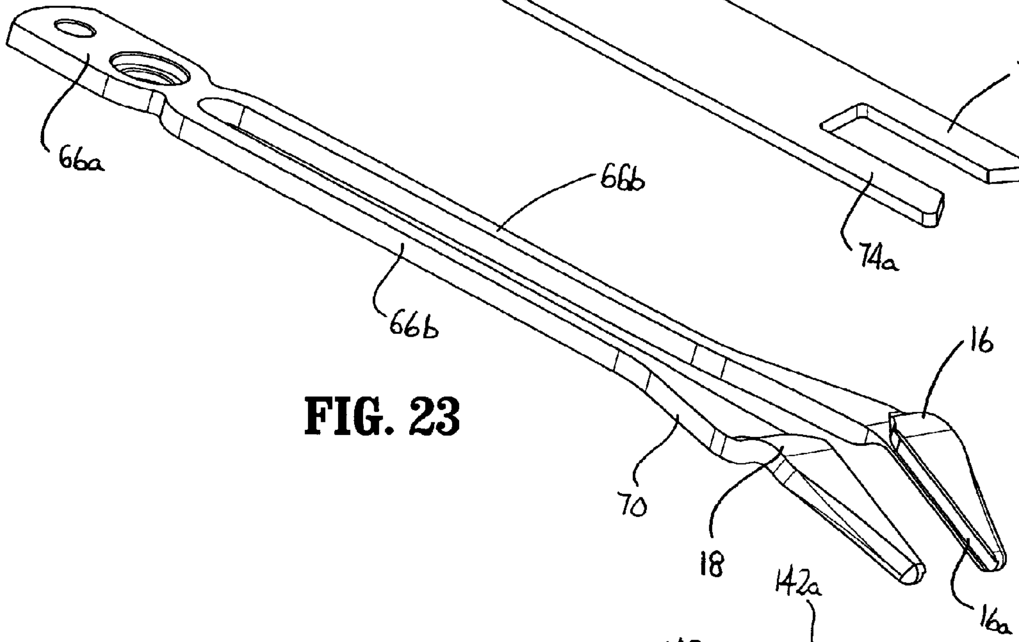
FIG. 23 is a top perspective view of the jaw body of the clip applying apparatus shown in FIG. 1.

As illustrated in FIG. 10, the internal components of clip applier 10 include a jaw body 66, a camming member 68, a clip pusher 70, a clip pusher lockout 72, a clip stack follower 74, and a clip stack 76 including a distal-most clip 76*a* and a proximal-most clip 76*b*. Referring also to FIG. 23, jaw body 66 includes jaws 16 and 18, a proximal mounting portion 66*a* and a pair of spaced distally extending legs 66*b*. Each of jaws 16 and 18 is supported on a distal end of a respective one of legs 66*b* and includes a clip channel 16*a* and 18*a*, respectively. A cam surface 70 is formed on an outer surface of each jaw 16 and 18. Cam surfaces 70 are positioned to be engaged by camming member 68 (FIG. 10) in a manner to be described in further detail below. Jaw body 66 is mounted within channel 26 of housing body 24 using a bolt 67 or the like. Bolt 67 extends through an opening 66*d* in body 66 and through housing body 24.

Figure 16:
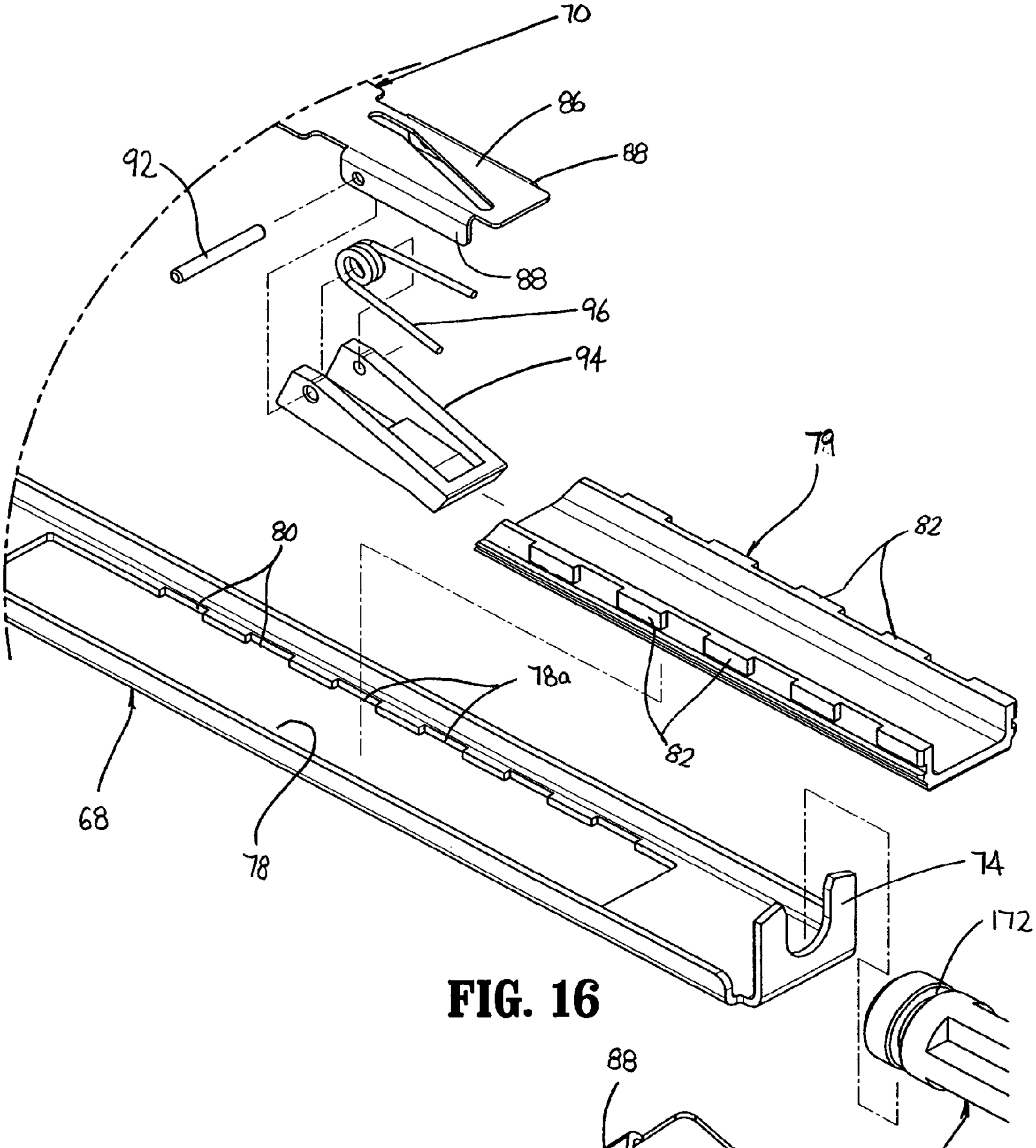
FIG. 16 is an enlarged view of the indicated area of detail shown in FIG. 10.
Figure 17:
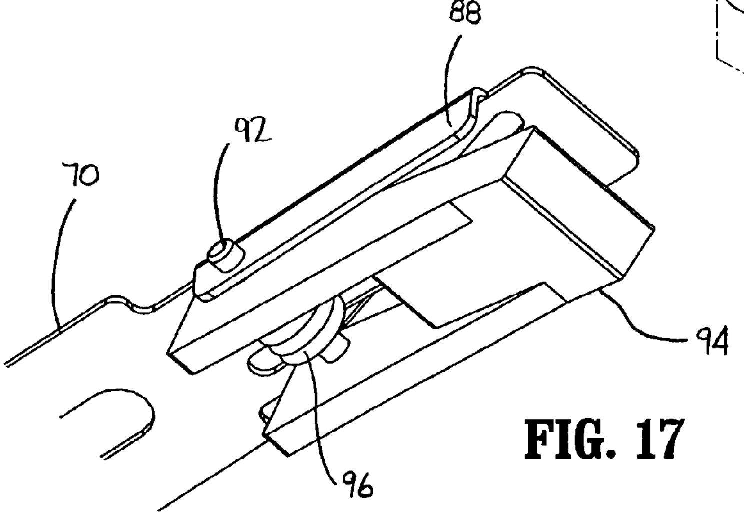
FIG. 17 is a perspective view of the proximal end of the clip pusher of the clip applying apparatus shown in FIG. 1 with the pusher latch assembly secured thereto.
Figure 46:
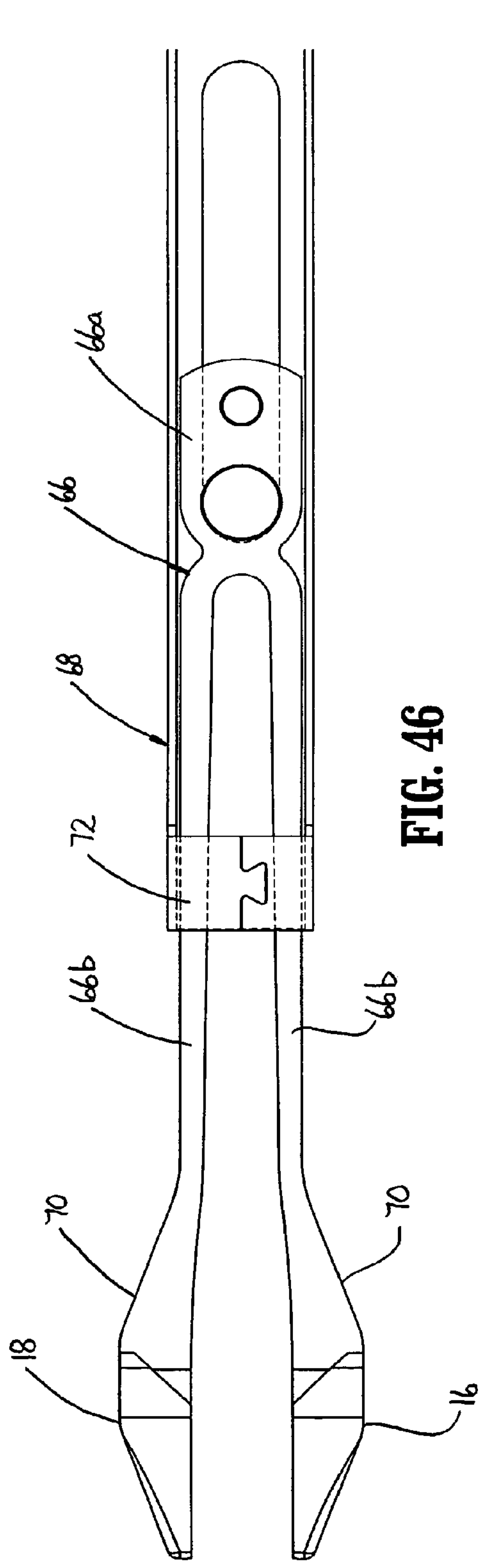
FIG. 46 is a top view of the jaw body and the distal end of the camming member of the clip applying apparatus shown in FIG. 36.
Figure 48:
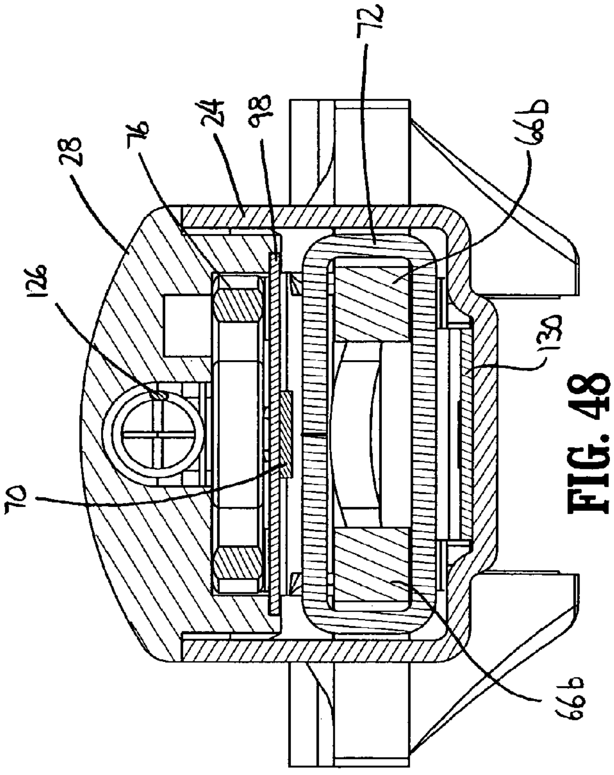
FIG. 48 is a cross-sectional view taken along section lines 48-48 of FIG. 40.
Figure 47:
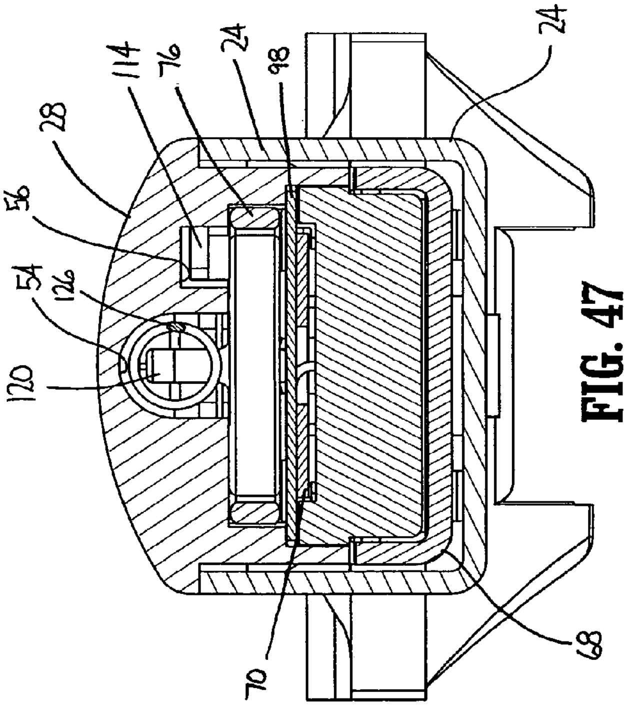
FIG. 47 is a cross-sectional view taken along section lines 47-47 of FIG. 44.
Figure 49:
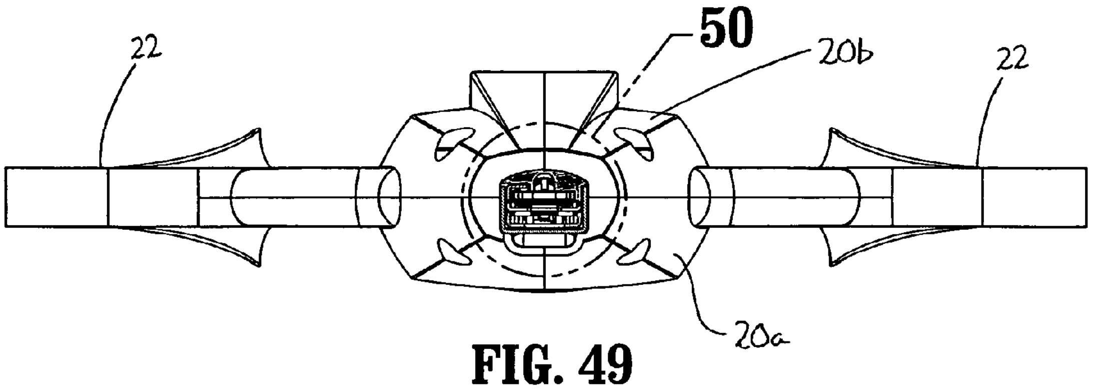
FIG. 49 is a cross-sectional view taken along section lines 49-49 of FIG. 42.
Figure 50:
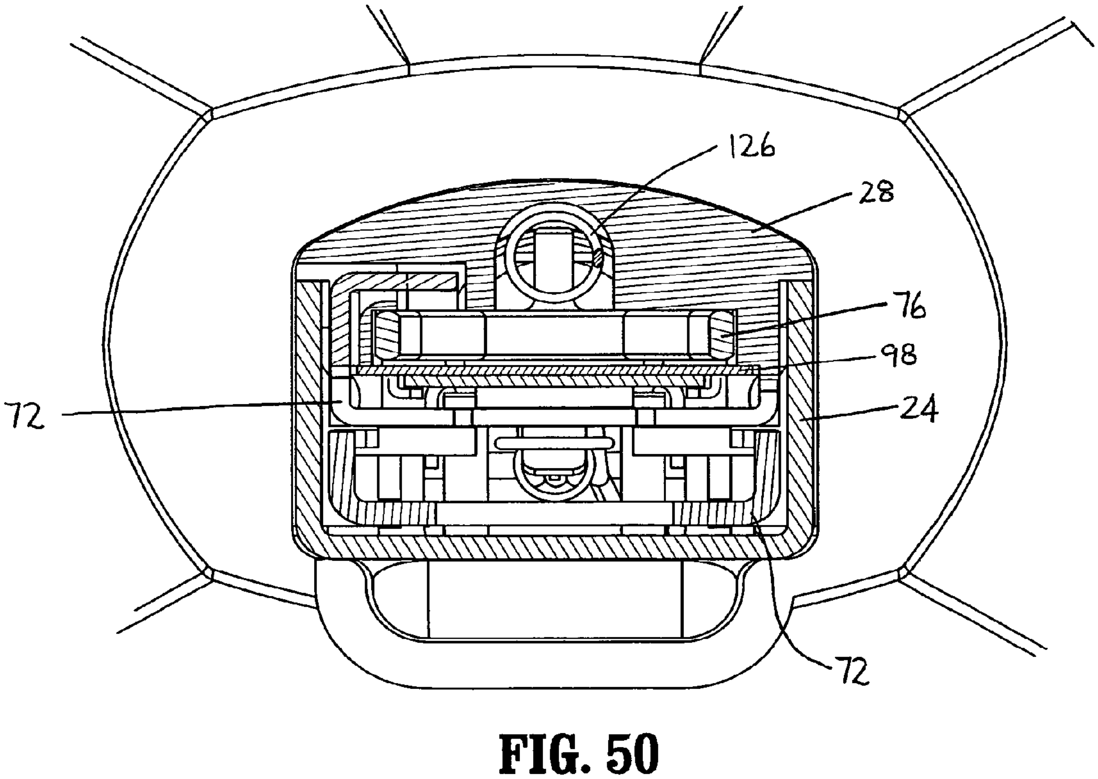
FIG. 50 is an enlarged view of the indicated area of detail shown in FIG. 49.
Figure 60:
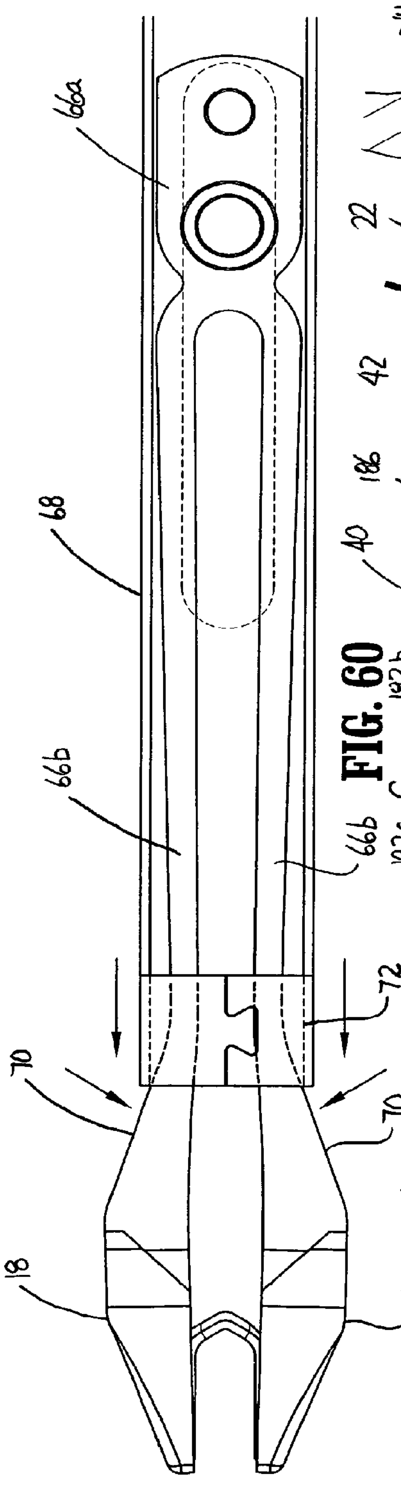
FIG. 60 is a top view of the jaw body and camming member shown in FIG. 46 with the camming member advanced further distally.

Referring now to FIGS. 10 and 16, camming member 68 is slidably supported within channel 26 (FIG. 10) of housing body 24 and includes a distal engagement member 72 which is positioned about legs 66*b* of jaw body 66 (FIG. 48). Engagement member 72 can have a substantially rectangular configuration. Alternately, other configurations are contemplated, e.g., C-shaped configuration. The proximal end of camming member 68 includes a bracket 74 to operably connect camming member 68 to handle portion 12 as will be discussed in further detail below. Handles 22 of handle portion 12 (FIG. 1) are operable to move camming member 68 between a retracted position and an advanced position along channel 26 of housing body 24. In the retracted position of camming member 68, engagement member 72 is positioned about legs 66*b* of jaw body 66 at a location proximal of cam surfaces 70 (FIG. 46). In the advanced position of camming member 68, engagement member 72 is positioned about jaws 16 and 18 in abutting relation to cam surfaces 70 (FIG. 60).

The proximal end of camming member 68 supports an abutment member 79. In one embodiment, abutment member 79 is supported within a cutout 78 formed in the proximal end of camming member 68. Cutout 78 includes a plurality of grooves 78*a* which receive tongues or projections 82 formed on abutment member 79 to secure abutment member 79 to camming member 68. It is contemplated that abutment member 79 may be attached to camming member 68 using other known fastening techniques. Alternately, abutment member 79 can be formed integrally with camming member 68. Abutment member 79 is positioned to engage a pusher latch assembly 80, as will be described in detail below.

Figure 53:
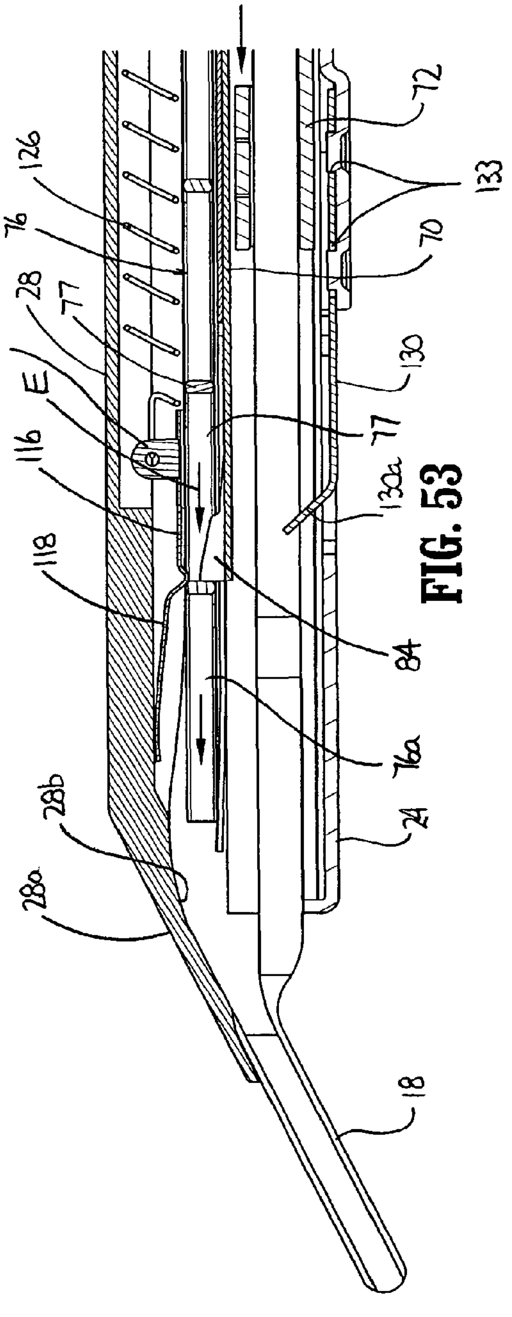
FIG. 53 is a side cross-sectional view of the distal end of the body portion of the clip applying apparatus shown in FIG. 1 during initial actuation of the handle portion.
Figure 54:
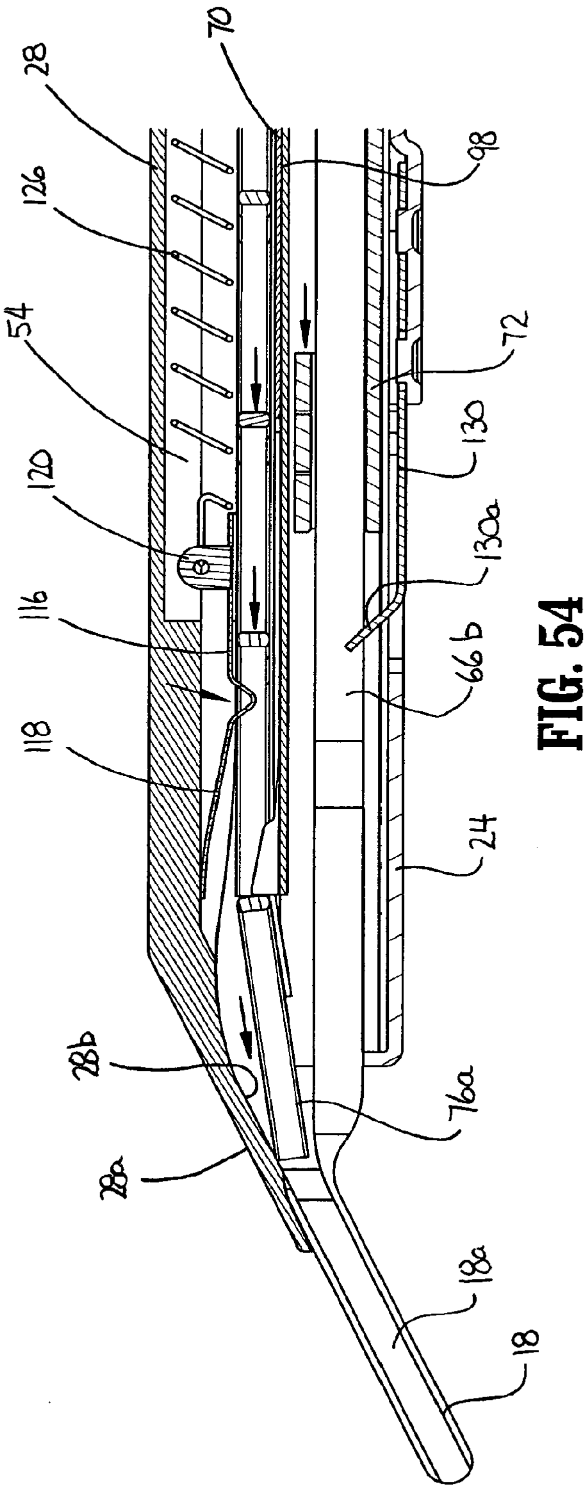
FIG. 54 is a side cross-sectional view of the distal end of the body portion of the clip applying apparatus shown in FIG. 1 during further actuation of the handle portion.

Referring to FIGS. 10, 16, 17 and 20, clip pusher 70 includes an elongated body 82, a distal finger 84, and a proximal latch assembly mount 86. Distal finger 84 is semi-circular in shape and is positioned to engage distal-most clip 76*a* of the stack of clips 76 when clip pusher 70 is moved from a retracted position to an advanced position (FIG. 53). Latch assembly mount 86 includes a pair of spaced, vertical brackets 88. Brackets 88 each include an opening 90 for receiving a pivot pin 92 (FIG. 16) of pusher latch assembly 80.

Pusher latch assembly 80 includes a latch member 94, a biasing member 96, and pivot pin 92. Latch member 94 is pivotally secured at its distal end between brackets 88 of clip pusher 70 about pivot pin 92. Biasing member 96 is positioned between the proximal end of clip pusher 70 and latch member 94 to urge the proximal end of latch member 94 away from clip pusher 70 to a position to engage abutment member 79 when camming member 68 is moved from its retracted to its advanced position. Latch member 94 is pivotal against the urging of biasing member 96 towards the proximal end of clip pusher 70 to move latch member 94 out of engagement with abutment member 79 as will be discussed in further detail below.

Referring to FIGS. 10 and 18, a separator plate 98 is fixedly supported between housing body 24 and housing cover 28. Separator plate 98 includes a series of projections 100 which are received within recesses 102 formed in housing cover 28 to secure separator plate 98 to housing cover 28. The distal end of separator plate 98 includes a pair of spaced spring fingers 104 which are positioned to guide the distal-most clip 76*a* of clip stack 76 into jaws 16 and 18. A biasing member securement member 106 (FIG. 19) is formed on separator plate 98. A biasing member, which can be a coil spring 108, has one end secured to securement member 106 of separator plate 98 and a second end secured to a securement member 110 (FIG. 20) formed on clip pusher 70. Coil spring 108 is in tension and urges clip pusher 70 to its retracted position. When handles 22 (FIG. 1) are operated to move camming member 68 from its retracted position to its advanced position, abutment member 79 engages latch member 94 to move latch member 94 and clip pusher 70 distally toward its advanced position against the urging of coil spring 108. As clip pusher 70 moves distally with camming member 68, distal finger 82 of clip pusher 70 engages distal-most clip 76*a* of clip stack 76 to advance distal-most clip 76*a* into jaws 16 and 18.

Referring to FIGS. 10 and 12, a pusher latch cam 110 is supported in channel 26 between housing body 24 and housing cover 28. Pusher latch cam 110 includes a pair of tabs 110*a* which are received within recesses 112 formed in housing cover 28 to fixedly secure pusher latch cam 110 in relation to housing cover 28. Pusher latch cam 110 is positioned in channel 26 at a position to engage the distal end of latch member 94 (FIG. 57) to pivot and disengage latch member 94 from abutment member 79 when distal-most clip 76*a* has been fully advanced into jaws 16 and 18. When latch member 94 is disengaged from abutment member 79, coil spring 108 returns clip pusher 70 to its retracted position. Although pusher latch cam 110 is illustrated as block shaped, other configurations are envisioned. Further, pusher latch cam may be integrally formed with housing cover 28 or housing body 24.

Figure 22:
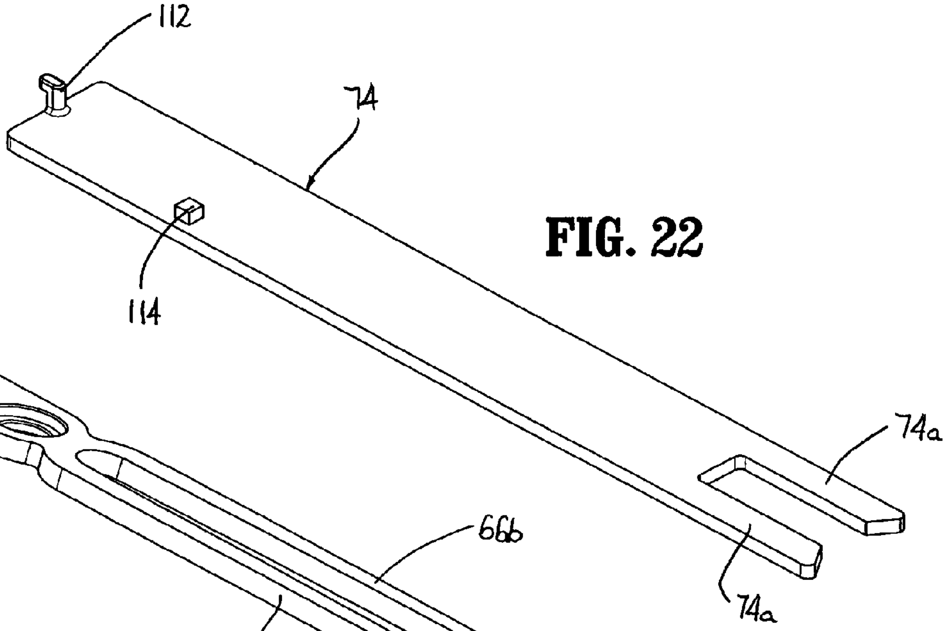
FIG. 22 is a top perspective view of the clip follower of the clip applying apparatus shown in FIG. 1.

Referring to FIGS. 10 and 22, clip stack 76 is slidably supported on a top surface of separator plate 98. A clip follower 74 is positioned behind the proximal-most clip 76*b* of clip stack 76. Clip follower 74 includes a pair of distally extending arms 74*a*. The distal end of each arm 74*a* is configured to engage the backspan of proximal-most clip 76*b*. A top surface of clip follower 74 includes a spring securement member 112 and a lockout tab 114. Lockout tab 114 is positioned to travel in second longitudinal groove 56 (FIG. 14) of housing cover 28 and is movable with clip follower 74 as clip follower 74 is advanced to move clip stack 76 distally within elongated body portion 14.

Figure 11:
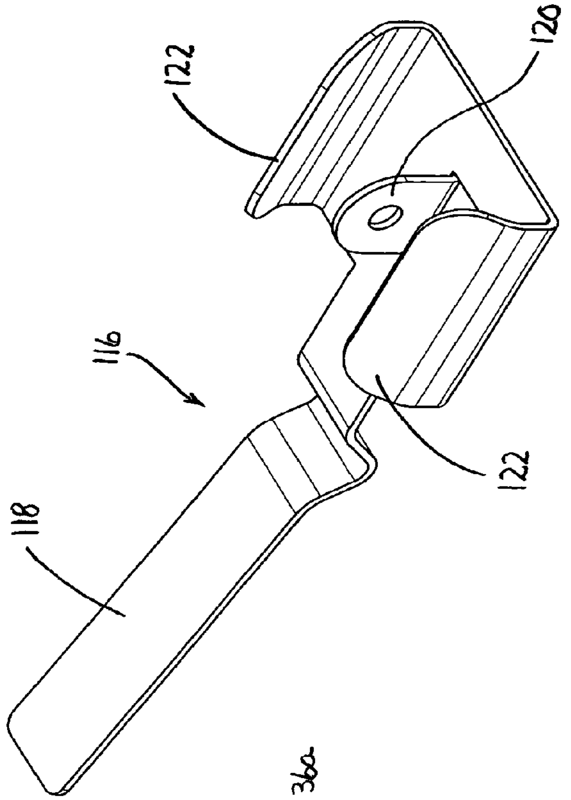
FIG. 11 is a perspective view of the clip stop member of the clip applying apparatus shown in FIG. 1.
Figure 9:
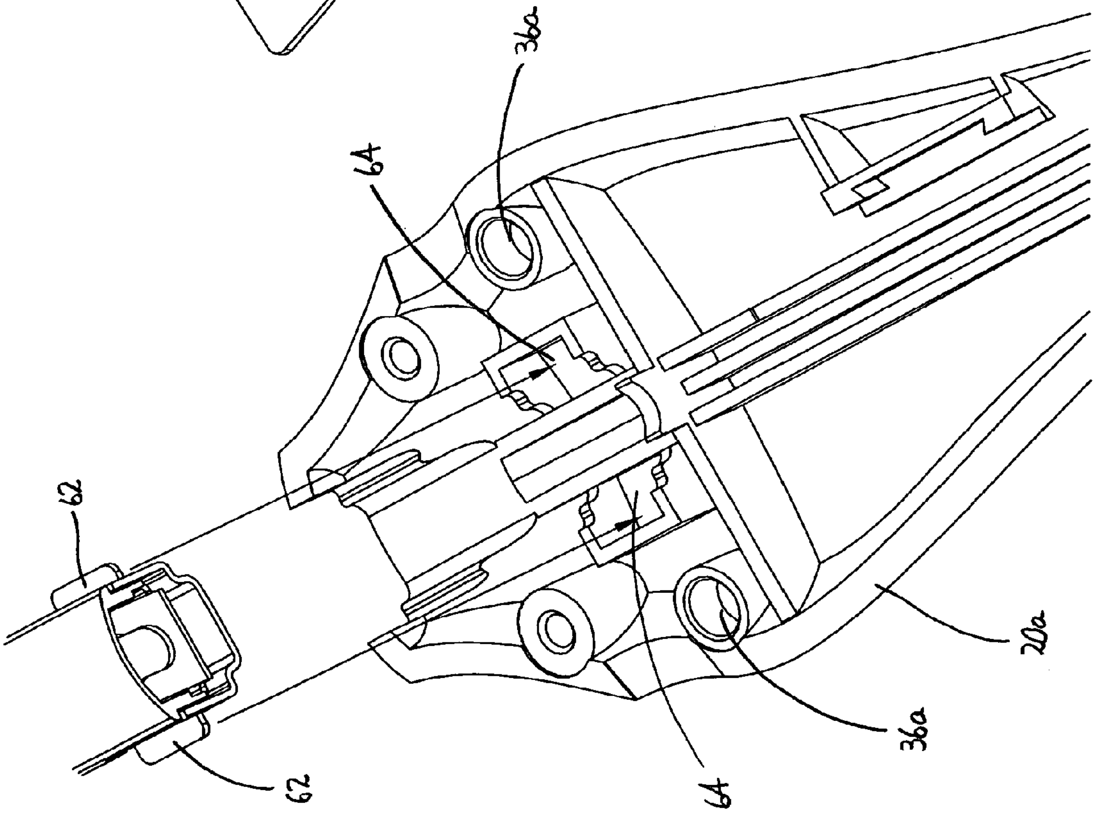
FIG. 9 is a perspective view of the proximal end of the body portion and the interior of a housing half-section with the internal components of the handle portion removed.

Referring to FIGS. 10 and 11, a clip stop member 116 includes a spring arm 118, a spring securement member 120 and a pair of anchor members 122. Anchor members 122 are dimensioned to be snap-fit into a pair of openings 124 formed through a distal portion of housing cover 28 to secure clip stop member 116 to the underside of housing cover 28. A biasing member 126 extends between spring securement member 120 of clip stop member 116 and spring securement member 112 of follower 74. Biasing member

126, which can be a coil spring, is supported in tension between follower 74 and clip stop member 116 to urge follower 74 and clip stack 76 distally within body portion 14 towards jaws 16 and 18. Biasing member 126 is positioned within first longitudinal groove 54 of housing cover 28 (FIG. 14). Clip stop member 116 prevents distal-most clip 76*a* from being pushed distally into jaws 16 and 18 until clip pusher 70 is moved to its advanced position. When clip pusher 70 is moved to its advanced position, clip stop member 116 is deflected upwardly by movement of distal-most clip 76*a* (FIG. 53).

Figure 59:
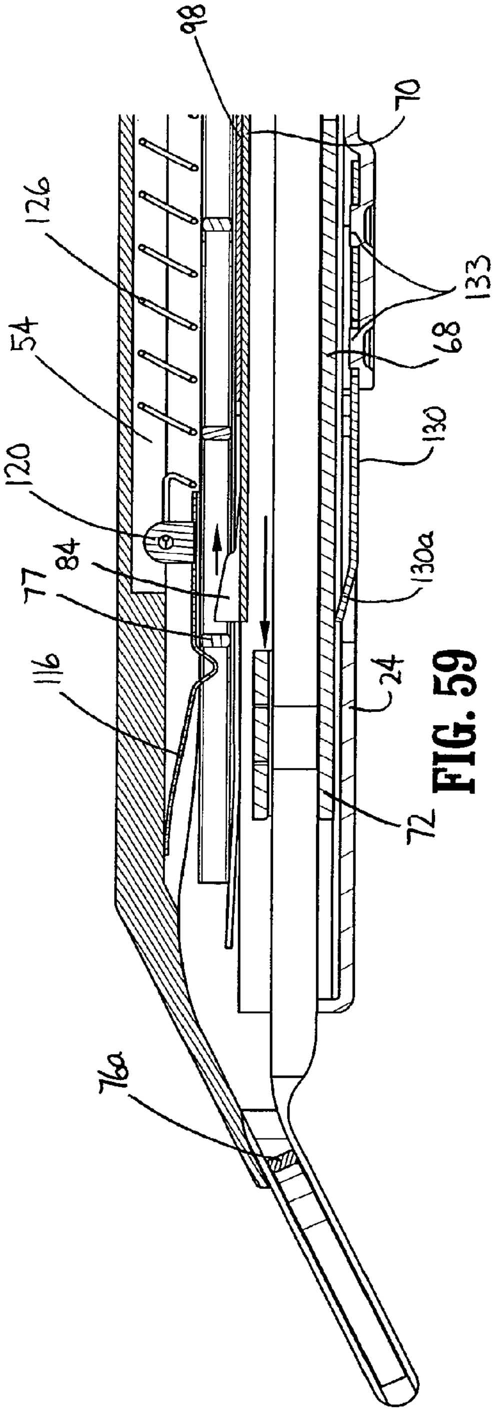
FIG. 59 is a side cross-sectional view of the distal end of the body portion shown in FIG. 55 after further actuation of the handle portion.

A jaw locking member, e.g., plate 130 (FIG. 10) is secured to housing body 24 within channel 26 of housing body 24. Jaw locking plate 130 includes openings 131 which are dimensioned to receive projections 133 (FIG. 59) formed on housing body 24 to secure plate 130 to body 24. Jaw locking plate 130 has a resilient and flexible arm 130*a* which is positioned between legs 66*b* of jaw body 66 to prevent jaws 16 and 18 from being closed inadvertently during positioning of clip applier 10 at a surgical site. When camming member 68 is moved to its advanced position, the distal end of engagement member 72 of camming member 68 deflects arm 130*a* downwardly to move arm 130*a* from between jaws 16 and 18 and allow for closure of jaws 16 and 18 (FIG. 59). Alternately, the jaw locking member need not be in the form of a flat plate but rather other configurations are envisioned, e.g., cylindrical or any configuration positionable between jaws 16 and 18 to prevent closure of the jaws.

Figure 24:
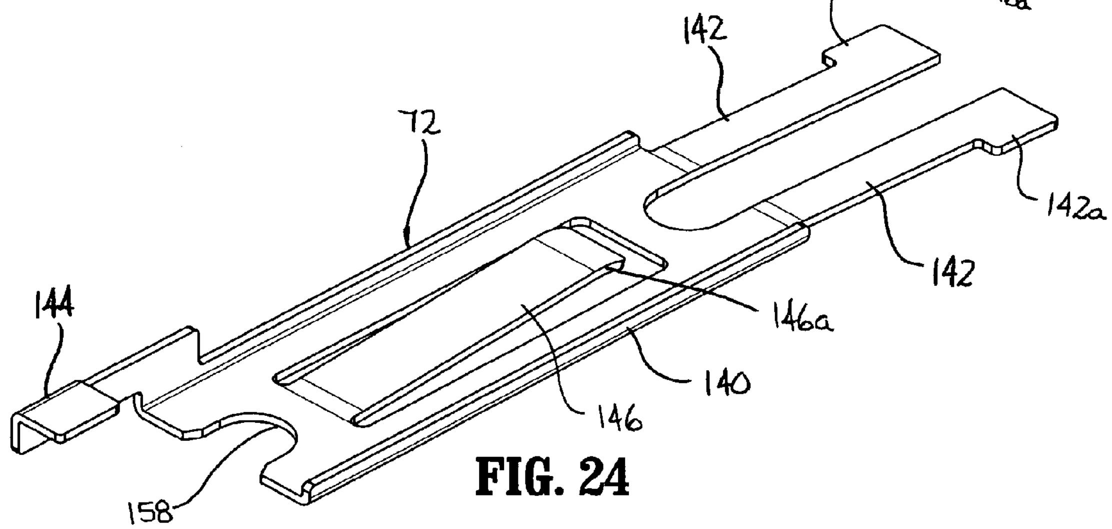
FIG. 24 is a top perspective view of the clip applying apparatus shown in FIG. 1.

Referring to FIGS. 10 and 24, a lockout member 72 is positioned above camming member 68 within channel 26 of housing body 24. Lockout member 72 includes a central body portion 140, a pair of flexible legs 142 and a distally extending engagement member or flag 144. Central body portion 140 includes a proximally extending resilient finger 146 which extends upwardly towards separator plate 98 and includes a downwardly curved end 146*a*. End 146*a* is positioned to extend through an elongated slot 148 formed in clip pusher 70 and to be partially received within an opening 150 formed in separator plate 98. Engagement of end 146*a* of finger 146 in opening 150 of separator plate 98 releasably retains lockout 72 at a fixed position in relation to separator plate 98 until an external force is applied to engagement member 144 as will be discussed in detail below.

Each of flexible legs 142 of lockout 72 includes a radial projection 142*a*. Legs 142 are positioned within the confines of sidewalls 152 of camming member 68 and are urged inwardly by sidewalls 152. A pair of slots 152*a* are formed in sidewalls 152 such that when projections 142*a* are moved into alignment with slots 152*a*, legs 142 spring outwardly to move radial projections 142*a* into slots 152*a*. When projections 142*a* are positioned within slots 152*a*, lockout 72 is fixedly secured to camming member 68.

As discussed above, follower 74 is urged distally by biasing member 126 to urge clip stack 76 distally along separator plate 98. As each clip 76*a* is advanced into jaws 16 and 18, follower 74 moves further distally within elongated body 14. As the proximal-most clip 76*b* is advanced in jaws 16 and 18, lockout tab 114 of follower 74 engages engagement member or flag 144 of lockout 72 and effects distal movement of lockout 72 in relation to camming member 68, such that after proximal-most clip 76*b* is crimped between jaws 16 and 18 and camming member 68 is returned to its retracted position, radial projections 142*a* align with slots 152*a* in camming member 68 to fixedly secure lockout 72 to camming member 68.

A stop member 156 (FIG. 10) is secured to a proximal end of mounting portion 66*a* of jaw body 66. In one embodiment, stop member 156 includes a cylindrical dowel. Alternately, other stop member configurations are envisioned. The distal end of lockout 72 includes a recess 158 for receiving stop member 156. Since stop member 156 is fixedly secured within channel 26 of housing body 24, engagement between lockout 72 and stop member 156 prevents further distal advancement of lockout 72. As discussed above, after the proximal-most clip 76*b* has been applied to tissue, lockout 72 is fixedly secured to camming member 68. Stop member 156 is also received in recess 158 of lockout 72. Thus, after proximal-most clip 76*b* has been applied to tissue and lockout 72 is fixed to camming member 86, engagement between lockout 72 and stop member 156 prevents distal advancement of camming member 68. As will be discussed below, since camming member 68 is connected via linkages to handles 22 (FIG. 1), engagement between lockout 72 and stop member 156 will prevent actuation of handles 22 and thus, indicate to a surgeon that the clip applier clip stack 76 has been depleted.

Figure 5:
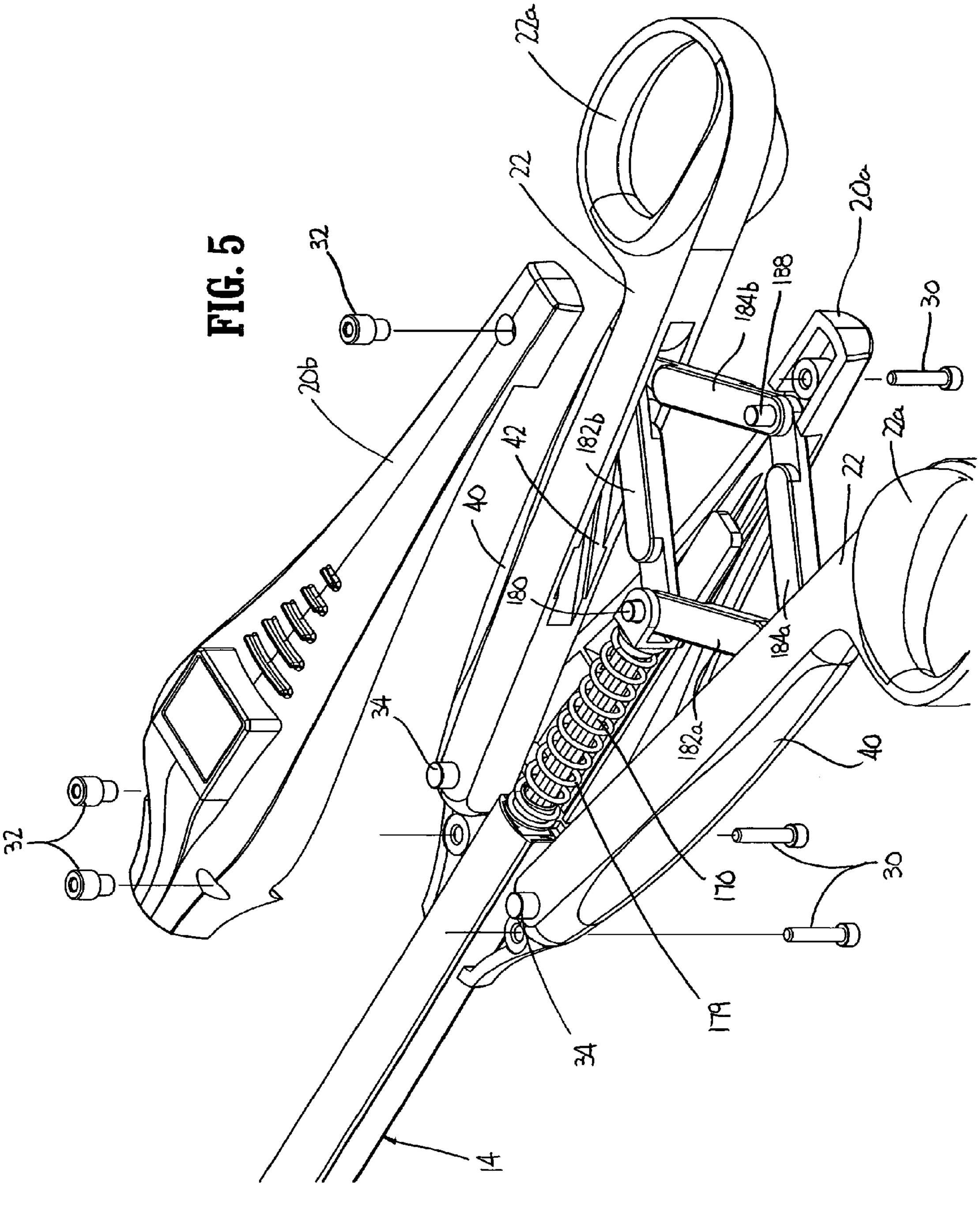
FIG. 5 is a perspective view of the proximal portion of the clip applying apparatus shown in FIG. 4 with the top housing half-section exploded.
Figures 6, 7:
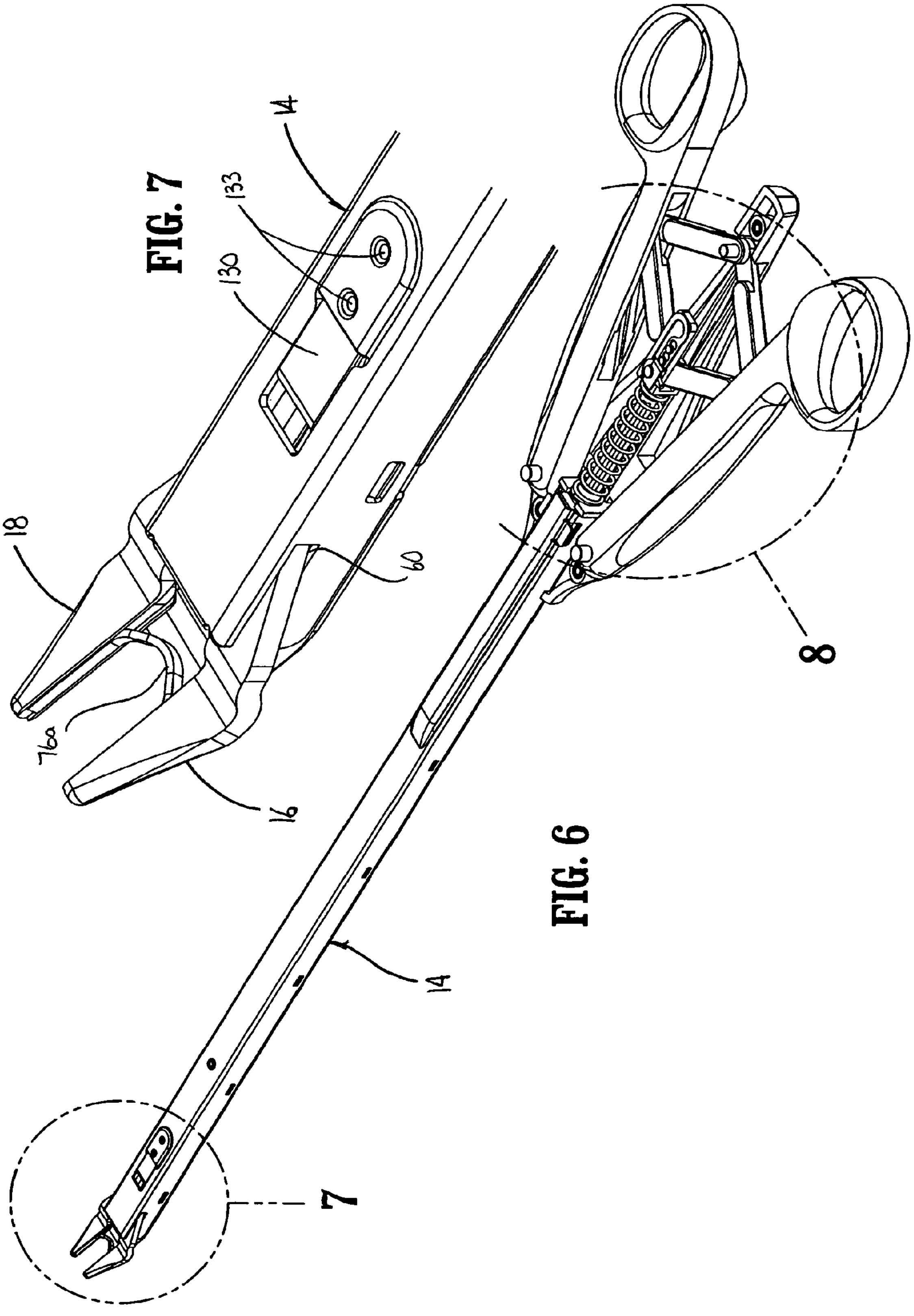
FIG. 6 is a perspective view of the clip applying apparatus shown in FIG. 1 with the top housing half-section removed.
FIG. 7 is an enlarged view of the indicated area of detail shown in FIG. 6.
Figure 8:
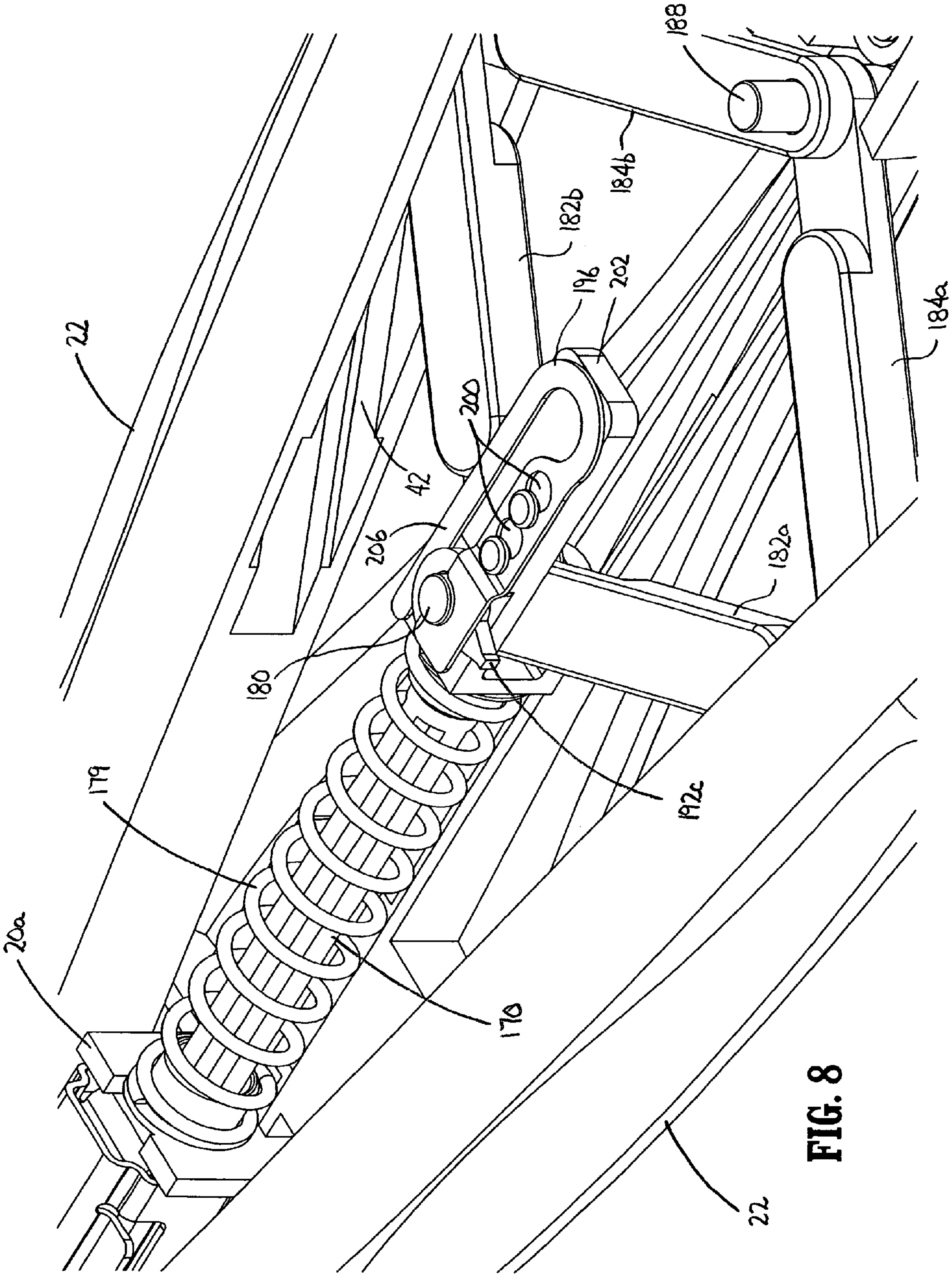
FIG. 8 is an enlarged view of the indicated area of detail shown in FIG. 6.
Figure 51:
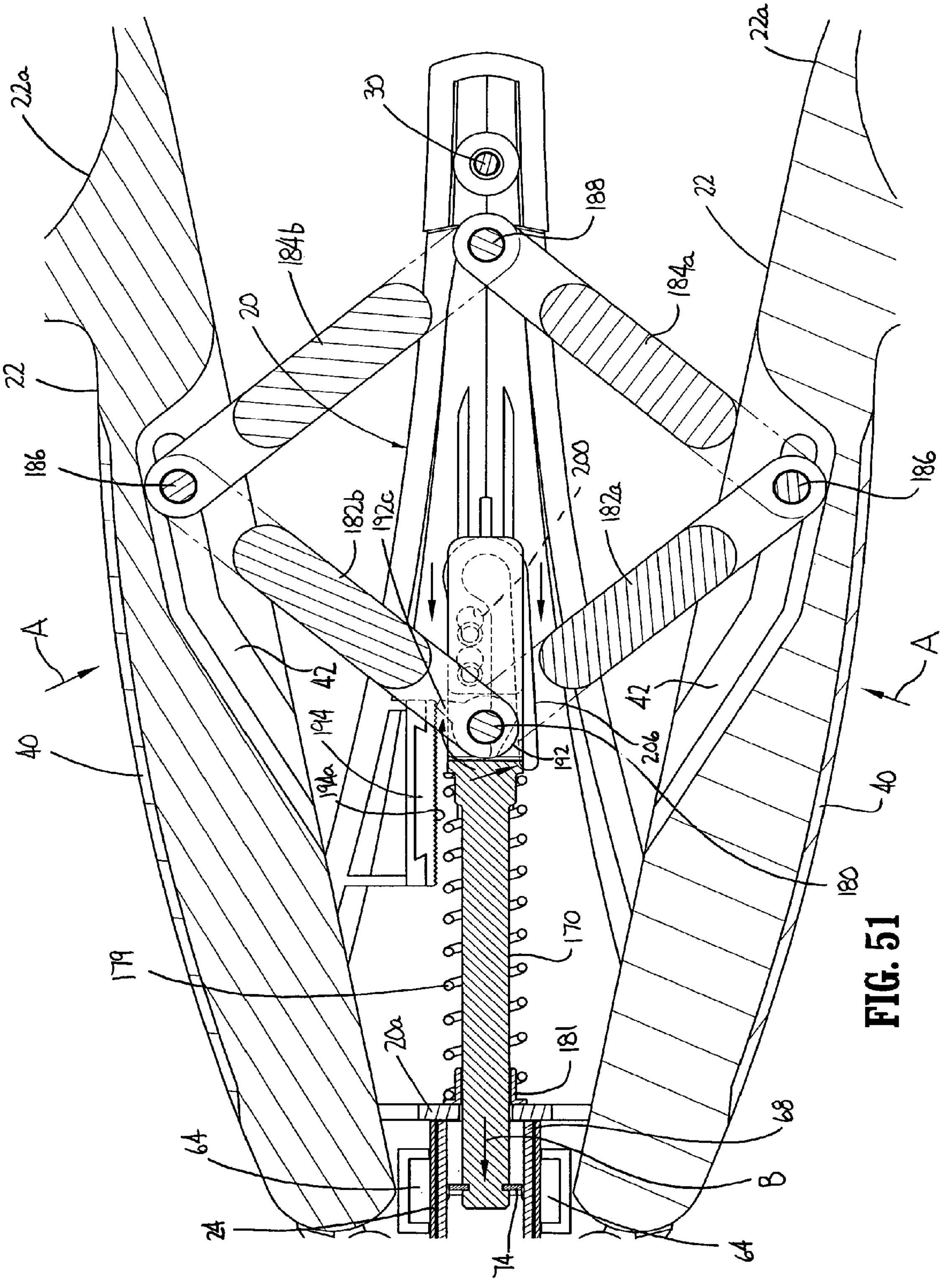
FIG. 51 is a top cross-sectional view of the handle portion of the clip applying apparatus shown in FIG. 1 during initial actuation of the handle portion.

Referring to FIGS. 5, 8, 25 and 28, handle portion 12 includes a yoke 170 which is slidably positioned between housing half-sections 20*a* and 20*b* between retracted and advanced positions. The distal end of yoke 170 includes an annular recess 172 which is dimensioned to be positioned in a semi-circular slot 174 (FIG. 16) formed in bracket 74 of camming member 68 to attach yoke 170 to camming member 68. The proximal end of yoke 170 includes a U-shaped connector 176 having a throughbore 178 dimensioned to receive a pivot pin 180. Pivot pin 180 pivotally connects yoke 170 to the distal end of front links 182*a* and 182*b* of a linkage assembly which connects handles 22 to yoke 170. The proximal end of front links 182*a* and 182*b* are pivotally secured to the distal end of rear links 184*a* and 184*b*, respectively, by pivot members 186. The proximal ends of rear links 184*a* and 184*b* are connected to each other and to handle housing 20 by a pivot member 188. Pivot member 188 is pivotally mounted between bores 190 formed in housing half-sections 20*a* and 20*b* (FIG. 5). Pivot members 186 are received within a respective cam channel 42 formed in a respective handle 22. When handles 22 are actuated, i.e., moved towards housing 20, pivot members 186 are caused to move through cam channels 42 such that front links 182*a*, 182*b* and rear links 184*a*, 184*b* are moved from a first misaligned position towards an aligned position (FIG. 51). Since the proximal end of rear links 184*a* and 184*b* are axially fixed between housing half-sections 20*a* and 20*b*, movement of front links 182*a* and 182*b* and rear links 184*a* and 184*b* toward an aligned position moves the distal end of front links 182*a* and 182*b* distally within housing 20. As discussed above, the distal end of front links 182*a* and 182*b* is axially fixed to yoke 170 by pivot member 180. As such, when handles 22 are actuated, yoke 170 is moved distally to move camming member 68 distally. A biasing member, e.g., coil spring 179, is positioned about a distal end of yoke 170 and abuts a spring stop 181 supported within housing 20 to urge yoke 170 to its retracted position.

Figure 25:
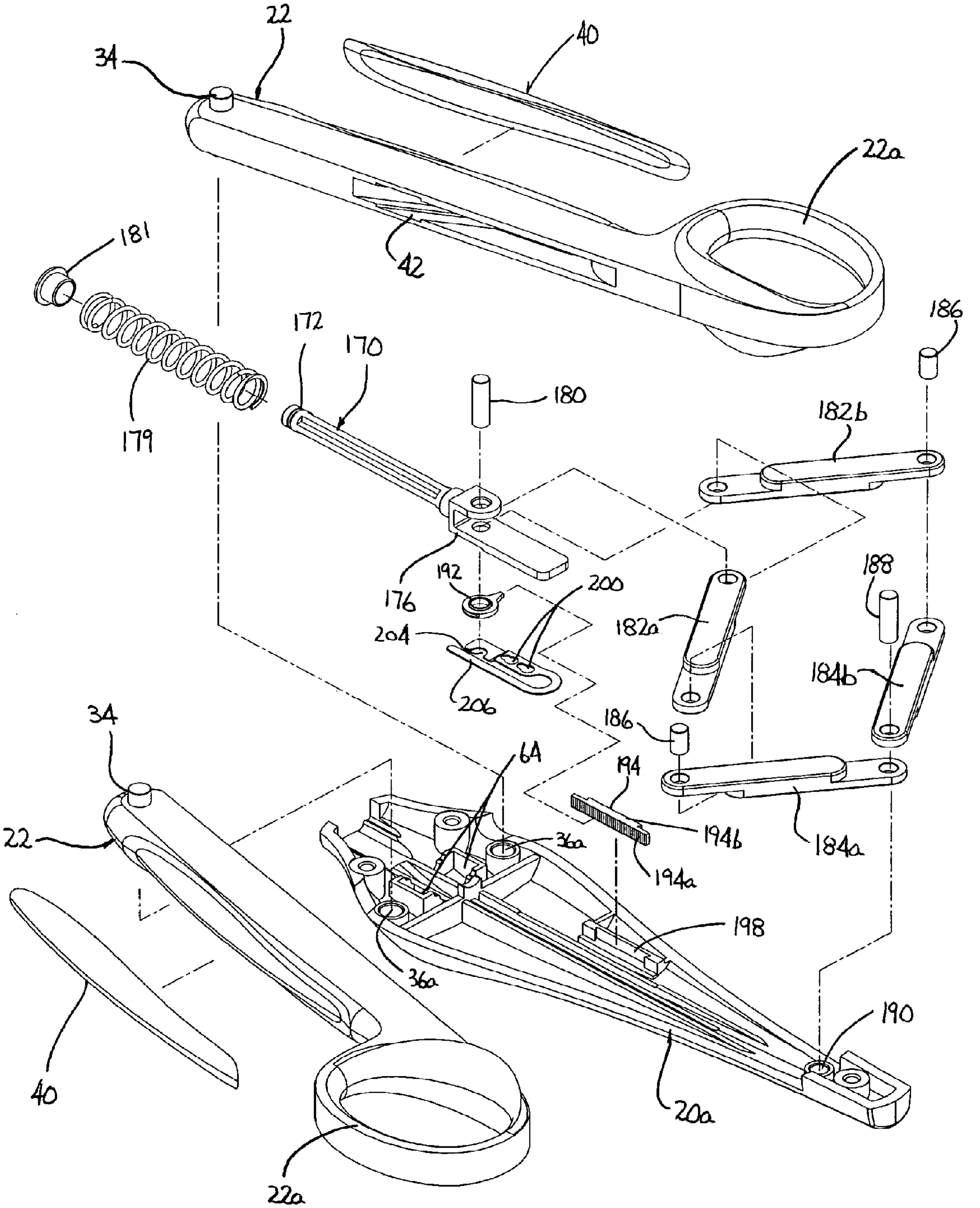
FIG. 25 is an exploded perspective view of the handle portion of the clip applying apparatus shown in FIG. 1.
Figure 26:
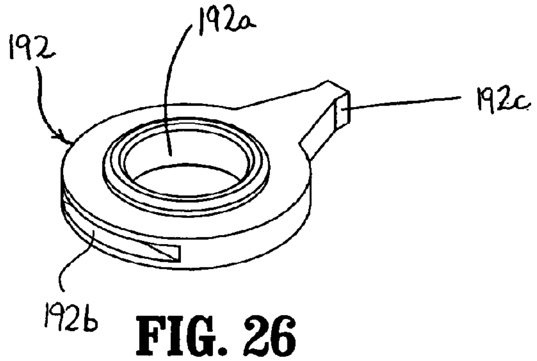
FIG. 26 is a perspective view of the pawl of the handle portion shown in FIG. 25.
Figure 27:
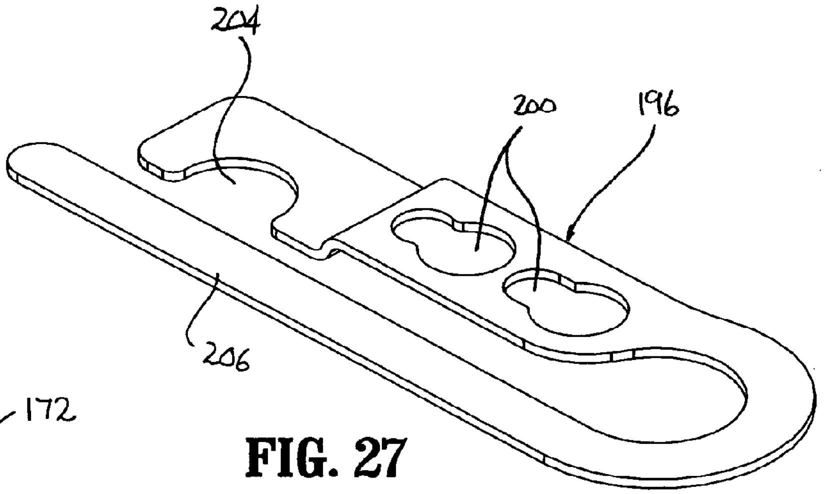
FIG. 27 is a perspective view of the pawl biasing member of the handle portion shown in FIG. 25.
Figure 28:
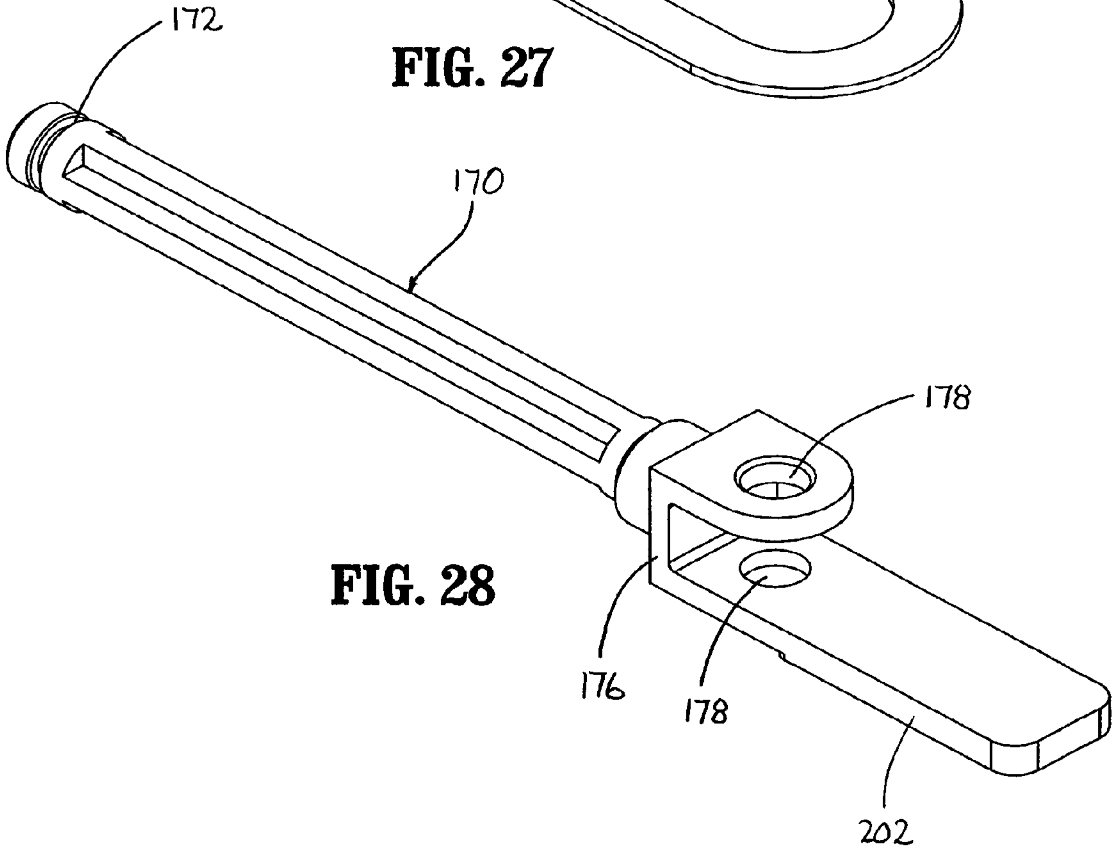
FIG. 28 is a perspective view of the yoke of the handle portion shown in FIG. 25.

Referring to FIGS. 25-27, handle portion 12 includes an anti-reverse ratchet mechanism which includes a pawl 192, a rack 194, and a pawl biasing member 196. Rack 194 includes a series of teeth 194*a* and is supported within a recess 198 formed in housing half-section 20*a*. In one embodiment, recess 198 is dovetail shaped and the backside of rack 194 has a dovetail shape projection 194*b* which is slidably received within recess 198 to secure rack 194 within housing 20. Alternately, other fastening techniques can be used to secure rack 194 within housing 20, e.g., adhesives, pins, welding, etc.

Pawl 192 includes a bore 192*a* dimensioned to receive pivot member 180 such that pawl 192 is rotatably mounted to yoke 170 about pivot member 180. Pawl biasing member 196 includes a pair of mounting holes 200 for securing bracket 196 to a plate extension 202 (FIG. 28) of yoke 170. Pawl biasing member 196 also includes a semi-circular cutout 204 which is positioned to be clipped partially about pivot member 180, and a cantilever or spring arm 206 which is positioned within a slot 192*b* formed in a backside of pawl 192. Cantilever arm 206 is resilient and provides a biasing force to urge pawl 192 to a position in which pawl finger 192*c* is substantially perpendicular to arm 206. Finger 192*c* is positioned to engage teeth 194*a* of rack 194 to retain yoke 170 at partially advanced positions during actuation of clip applier 10 against the bias of spring 179 which urges yoke 170 to its retracted position. The anti-reverse ratchet mechanism prevents retraction of yoke 170 and camming member 68 after handles 22 have been partially actuated until the clip applier has been fully actuated.

Figure 36:
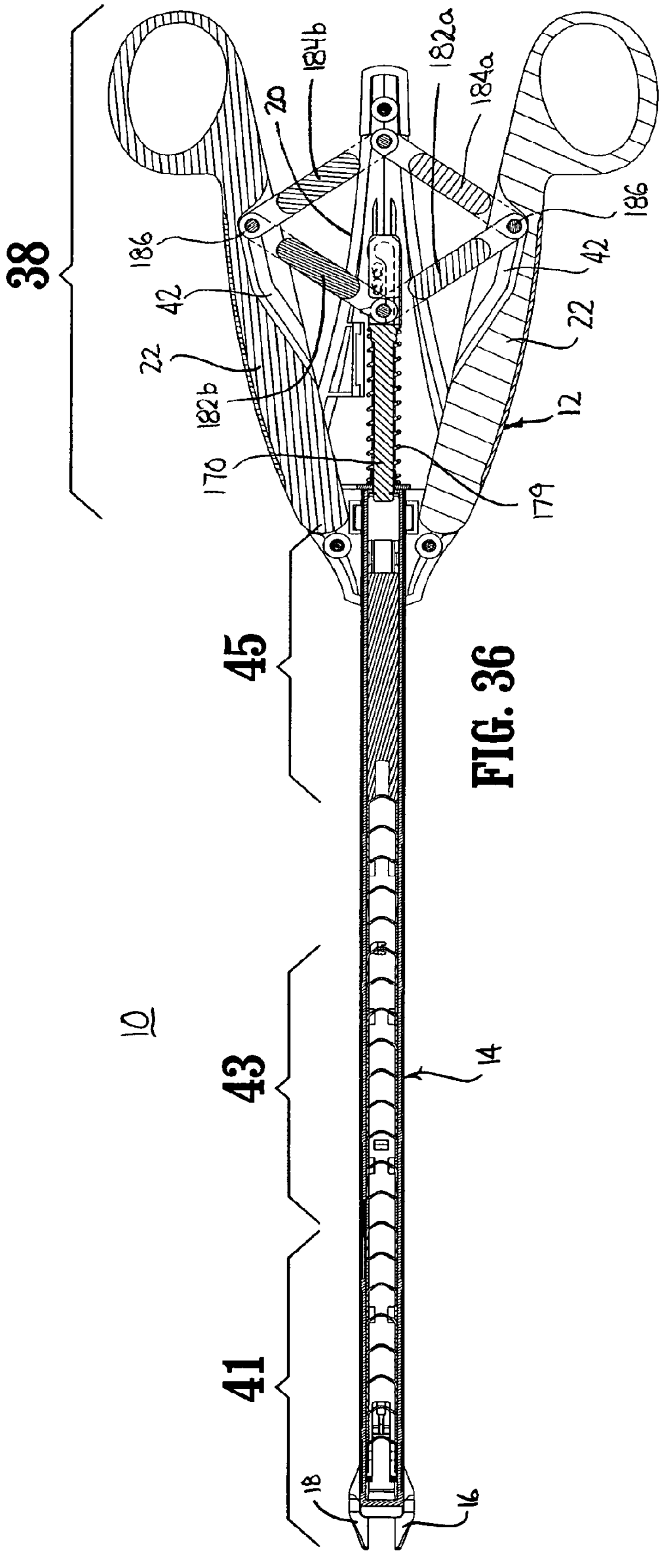
FIG. 36 is a top cross-sectional view of the clip applying apparatus shown in FIG. 1 prior to actuation of the apparatus.
Figure 37:
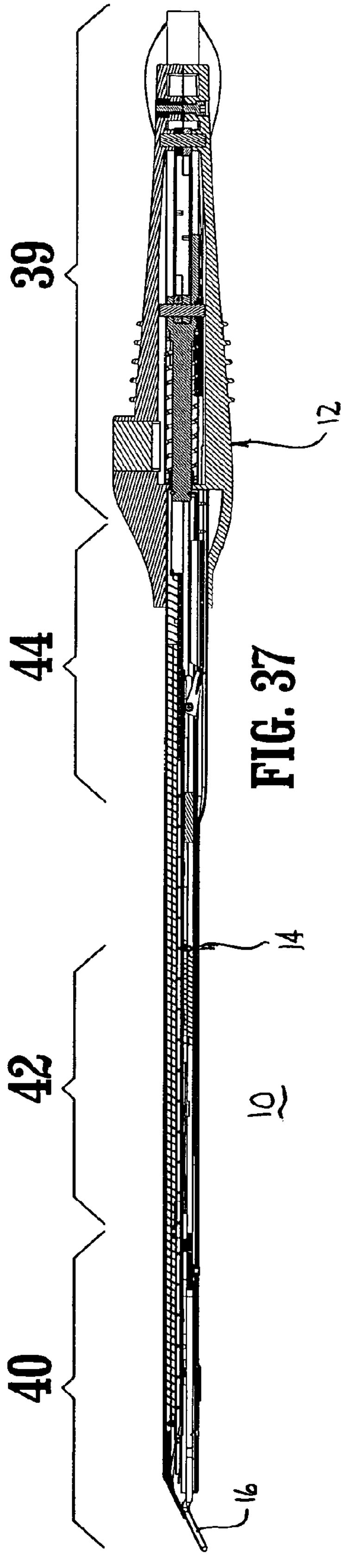
FIG. 37 is a side cross-sectional view of the clip applying apparatus shown in FIG. 36.
Figure 38:
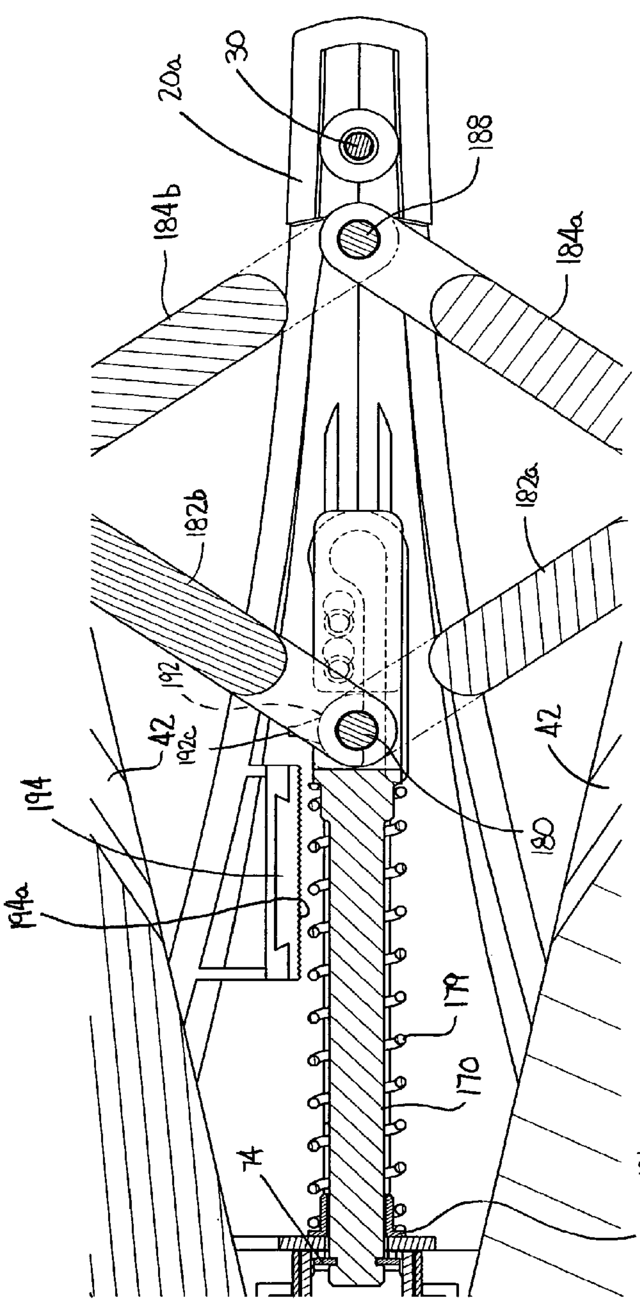
FIG. 38 is an enlarged view of the indicated area of detail shown in FIG. 36.
Figure 39:
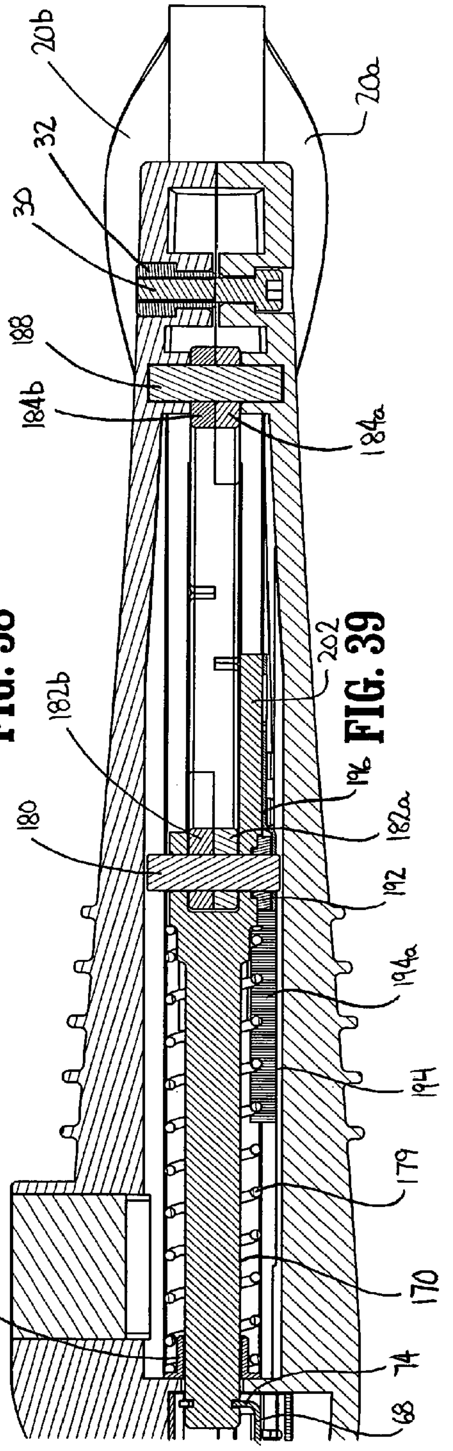
FIG. 39 is an enlarged view of the indicated area of detail shown in FIG. 37.
Figure 40:
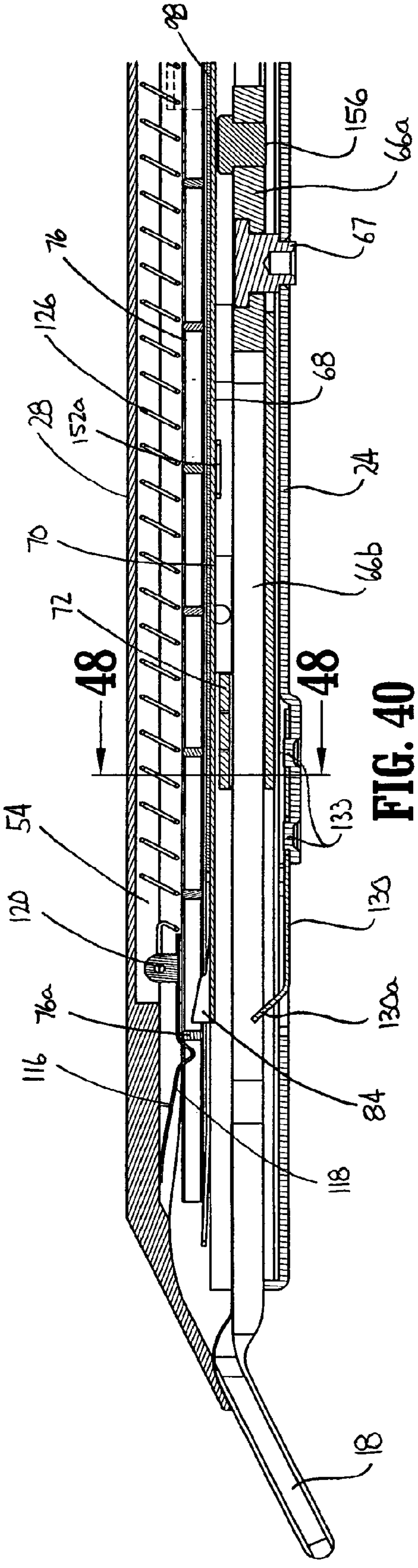
FIG. 40 is an enlarged view of the indicated area of detail shown in FIG. 37.
Figure 41:
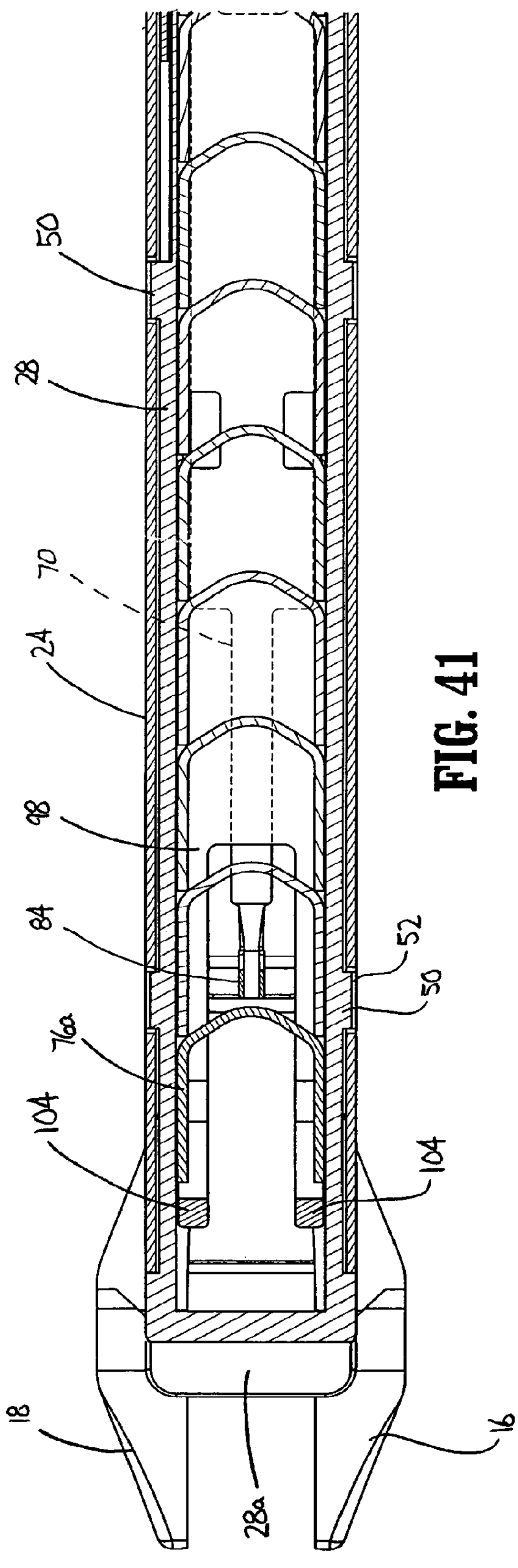
FIG. 41 is an enlarged view of the indicated area of detail shown in FIG. 36.
Figure 42:
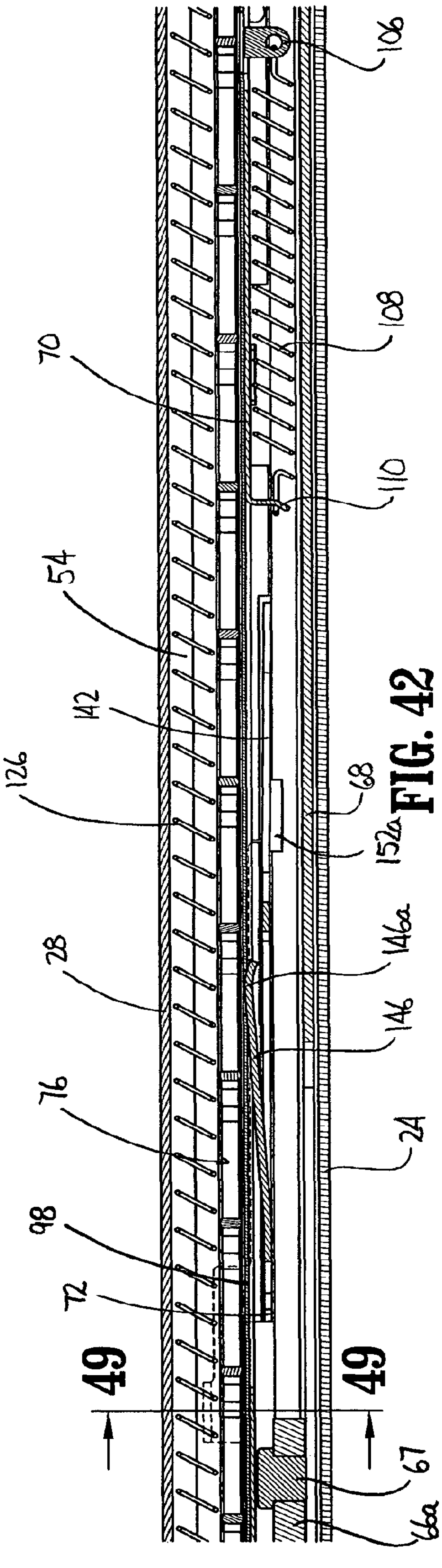
FIG. 42 is an enlarged view of the indicated area of detail shown in FIG. 37.
Figure 43:
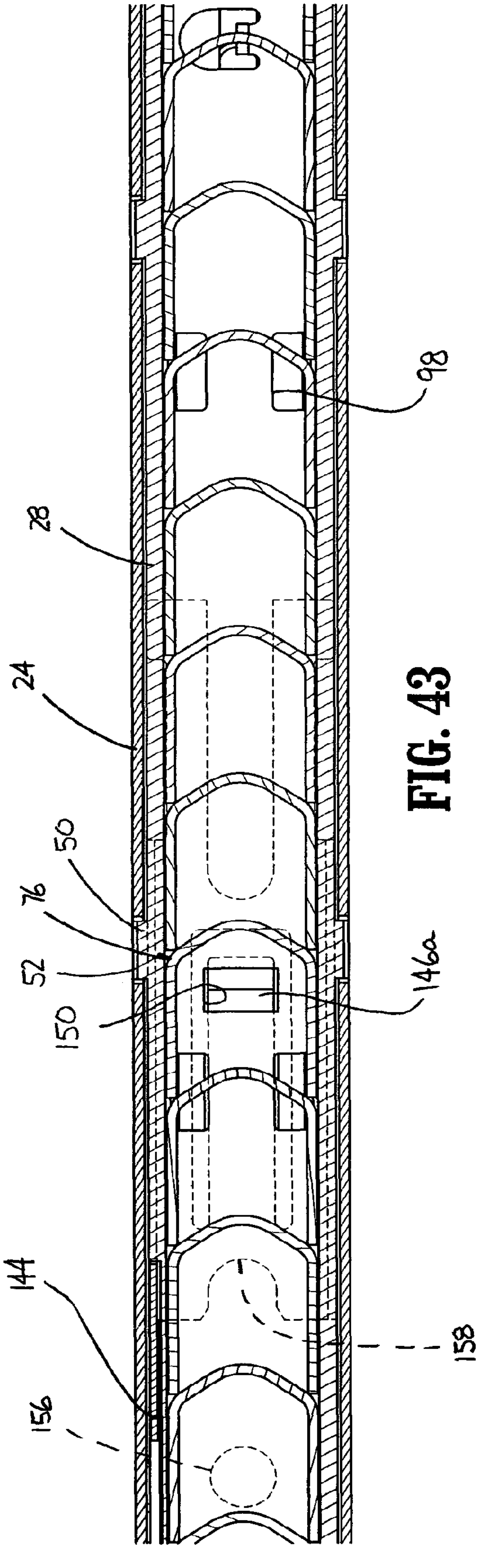
FIG. 43 is an enlarged view of the indicated area of detail shown in FIG. 36.
Figure 44:
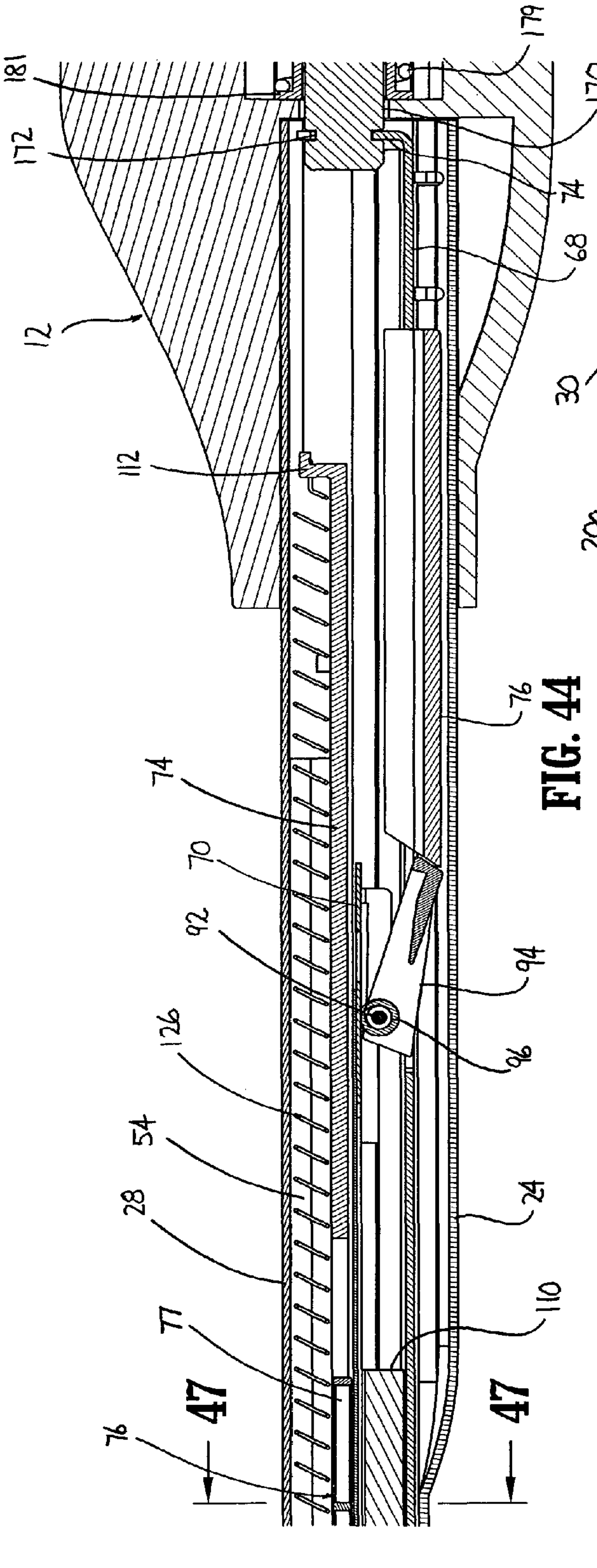
FIG. 44 is an enlarged view of the indicated area of detail shown in FIG. 37.
Figure 45:
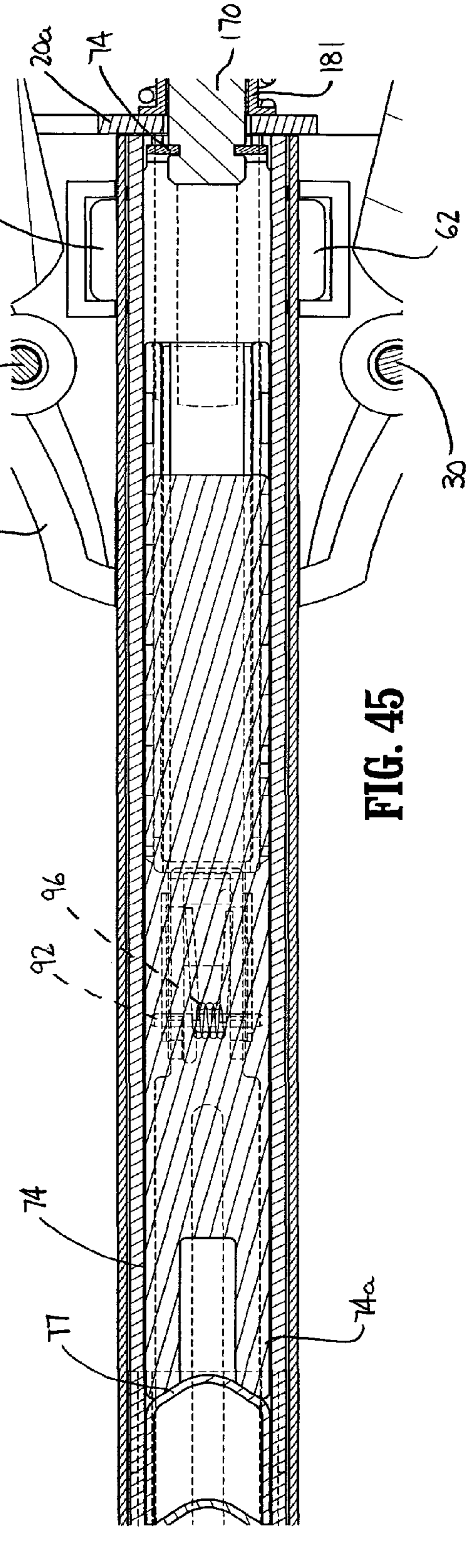
FIG. 45 is an enlarged view of the indicated area of detail shown in FIG. 36.

Referring to FIGS. 36-67, operation of clip applier 10 will now be described. FIGS. 36-50 illustrate clip applier 10 prior to actuation of handles 22, i.e., in the prefired position. In the prefired position, biasing member 179 urges yoke 170 to its retracted position. When yoke 170 is in its retracted position, pivot members 186 are positioned within cam channels 42 (FIG. 36) such that front links 182*a* and 182*b* and rear links 184*a* and 184*b* are in their misaligned position, handles 22 are spaced from housing 20 of clip applier 10, and pawl 192 (FIG. 38) is positioned proximally of rack 194 (FIG. 38). Referring to FIGS. 40-50, in the prefired position, camming member 68 is urged to its retracted position by yoke 170 and biasing member 179 (FIG. 39). Clip pusher 70 is urged to its retracted position by biasing member 108 (FIG. 42). Clip stack 76 is urged by follower 74 (FIG. 44) and biasing member 126 distally within body 14, but distal-most clip 76*a* is prevented from moving into jaws 16 and 18 by spring arm 118 of clip stop member 116 (FIG. 40). Jaw locking plate 130 is positioned between jaw legs 66*b* to prevent inadvertent closure of jaws 16 and 18 (FIG. 40). It is also noted that latch member 94 of pusher latch assembly 80 is spaced distally of but in a position to engage abutment member 79 which is supported on camming member 68 (FIG. 44). Further, radial projections 142*a* of lockout 72 are positioned proximally of slots 152*a* of camming member 68 and recess 158 of lockout 72 is positioned proximally of stop member 156.

Figure 52:
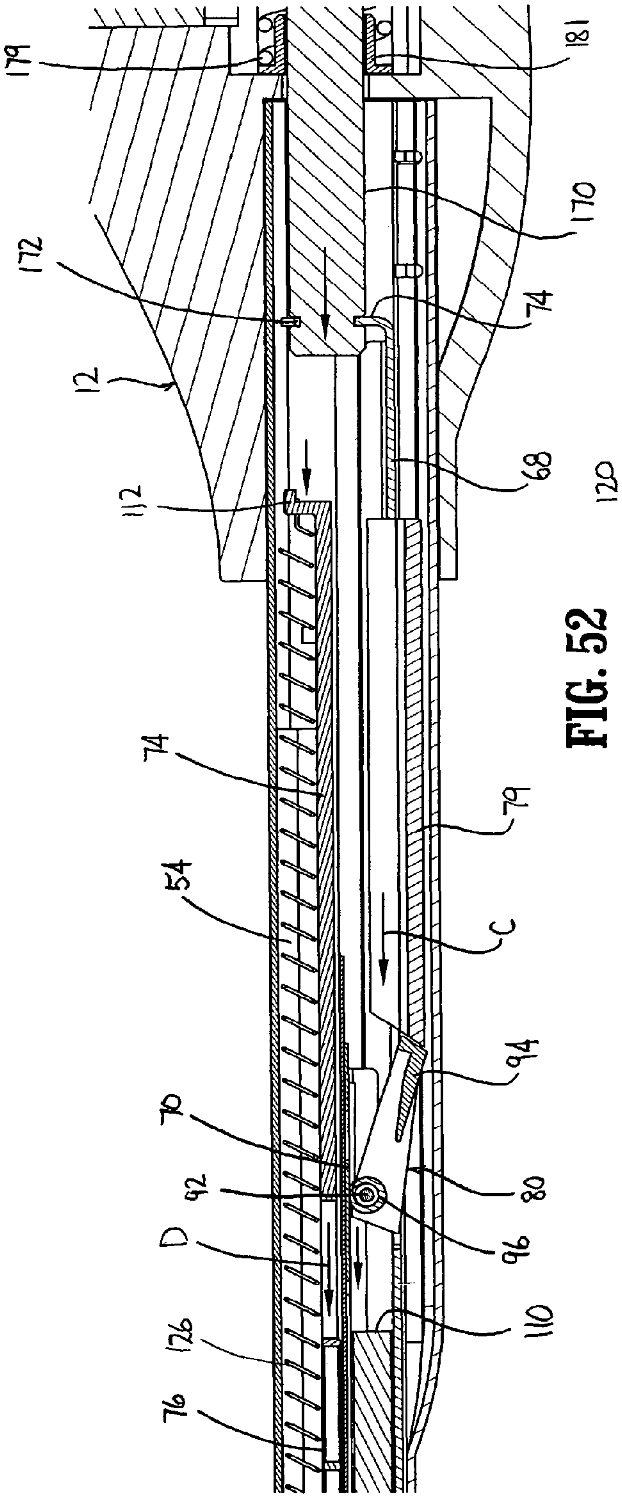
FIG. 52 is a side cross-sectional view of the proximal portion of the body portion of the clip applying apparatus shown in FIG. 1 during initial actuation of the handle portion.

FIGS. 51-63 illustrate clip applier 10 in various stages of operation. Referring to FIG. 51, handles 22 have been partially actuated or moved towards housing 20 in the direction indicated by arrow "A". Actuation of handles 22 moves front links 182*a* and 182*b* towards their aligned position to advance yoke 170 distally in the direction indicated by arrow "B". Referring to FIG. 52, as yoke 170 is advanced, camming member 68 which is secured to yoke 170 is advanced distally within elongated body 14 of clip applier 10. Abutment member 79 is supported on camming member 68 and is also advanced distally within elongated body 14 in the direction indicated by arrow "C". During the initial actuation stroke of handles 22, abutment member 79 engages latch member 94 of pusher latch assembly 80 to effect advancement of clip pusher 70 in the direction indicated by arrow "D". Referring to FIG. 53, as clip pusher 70 advances, engagement finger 84 of clip pusher 70 advances distal-most clip 76*a* of clip stack 76 past spring arm 118 of clip stop member 116 into jaws 16 and 18. As the distal-most clip 76*a* of clip stack 76 is advanced into the jaws, follower 74 (FIG. 52) under the force of biasing member 126 advances clip stack 76 distally in the direction indicated by arrow "E" in FIG. 53 to position the second distal-most clip 77 adjacent clip stop member 116 (See FIGS. 53-55).

Figure 55:
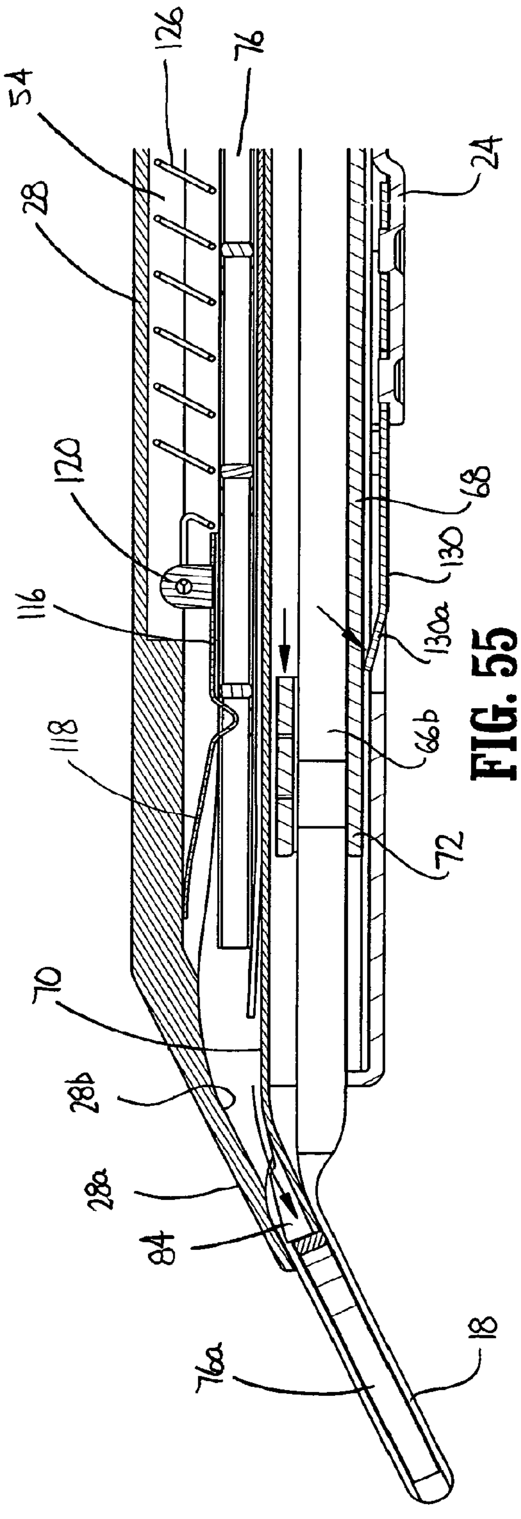
FIG. 55 is a side cross-sectional view of the distal end of the body portion of the clip applying apparatus shown in FIG. 1 during further actuation of the handle portion.
Figure 56:
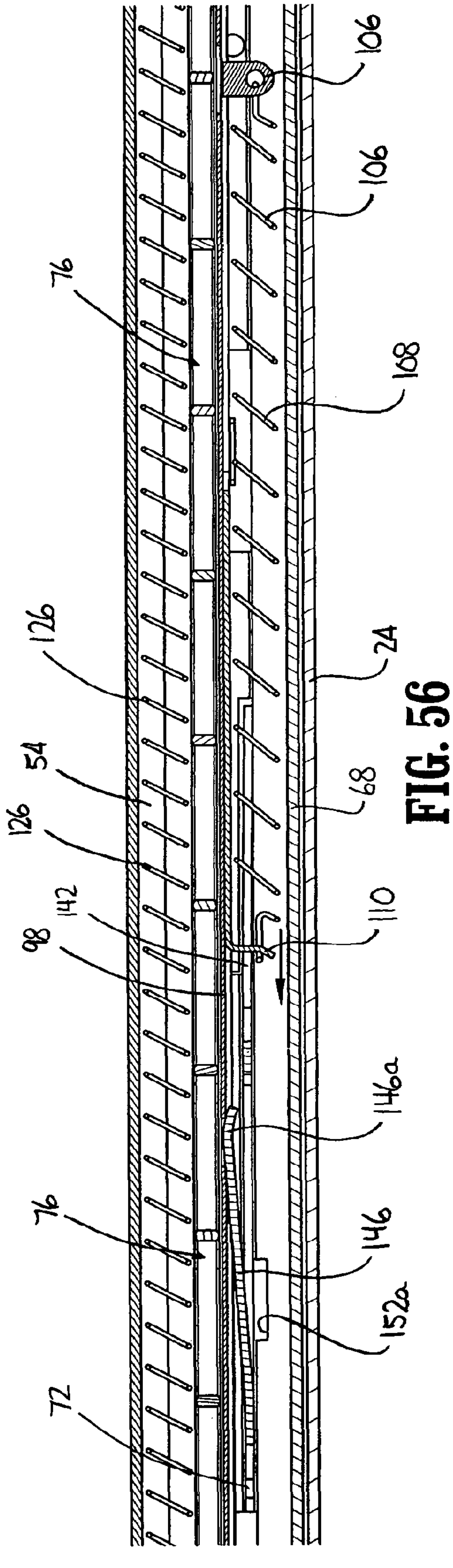
FIG. 56 is a side cross-sectional view of the body portion shown in FIG. 42 after further actuation of the handle portion.
Figure 57:
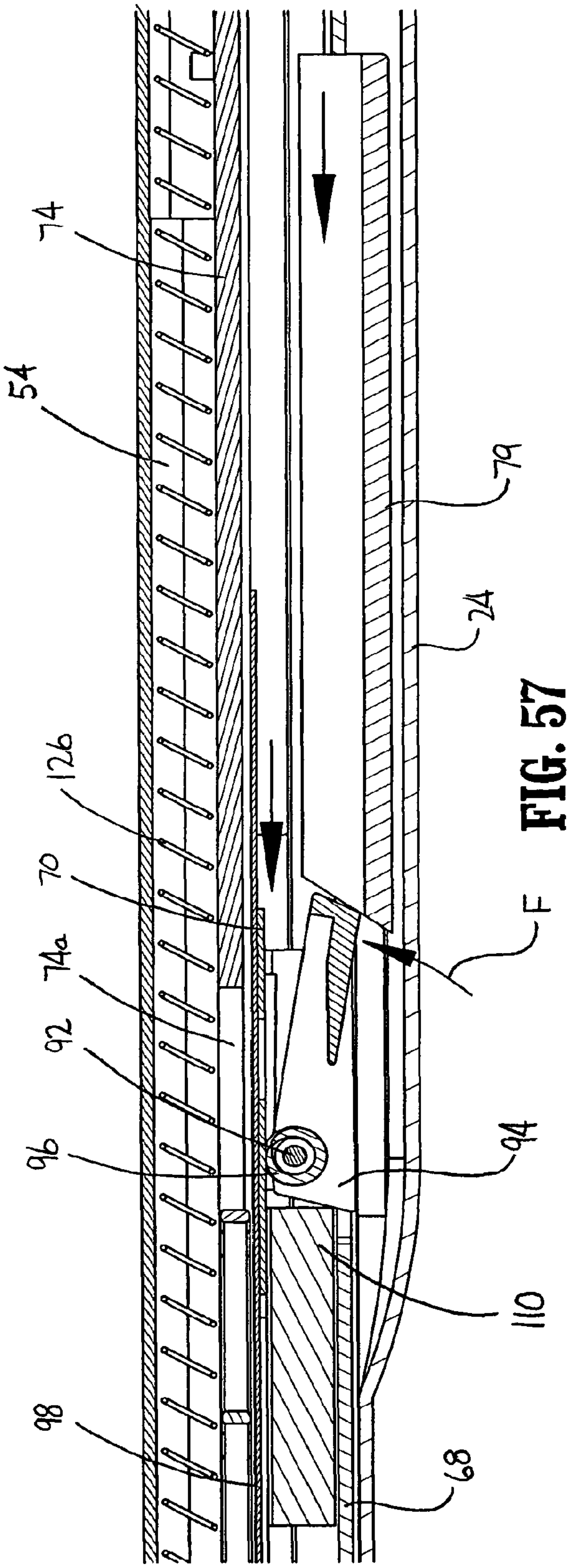
FIG. 57 is a side cross-sectional view of the body portion shown in FIG. 44 after further actuation of the handle portion.
Figure 58:
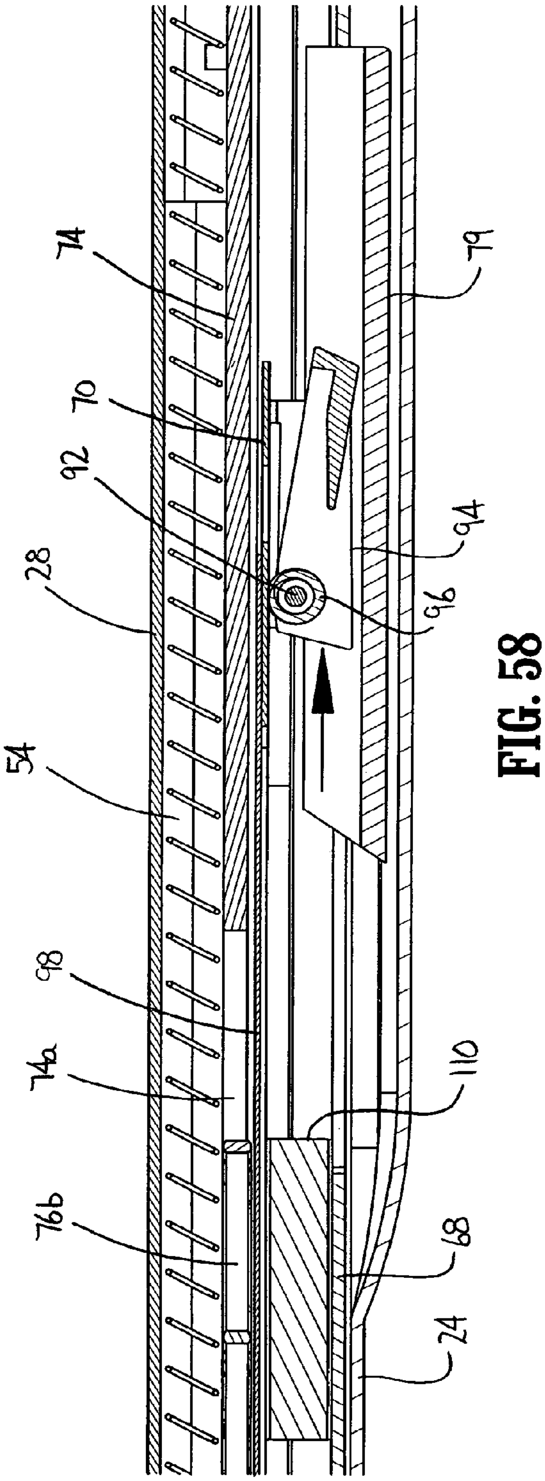
FIG. 58 is a side cross-sectional view of the body portion shown in FIG. 57 after further actuation of the handle portion.

Referring to FIGS. 55-57, as camming member 68 and clip pusher 70 advance within elongated body 14, the tension in spring 108 is increased, i.e., spring 108 is stretched (FIG. 56). When distal-most clip 76*a* is fully positioned within jaws 16 and 18, pusher latch cam 110 engages a distal end of latch member 94 and pivots latch member 94 in the direction indicated by arrow "F" against the urging of biasing member 96 to release latch member 94 from abutment member 79. When latch member 94 is released from abutment member 79, biasing member 108 returns clip pusher 70 to its retracted position (FIGS. 58 and 59).

As handles 22 are more fully actuated, i.e., moved closer to housing 20, camming member 68 engages finger 130*a* of jaw locking plate 130 (FIG. 55) to deform plate 130 downwardly from between legs 66*b* of jaw body 66. Continued advancement of camming member 68 advances engagement member 72 into camming surfaces 70 of jaws 16 and 18 to move jaws 16 and 18 from a spaced position (FIG. 46) to a crimping position (FIG. 63).

Referring to FIG. 51, as yoke 170 is moved from its retracted position within housing 20 to its advanced position, a finger 192*c* of pawl 192 engages teeth 194*a* of rack 194 to prevent spring 179 from returning yoke 170 to its retracted position when handles 22 are released. As such, once handles 22 begin to be actuated and pawl 192 engages rack 194 (FIG. 51) yoke 170 cannot be returned to its retracted position until clip applier 10 is fully actuated. When yoke 170 is moved to its advanced position, pawl 192 passes by the distal end of rack 194 (FIG. 61) and cantilevered or spring arm 206 of pawl biasing member 196 will rotate pawl 192 in the direction indicated by arrow "G" in FIG. 61 to a position in which finger 192*a* of pawl 192 is positioned at 12:00. Thus, when handles 22 are released and spring 179 returns yoke 170 to its retracted positioned (FIG. 64) finger 192*c* will engage the distal end of rack 194 and rotate counter-clockwise in the direction indicated by arrow "H" in FIG. 64 and ratchet over teeth 194*a* of rack 194. Note, in the fully retracted position of yoke 170, pawl 192 is positioned proximally of rack 194. In this position cantilevered arm 206 (FIG. 61) returns finger 192*c* of pawl 192 to the 12:00 position.

Figure 61:
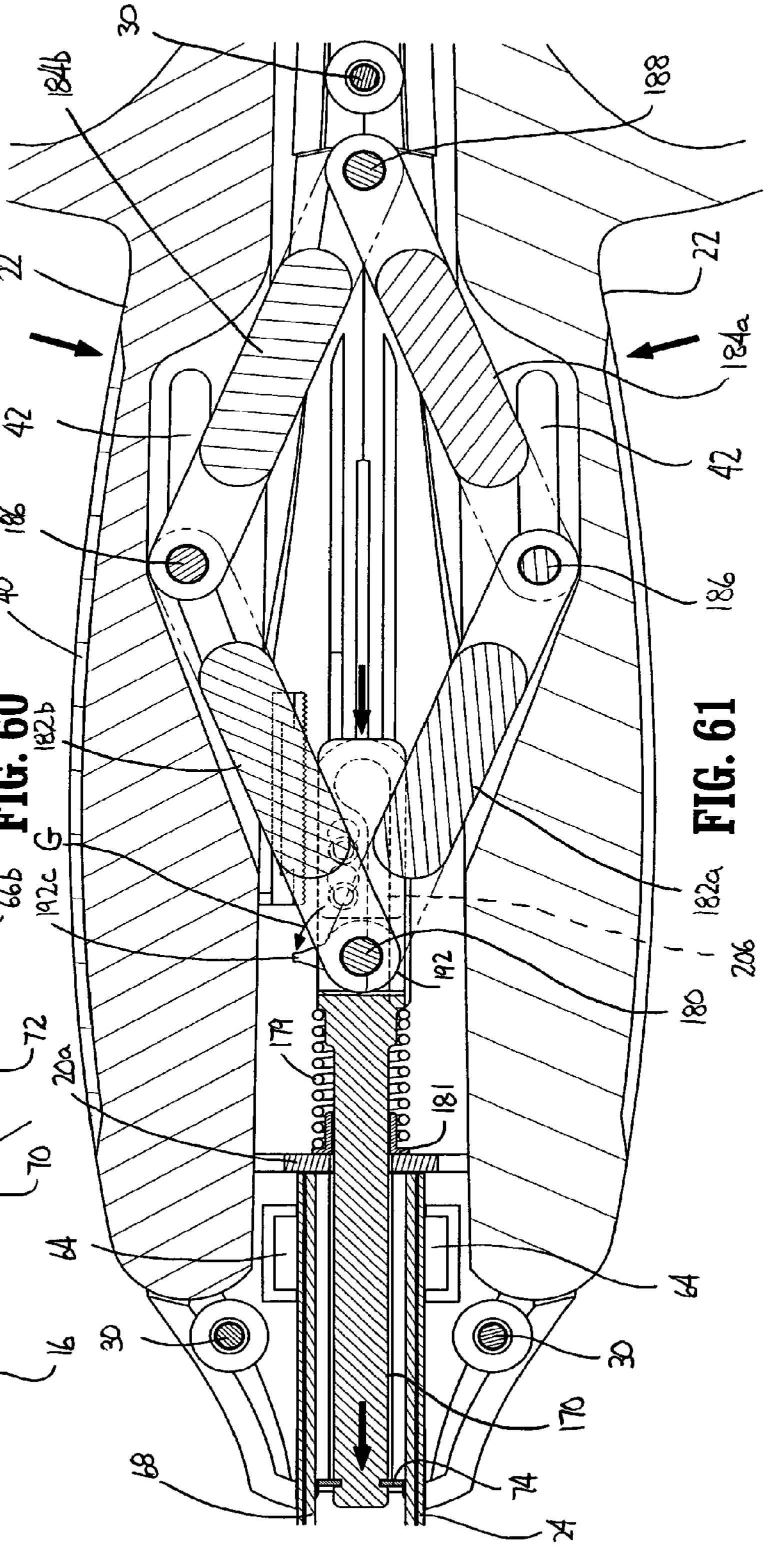
FIG. 61 is a top cross-sectional view of the handle portion shown in FIG. 51 with the handle portion after further actuation of the handle portion.
Figure 62:
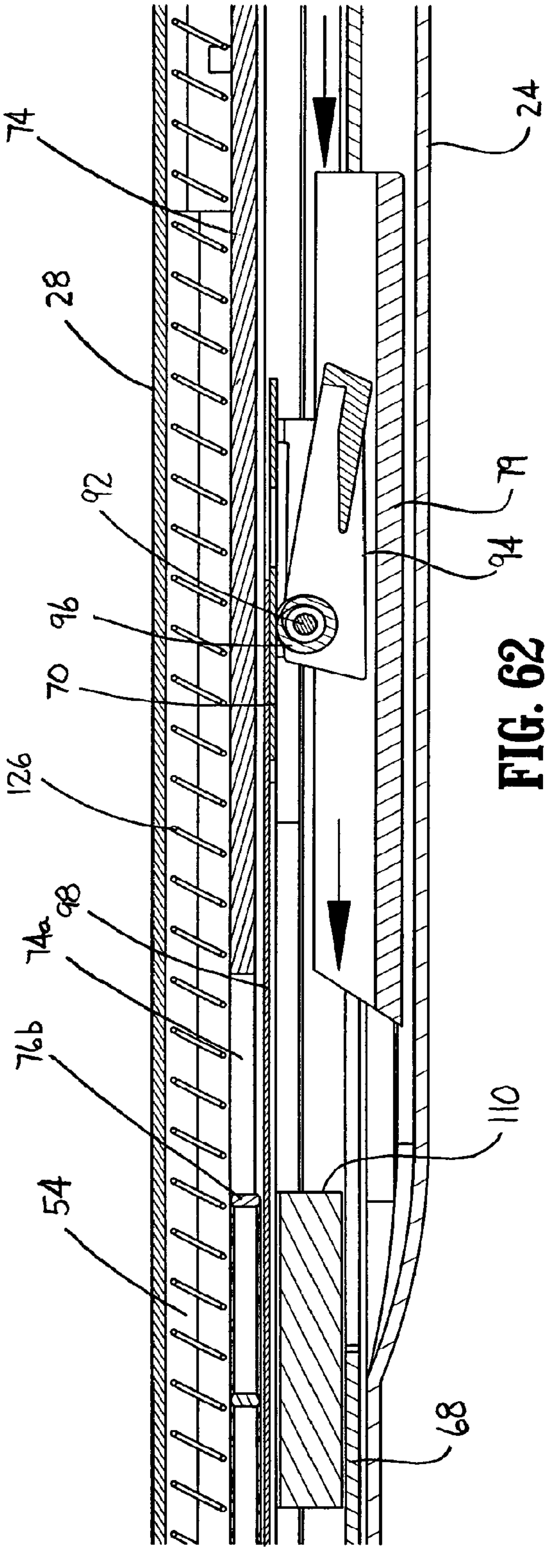
FIG. 62 is a side cross-sectional view of the body portion shown in FIG. 58 after further actuation of the handle portion.
Figure 63:
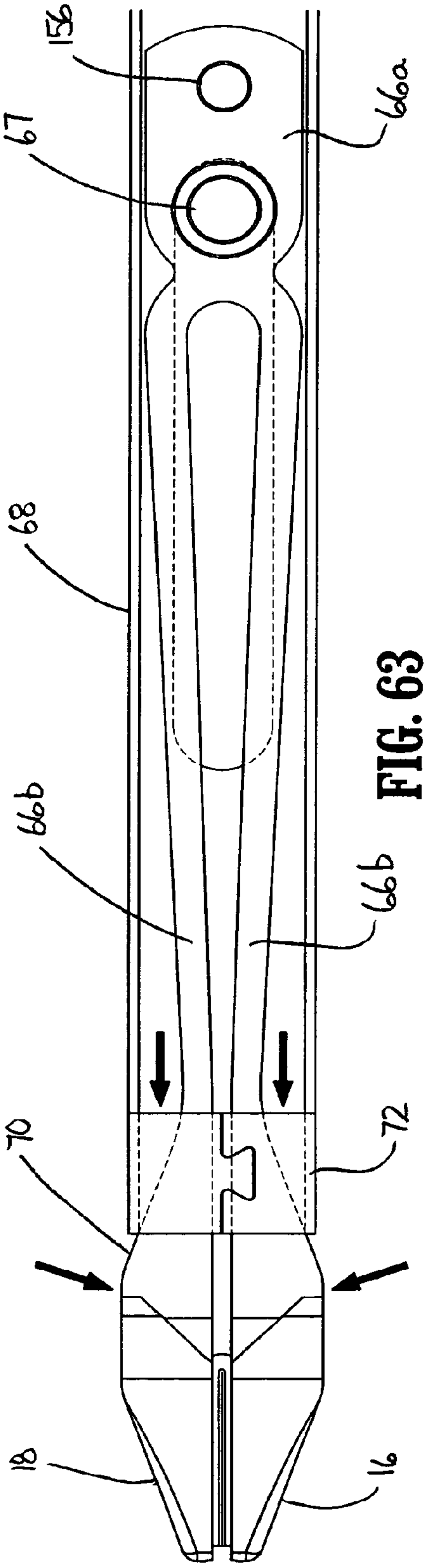
FIG. 63 is a top view of the jaw body and camming member shown in FIG. 60 with camming member fully advanced.
Figure 64:
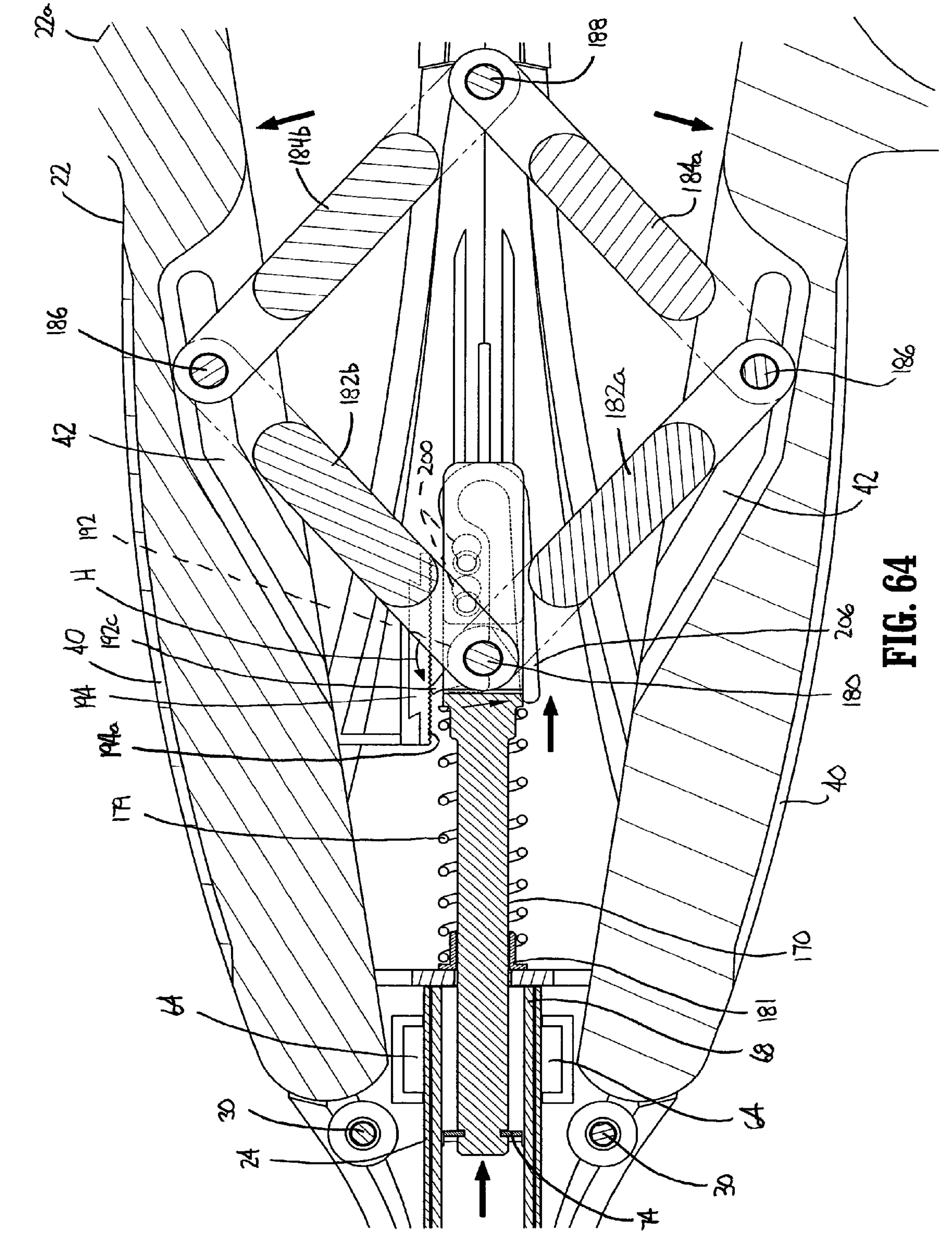
FIG. 64 is a top cross-section view of the handle portion shown in FIG. 61 after the handle portion has been returned to the unactuated position.

After the device has been fully actuated as shown in FIGS. 61-63 and handles 22 have been released, yoke 170 is moved to its retracted position by spring 179. Camming member 68, which is secured to yoke 170, is also moved toward its retracted position. As this occurs, resilient jaws 16 and 18 return to their spaced position and camming member 68 moves past jaw locking plate 130 allowing locking plate finger 130*a* to return to a position located between legs 66*b* of jaw body 66. As discussed above, the positioning of locking plate 130 between legs 66*b* of jaw body 66 prevents inadvertent closure of jaws 16 and 18.

Figure 65:
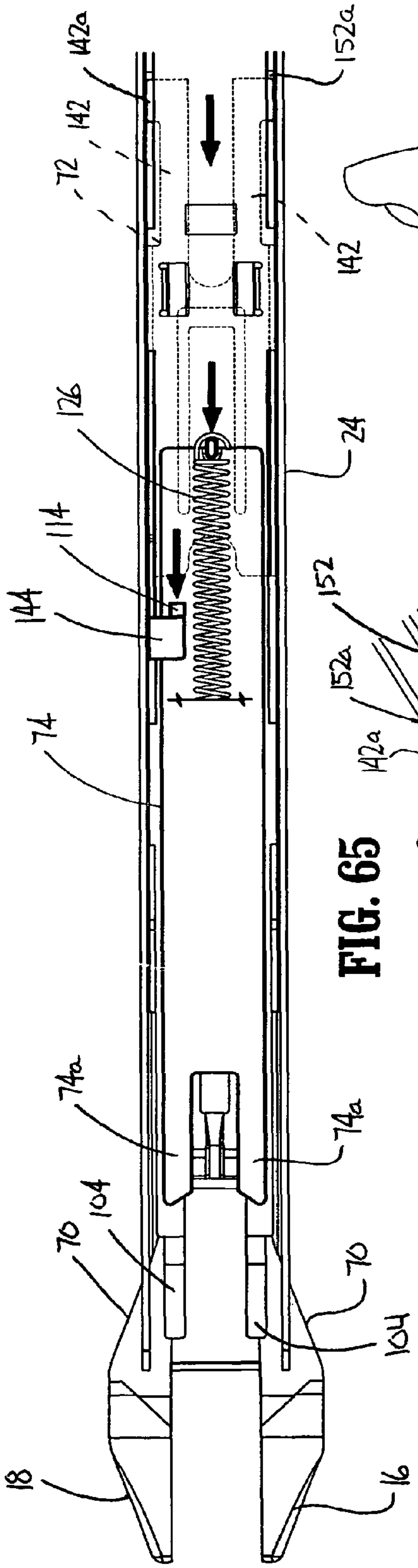
FIG. 65 is a top view of the distal portion of the body portion of the clip applying apparatus shown in FIG. 36 illustrating the lockout tab of the clip follower engaging the engagement member of the lockout.
Figure 66:
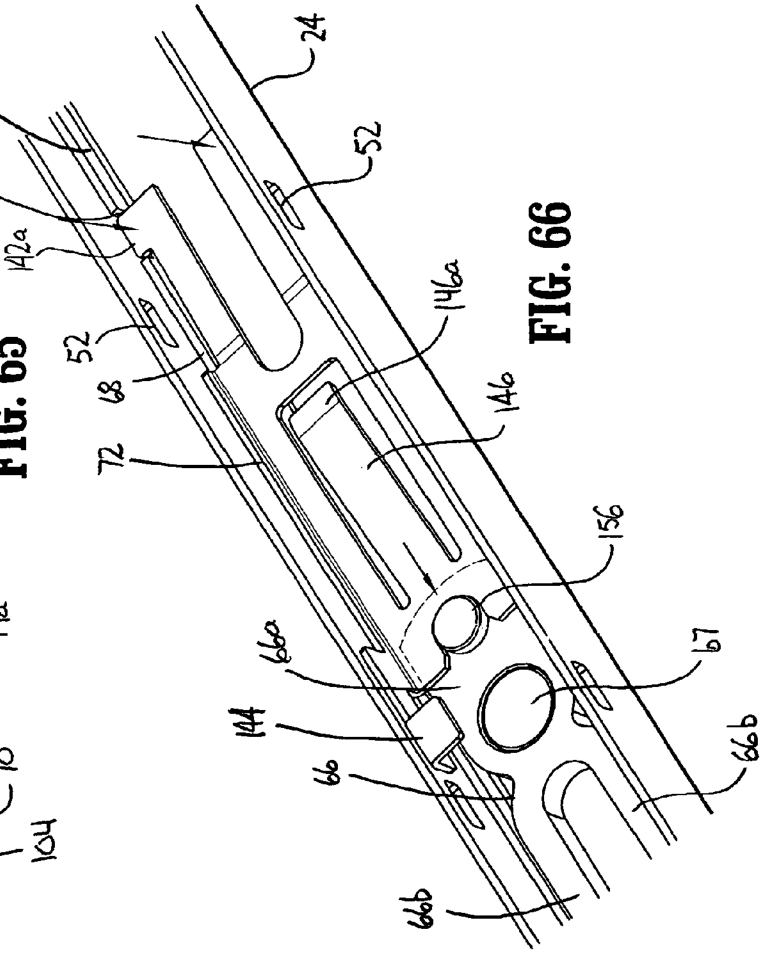
FIG. 66 is top perspective view of a portion of the body portion of the clip applying apparatus shown in FIG. 36 illustrating the lockout engaging the stop member.
Figure 67:
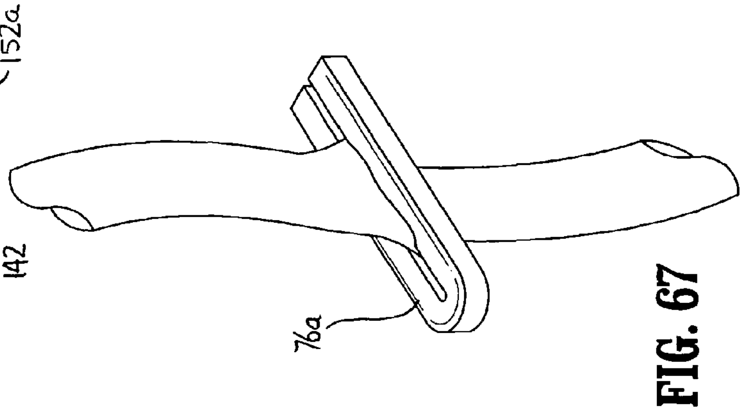
FIG. 67 is a perspective view of a clip of the clip stack of the clip applying apparatus shown in FIG. 36 deformed about tissue.

Referring to FIGS. 65 and 66, after the proximal-most clip 76*b* has been advanced beyond clip stop member 116, clip follower 74 is advanced towards its fully advanced position by biasing member 126. As this occurs, lockout tab 114 formed on follower 74 engages engagement member 144 of lockout 72 to advance lockout 72 distally in relation to camming member 68 to move radial projections 142*a* of flexible legs 142 of lockout 72 into slots 152*a* of camming member 68 and secure or interlock lockout 72 to camming member 68. When lockout 72 is moved distally within elongated body 14 by follower 74, distal recess 158 of lockout 72 receives stop member 156, which is secured to mounting portion 66*a* of jaw body 66 such that the distal end of lockout 72 engages stop member 156. Engagement between the distal end of lockout 72 and stop member 156 prevents further distal movement of lockout 72 and, thus, camming member 68.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

What is claimed is:

1. An apparatus for applying surgical clips, comprising:

- a body portion;
- a pair of jaw members extending distally from the body portion;
- a clip stack housed within the body portion and including a distal-most clip;
- a clip pusher movably positioned within the body portion to advance the distal-most clip from the clip stack to a position between the pair of jaw members;
- a camming member movably positioned within the body portion to approximate the pair of jaw members to form the distal-most clip positioned between the pair of jaw members;
- a lockout member including a central body portion defining a recess, the lockout member being movable from a first position in slidable relation to the camming member to a second position interlocked with the camming member such that the lockout member and the camming member move in unison with one another; and
- a stop member configured to abut the recess of the lockout member to limit distal movement of the camming member while the lockout member is in the second position.

2. The apparatus according to claim 1, wherein the lockout member includes at least one flexible leg having a projection and the camming member includes at least one slot dimensioned to receive the projection to interlock the lockout member to the camming member.

3. The apparatus according to claim 2, wherein the at least one flexible leg includes a pair of flexible legs and the at least one slot includes a pair of slots.

4. The apparatus according to claim 2, further including a clip follower operable to urge the clip stack distally towards the pair of jaw members, the clip follower including a tab, the lockout member including an engagement member that extends distally from a distal end of the lockout member, the tab of the clip follower being movable into the engagement member to move the lockout member from the first position to the second position.

5. The apparatus according to claim 4, wherein while the lockout member is disposed in the second position, the lockout member and the camming member are positioned to simultaneously move distally.

6. The apparatus according to claim 1, wherein the lockout member includes a resilient finger positioned to releasably retain the lockout member in the first position.

7. The apparatus according to claim 6, wherein the body portion further includes a separator plate, the separator plate defining an opening dimensioned to receive a portion of the resilient finger of the lockout member.

8. The apparatus according to claim 1, further including a clip follower operable to urge the clip stack distally towards the pair of jaw members, the lockout member including at least one flexible leg having a projection, the camming member including at least one slot, and the clip follower including at least one tab that is movable into an engagement member that extends distally from a central body portion of the lockout member, wherein engagement of the at least one tab with the engagement member moves the lockout member to the second position so that the projection of the at least one flexible leg is received by the at least one slot of the camming member to interlock the lockout member to the camming member.

9. The apparatus according to claim 1, wherein the lockout member defines a plane in the first position, the lockout member being movable along and remaining within the plane as the lockout member moves from the first position to the second position.

10. An apparatus for applying surgical clips, comprising:

- a handle portion including at least one movable handle;
- a body portion including a clip pusher and a camming member, the clip pusher being movably supported within the body portion to advance a distal-most clip of a clip stack to a position between a pair of jaw members supported at a distal end of the body portion, the camming member being movably supported within the body portion for movement from a retracted position to an advanced position to approximate the pair of jaw members; and
- a latch assembly supported on the clip pusher, the latch assembly including a pivotal latch member that is movable from a first position to engage an abutment supported on the camming member to a second position to disengage from the abutment of the camming member;
- wherein the camming member is operably connected to the at least one movable handle such that movement of the at least one movable handle through an actuation stroke effectuates movement of the camming member from the advanced position to the retracted position.

11. The apparatus according to claim 10, wherein the pivotal latch member is urged towards the first position by a biasing member such that movement of the camming member from the retracted position to the advanced position initially effectuates advancement of the clip pusher.

12. The apparatus according to claim 11, further including a latch cam fixedly supported on the body portion, the latch cam being positioned to engage the pivotal latch member after the clip pusher advances the distal-most clip of the clip stack to the position between the pair of jaw members to disengage the latch member from the abutment of the camming member.

13. The apparatus according to claim 12, further including a biasing member positioned to urge the clip pusher to a retracted position after the latch member is disengaged from the abutment of the camming member.

14. The apparatus according to claim 13, wherein the body portion includes a housing body and a housing cover, the latch cam being supported on the housing cover.

15. The apparatus according to claim 10, wherein the handle portion includes a yoke that is connected to a proximal end of the camming member, the at least one moveable handle being operably connected to the yoke by at least one front link such that movement of the at least one moveable handle through an actuation stroke effectuates advancement of the yoke and the camming member.

16. The apparatus according to claim 15, wherein the at least one moveable handle of the handle portion includes a pair of handles, each of the pair of handles being operably connected to the yoke by the at least one front link.

17. The apparatus according to claim 16, further including a pair of rear links, each of the rear links having a first end pivotally connected to a respective front link by a first pivot member and a second end pivotally connected to the handle portion by a second pivot member.

18. The apparatus according to claim 17, wherein each of the pair of handles defines a cam channel for slidably receiving a respective one of the first pivot members.

19. An apparatus for applying surgical clips, comprising:

a handle portion;

a body portion extending distally from the handle portion; and a jaw body supported at a distal end of the body portion, the jaw body including first and second jaw members movable from a spaced position to an approximated position;

wherein the body portion includes a camming member movable from a retracted position to an advanced position to effectuate movement of the first and second jaw members from the spaced position to the approximated position, the body portion further including a resilient jaw locking member removably positioned between the first and second jaw members to prevent the first and second jaw members from moving from the spaced position to the approximated position.

20. The apparatus according to claim 19, wherein the resilient jaw locking member is a resilient plate and the jaw body includes a pair of inwardly deformable legs, each of the pair of inwardly deformable legs supporting one of the first or second jaw members, the resilient jaw locking member being disposed between the pair of inwardly deformable legs of the jaw body while unactuated.

21. The apparatus according to claim 20, wherein a distal end of the camming member is slidably positioned about the pair of inwardly deformable legs of the jaw body and is movable from the retracted position to the advanced position to move the resilient jaw locking member from between the pair of inwardly deformable legs of the jaw body and to effectuate movement of the first and second jaw members to the approximated position.

* * * * *